US011859006B2

(12) United States Patent
Katagiri et al.

(10) Patent No.: US 11,859,006 B2
(45) Date of Patent: Jan. 2, 2024

(54) METHOD OF TREATING ECTOPIC OSSIFICATION OR DIFFUSE INTRINSIC PONTINE GLIOMA IN A SUBJECT BY ADMINISTERING AN ANTI-ALK2 ANTIBODY

(71) Applicants: SAITAMA MEDICAL UNIVERSITY, Saitama (JP); DAIICHI SANKYO COMPANY, LIMITED, Tokyo (JP)

(72) Inventors: Takenobu Katagiri, Saitama (JP); Sho Tsukamoto, Saitama (JP); Keigo Kumagai, Saitama (JP); Shinnosuke Tsuji, Tokyo (JP)

(73) Assignees: Saitama Medical University, Saitama (JP); Daiichi Sankyo Company, Limited, Tokyo (JP)

( * ) Notice: Subject to any disclaimer, the term of this patent is extended or adjusted under 35 U.S.C. 154(b) by 279 days.

(21) Appl. No.: 16/977,572

(22) PCT Filed: Mar. 4, 2019

(86) PCT No.: PCT/JP2019/008319
§ 371 (c)(1),
(2) Date: Sep. 2, 2020

(87) PCT Pub. No.: WO2019/172165
PCT Pub. Date: Sep. 12, 2019

(65) Prior Publication Data
US 2021/0009709 A1 Jan. 14, 2021

(30) Foreign Application Priority Data
Mar. 5, 2018 (JP) ................................. 2018-039066

(51) Int. Cl.
A61K 39/00 (2006.01)
A61K 39/395 (2006.01)
C07K 16/28 (2006.01)
C12Q 1/6883 (2018.01)

(52) U.S. Cl.
CPC ........ *C07K 16/2896* (2013.01); *C12Q 1/6883* (2013.01); *A61K 39/3955* (2013.01); *A61K 2039/505* (2013.01); *C12Q 2600/106* (2013.01); *C12Q 2600/156* (2013.01)

(58) Field of Classification Search
CPC ....................... A61K 39/3955; A61K 2039/505
See application file for complete search history.

(56) References Cited

U.S. PATENT DOCUMENTS

2016/0075772 A1* 3/2016 Hatsell .................... A61P 43/00
424/134.1
2018/0118835 A1 5/2018 Katagiri et al.

FOREIGN PATENT DOCUMENTS

| EP | 3 252 074 A1 | 12/2017 |
| RU | 2015143542 A | 4/2017 |
| WO | WO-2014/151871 A2 | 9/2014 |
| WO | WO 2016/121908 A1 | 8/2016 |

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Ferrara et al. (2015) mAbs, 7(1):32-41. (doi.org/10.4161/19420862.2015.989047).*
Pacifici M and Shore EM (Feb. 2016) Cytokine Growth Factor Review. 27:93-104. (Published online Dec. 28, 2015. doi: 10.1016/j.cytogfr.2015.12.007).*
Rigueur D, et al. (Apr. 2015) J Bone Miner Res. 30(4): 733-741. (doi: 10.1002/jbmr.2385).*
Hatsell et al., "ACVR1R206H receptor mutation causes fibrodysplasia ossificans progressiva by imparting responsiveness to activin A," Science Translational Medicine, Sep. 2, 2015, 7(303):303ra137, 1-13.
Pang et al., "ACVR1-Fc suppresses BMP signaling and chondroosseous differentiation in an in vitro model of Fibrodysplasia ossificans progressiva," Bone, Aug. 2, 2016, 92:29-36.
Supplementary European Search Report dated Nov. 25, 2021, in EP 19764782.9.
Office action dated May 24, 2022 in RU 2020132133.
Carvalho et al., "Preclinical Efficacy of ALK2 Inhibitors in ACVR1 Mutant DIPG," Neuro-Oncology, Nov. 7, 2016, 18(supply 6), vi154, PDTB-20.
Chaikaud et al., "Structure of the Bone Morphogenetic Protein Receptor ALK2 and Implications for Fibrodysplasia Ossificans Progressiva," J. Biol. Chem., 2012, 287:36990-36998.
Cockle et al., "Cell migration in paediatric glioma; characterization and potential therapeutic targeting," British Journal of Cancer, 2015, 112:693-703.
Fukuda et al., "Constitutively Activated ALK2 and Increased SMAD1/5 Cooperatively Induce Bone Morphogenetic Protein Signaling in Fibrodysplasia Ossificans Progressiva," J. Biol. Chem., 2009, 284:7149-7156.
Hoeman et al., "R206H ACVR1 significantly accelerates diffuse intrinsic pontine glioma pathogenesis," Neuro-Oncology, Nov. 7, 2016, 18(supply 6), vi213, TMOD-30.
International Search Report dated Apr. 9, 2019, in PCT/JP2019/008319.

(Continued)

Primary Examiner — Robert S Landsman
(74) Attorney, Agent, or Firm — Foley & Lardner LLP

(57) ABSTRACT

This application relates to a pharmaceutical composition for use in a method for treating and/or preventing a patient having ectopic ossification and/or brain tumor, wherein the patient has an active mutation in ALK2 protein which is responsible for ectopic ossification or brain tumor; an amino acid residue at position 330 of ALK2 is proline; and an active ingredient of this composition is an anti-ALK2 antibody or an antigen-binding fragment thereof comprising a property of binding to ALK2, a property of cross-linking ALK2, and a property of inhibiting BMP signal transduction.

19 Claims, 8 Drawing Sheets
Specification includes a Sequence Listing.

(56) References Cited

OTHER PUBLICATIONS

Katagiri et al., "The unique activity of bone morphogenetic proteins in bone: a critical role of the Smad signaling pathway," Biol. Chem., 2013, 394(6):703-714.

Katagiri, Takenobu, "Heterotopic Bone Formation Induced by Bone Morphogenetic Protein Signaling: Fibrodysplasia Ossificans Progressiva," J. Oral Biosci., 2010, 52(1):33-41.

Katagiri, Takenobu, "Recent topics in fibrodysplasia ossificans progressive," Journal of Oral Biosciences, 2012, 54:119-123.

Shore et al. "A recurrent mutation in the BMP type I receptor ACVR1 causes inherited and sporadic fibrodysplasia ossificans progressive," Nature Genetics, May 2006, 38(5):525-527.

Taylor et al., "Recurrent activating ACVR1 mutations in diffuse intrinsic pontine glioma," Nature Genetics, May 2014, 46(5):457-462.

Office Action dated Jan. 17, 2023 in TW 108107084.

Taylor et al., "ACVR1 Mutations in DIPG: Lessons Learned from FOP," Cancer Research, 2014, 74(17):4565-4570.

* cited by examiner

Fig. 2
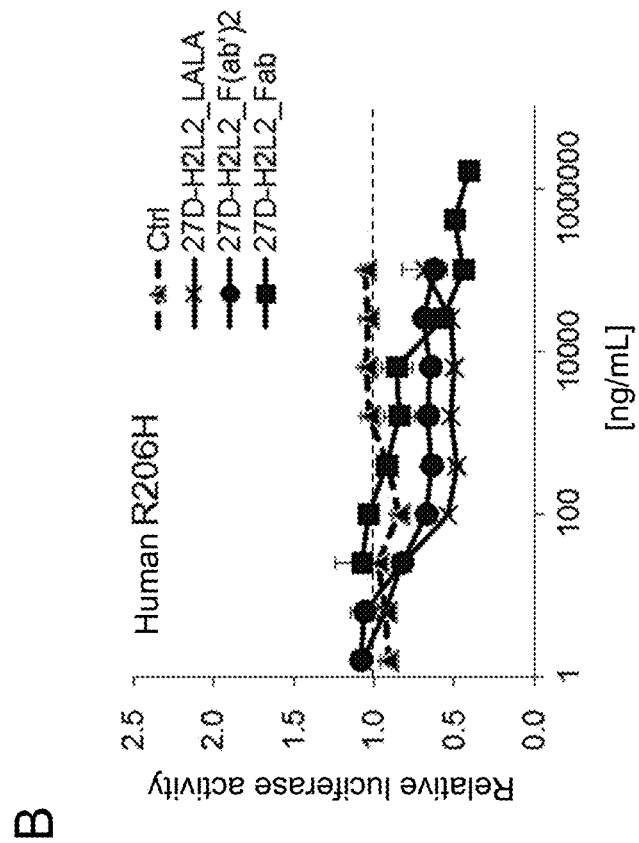
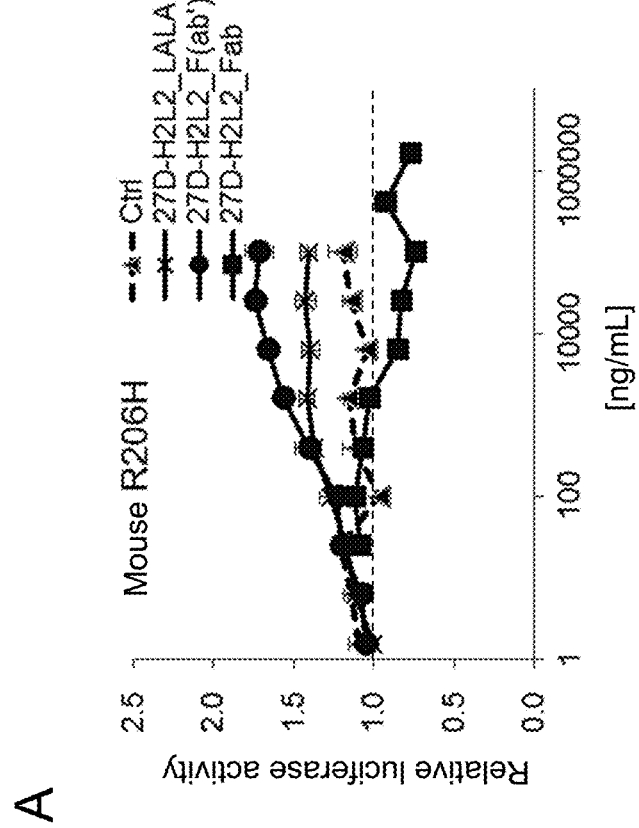

Fig. 4

```
                Signal peptide
Human    1  MVDGVMILPVLIMIALPSPSMEDEKPKVNPKLYMCVCEGLSCGNEDHCEGQQCFSSLSINDGFHVYQKGC   70
Monkey   1  ............I.........................................................   70
Dog      1  ............M..M....F.................................................   70
Rat      1  ....A...S..M.M......E........................................V......R   70
Mouse    1  ............M.M.F...V................R................................   70
                                                              ├── Transmembrane
Human   71  FQVYEQGKMTCKTPPSPGQAVECCQGDWCNRNITAQLPTKGKSFPGTQNFHLEVGLIILSVVFAVCLLAC   140
Monkey  71  ......................................................................   140
Dog     71  .............................................E........................   140
Rat     71  ..............V..R.................S..............................F...   140
Mouse   71  ......................................................................   140
                                                    GS domain
Human  141  LLGVALRKFKRRNQERLNPRDVEYGTIEGLITTNVGDSTLADLLDHSCTSGSGSGLPFLVQRTVARQITL   210
Monkey 141  ......................................................................   210
Dog    141  ......................................................................   210
Rat    141  I........................................E............................   210
Mouse  141  I........................................E............................   210
               Kinase domain                          └─ D182E
Human  211  LECVGKGRYGEVWRGSWQGENVAVKIFSSRDEKSWFRETELYNTVMLRHENILGFIASDMTSRHSSTQLW   280
Monkey 211  ......................................................................   280
Dog    211  ......................................................................   280
Rat    211  ......................................................................   280
Mouse  211  ......................................................................   280

Human  281  LITHYHEMGSLYDYLQLTTLDTVSCLRIVLSIASGLAHLHIEIFGTQGKPAIAHRDLKSKNILVKKNGQC   350
Monkey 281  ......................................................................   350
Dog    281  ......................................................................   350
Rat    281  ................................................S.....................   350
Mouse  281  ................................................S.....................   350
                                                          └─ P330S
Human  351  CIADLGLAVMHSQSTNQLDVGNNPRVGTKRYMAPEVLDETIQVDCFDSYKRVDIWAFGLVLWEVARRMVS   420
Monkey 351  ......................................................................   420
Dog    351  ......................................................................   420
Rat    351  ......................................................................   420
Mouse  351  ......................................................................   420

Human  421  NGIVEDYKPPFYDVVPNDPSFEDMRKVVCVDQQRPNIPNRWFSDPTLTSLAKLMKECWYQNPSARLTALR   490
Monkey 421  ......................................................................   490
Dog    421  ......................................................................   490
Rat    421  ......................................................................   490
Mouse  421  ......................................................................   490

Human  491  IKKTLTKIDNSLDKLKTDC                                                        509
Monkey 491  ...................   Human: SEQ ID. No: 1       509
Dog    491  ...................   Monkey: SEQ ID. No: 40     509
Rat    491  ...................   Dog: SEQ ID. No: 41        509
Mouse  491  ...................   Rat: SEQ ID. No: 42        509
                                   Mouse: SEQ ID. No: 3       509
```

METHOD OF TREATING ECTOPIC OSSIFICATION OR DIFFUSE INTRINSIC PONTINE GLIOMA IN A SUBJECT BY ADMINISTERING AN ANTI-ALK2 ANTIBODY

CROSS-REFERENCE TO RELATED APPLICATIONS

This application is the U.S. National Stage of PCT/JP2019/008319, filed Mar. 4, 2019, which claims priority to JP 2018-039066, filed Mar. 5, 2018.

The instant application contains a Sequence Listing which has been submitted in ASCII format via EFS-WEB and is hereby incorporated by reference in its entirety. Said ASCII copy, created on Aug. 19, 2020, is named sequence.txt and is 69,544 bytes.

TECHNICAL FIELD

The present invention relates to a pharmaceutical composition for use in a method for treating and/or preventing ectopic (or heterotopic) ossification (or bone formation) and/or brain tumor, characterized by administering an anti-ALK2 antibody having ALK2 binding and cross-linking abilities to a patient having an active mutation in ALK2 and having no mutation of the amino acid residue at position 330 of ALK2.

BACKGROUND ART

Fibrodysplasia ossificans progressiva (FOP) is a genetic disease in which a cartilage tissue or bone tissue is ectopically formed in soft tissues, such as skeletal muscle, tendon, and ligament, where bone tissues are not normally formed (Non Patent Literatures 1 to 3). In this disease, ectopic ossification occurs throughout the entire body including the face so that an ectopic bone tissue and an existing bone tissue are fused to remarkably reduce the range of joint motion or to deform the body (Non Patent Literatures 1 to 3).

It is known that the ectopic ossification in FOP includes not only ectopic ossification proceeding chronically with growth, but also acute ectopic ossification proceeding accompanied by a symptom, called flare-up, caused by muscle injury, viral infection, or the like (Non Patent Literature 1). The flare-up is accompanied by the swelling with inflammatory response or sustained pain as principal symptoms, and is known to be induced by bruise, falling, intramuscular injection, or the like, which causes muscle injury. In addition, sudden flare-ups with no clear cause are also known. For FOP, invasive medical procedures, such as biopsy and operation, are contraindicated because ectopic bones can be formed after flare-up. As such, the ectopic bone tissues cannot be surgically removed. The ectopic bone tissues in FOP are formed with normal cartilage cells or osteoblasts and are metabolized in the same manner as normal bone tissues. Because of this, it is impossible to remove only ectopic bone tissues using drugs or the like.

Any fundamental therapy for suppressing the ectopic ossification in FOP has not yet been established, and only symptomatic treatment for pain or the like has been made. Thus, the ectopic bone tissues formed in FOP are very difficult to remove, and the development of a promising drug that can exert prophylactic effects before the onset of ectopic ossification has been expected.

Activin like kinase 2 ALK2) gene, encoding a receptor of bone morphogenetic proteins (BMPs) that induces ectopic bone formation in soft tissues including skeletal muscle tissues, has been identified as a causative gene for FOP (Non Patent Literature 4). ALK2 gene is identical to Activin A type I receptor 1 ACVR1) gene. ALK2 having an amino acid substitution has been found from familial and sporadic FOP cases (Non Patent Literature 4).

Human or mouse ALK2 is a single transmembrane protein consisting of 509 amino acids and having a signal peptide and functions as a transmembrane type of serine/threonine kinase receptor binding to BMPs (Non Patent Literatures 1 to 3). ALK2 binds BMPs at its N-terminal extracellular region to activate the downstream intracellular signaling pathway through its intracellular serine/threonine kinase.

BMP receptors are classified based on their structures and functions into 2 types: type I receptors including ALK2; and type II receptors (Non Patent Literatures 1 to 3). The type II receptors are constitutively active enzymes that exhibit kinase activity even if not bound with BMP. On the other hand, the type I receptors including ALK2 are inactive enzymes in a state unbound with BMP and exhibit kinase activity in a manner dependent on binding to BMP. This is probably because upon binding to BMP, type II receptor kinase phosphorylates type I receptor intracellular domain as the substrate, which may change its conformation, and activates the type I receptor (Non Patent Literatures 1 to 3).

Type I receptors are known to be constitutively activated independent of a type II receptor by substitution of a particular amino acid in the intracellular region (Non Patent Literatures 1 to 3). Overexpression of the constitutively activated mutants of the type I receptors activates the intracellular signaling pathway even when the signal is not stimulated with BMP. Thus, the type I receptors are considered as responsible molecules that transduce BMP signals from the outside to the inside of cells.

The mutation in ALK2 identified from familial and typical sporadic FOP cases was the R206H mutation in which Arg206 is substituted by His (Non Patent Literature 4). All of gene mutations previously identified in FOP cases have been reported to cause amino acid substitutions in the intracellular region of ALK2. Most of these mutations in FOP cases focus on the vicinity of ATP-binding region in the intracellular domain of ALK2 Non Patent Literature 5).

Overexpression of the ALK2 mutants identified in FOP in cultured cells activates the intracellular signaling pathway of BMP even when the signal is not stimulated with BMP (Non Patent Literature 6). Accordingly, anti-ALK2 antibodies that can be expected to have inhibitory effect on wild-type ALK2 and various intracellular ALK2 mutants including novel unidentified mutants by acting on the extracellular region of ALK2 and inhibiting its signal transduction are being developed as therapeutics for FOP (Patent Literature 1).

Diffuse intrinsic pontine glioma (DIPG) is diffuse (infiltrative) astrocytoma that is found mainly in the pons in the brain and reportedly accounts for approximately 75 to 80% of pediatric brain stem tumors. DIPG is a rare disease with a long-term survival rate of fewer than 10%, because the brain stem regulates essential functions such as respiration. The same mutations in ALK2 in FOP cases have also been identified in DIPG cases (Non Patent Literature 7). Thus, anti-ALK2 antibodies may be able to treat brain tumor such as DIPG.

PRIOR ART LITERATURE

Patent Literature

Patent Literature 1: International Publication No. WO 2016/121908

Non Patent Literature

Non Patent Literature 1: T. Katagiri, J. Oral Biosci., 52, 33-41 (2010)
Non Patent Literature 2: T. Katagiri, J. Oral Biosci., 54, 119-123 (2012)
Non Patent Literature 3: T. Katagiri and S. Tsukamoto, Biol. Chem., 394, 703-714 (2013)
Non Patent Literature 4: E. M. Shore et al., Nat. Genet., 38, 525-527 (2006)
Non Patent Literature 5: A. Chaikuad et al., J. Biol. Chem., 287, 36990-36998 (2012)
Non Patent Literature 6: T. Fukuda et al., J. Biol. Chem., 284, 7149-7156 (2009)
Non Patent Literature 7: K. R. Taylor et al., Nat Genet., 46, 457-461 (2014)

SUMMARY OF INVENTION

Problem to be Solved by the Invention

An object of the present invention is to provide an effective method for treating and/or preventing ectopic (or heterotopic) ossification (or bone formation) and/or brain tumor, and a pharmaceutical composition for use in the method.

Means for Solution of the Problem

The present inventors have evaluated anti-ALK2 antibodies as therapeutics for FOP and consequently found that the administration of the anti-ALK2 antibody to FOP mouse models promotes ectopic ossification. The present inventors have conducted diligent studies to attain the object and consequently have now found that the anti-ALK2 antibody promotes the intracellular signal transduction of mouse ALK2 having R206H mutation, but rather inhibits the intracellular signal transduction when human ALK2 having R206H mutation is used. Accordingly, as a result of performing intracellular and extracellular substitutions in human ALK2 and mouse ALK2, the anti-ALK2 antibody has been now found to promote the ALK2 intracellular signal transduction when an intracellular region is derived from mouse ALK2 having R206H mutation. The comparison of the amino acid sequences of the intracellular regions between human ALK2 and mouse ALK2 has revealed that their amino acid sequences differ only in the amino acid residues at position 182 i.e., aspartic acid (D) for human and glutamic acid (E) for mouse) and at position 330 i.e., proline (P) for human and serine (S) for mouse). Accordingly, the present inventors have prepared mutants by substituting aspartic acid (D) at position 182 and proline (P) at position 330 of human ALK2 having R206H mutation by the mouse amino acid residues, i.e. glutamic acid (E) and serine (S), respectively, and then have studied the effect of the anti-ALK2 antibodies on the mutants. As a result, it has been now revealed that the anti-ALK2 antibodies promote the intracellular signal transduction when proline (P) at position 330 of human ALK2 having R206H mutation is substituted by serine (S). The substitution of proline (P) at position 330 by aspartic acid (D), glutamic acid (E) or alanine (A) has been now found to give similar results. The anti-ALK2 antibodies have been further found to enhance ALK2-mediated BMP signal transduction when glycine (G) at position 328 of human ALK2 having no R206H mutation is substituted by valine (V). As a result, the present inventors have completed the present invention through the finding that the ectopic ossification and/or brain tumor can be effectively treated and/or prevented by administering the anti-ALK2 antibodies only to patients having no mutation of an amino acid residue at position 330 of ALK2 and/or patients having no G328V mutation of ALK2 among patients having an active mutation in ALK2.

Specifically, the present invention encompasses the following features:

1) A pharmaceutical composition for use in a method for treating and/or preventing a patient having ectopic ossification, wherein:
  the patient has an active mutation in an Activin like kinase 2 ALK2) protein which is responsible for ectopic ossification;
  an amino acid residue at position 330 of the ALK2 is proline; and
  an active ingredient of the composition is an anti-ALK2 antibody or an antigen-binding fragment thereof comprising a property of binding to the ALK2, a property of cross-linking the ALK2, and a property of inhibiting BMP signal transduction.

(2) The pharmaceutical composition according to (1), wherein the ALK2 has no G328V mutation.

(3) The pharmaceutical composition according to (1), wherein the method comprises the steps of:
  (a) detecting the presence or absence of an active mutation in ALK2 in patients;
  (b) selecting a patient having the active mutation in ALK2;
  (c) confirming that the patient has no mutation of an amino acid residue at position 330 of ALK2; and
  (d) administering the anti-ALK2 antibody or the antigen-binding fragment thereof to the selected patient.

(4) The pharmaceutical composition according to (3), wherein the step (c) further comprises the step of confirming that the ALK2 of the patient has no G328V mutation.

(5) The pharmaceutical composition according to (3), wherein the selection of the patient to which the anti-ALK2 antibody or the antigen-binding fragment thereof is to be administered comprises the steps of:
  (a) detecting the presence or absence of an active mutation in ALK2 in ectopic ossification patients;
  (b) selecting a patient having the active mutation in ALK2; and
  (c) excluding a patient having a mutation of an amino acid residue at position 330 of ALK2.

(6) The pharmaceutical composition according to (5), wherein the step (c) further comprises the step of excluding a patient having G328V mutation in ALK2.

(7) The pharmaceutical composition according to any of (1) to (6), wherein the anti-ALK2 antibody or the antigen-binding fragment thereof specifically binds to a polypeptide consisting of amino acid residues from position 21 to position 123 in the amino acid sequence of SEQ ID NO: 1.

(8) The pharmaceutical composition according to any of (1) to (7), wherein the anti-ALK2 antibody or the antigen-binding fragment thereof binds to:
  (i) an epitope comprising each residue of glutamic acid at position 38, glycine at position 39, isoleucine at position 59, asparagine at position 60, aspartic acid at position 61, glycine at position 62, phenylalanine at position 63, histidine at position 64, valine at position 65, tyrosine at position 66, asparagine at position 102, threonine at position 104, glutamine at position 106, and leucine at position 107 in the amino acid sequence of SEQ ID NO: 1; or (ii) an epitope comprising each residue of glutamic acid at position 38, glycine at position 39, leucine at position 40, isoleucine at position 59, asparagine at position 60, aspartic acid at position 61, glycine at position 62, phenylalanine at position 63, histidine at position 64, valine at position 65, tyrosine at position 66, and threonine at position 104 in the amino acid sequence of SEQ ID NO: 1.

(9) The pharmaceutical composition according to any of (1) to (7), wherein the anti-ALK2 antibody or the antigen-binding fragment thereof competes, for binding to ALK2, with the anti-ALK2 antibody or the antigen-binding fragment thereof according to (8).

(10) The pharmaceutical composition according to any of (1) to (9), wherein the anti-ALK2 antibody or the antigen-binding fragment thereof is a monoclonal antibody, a polyclonal antibody, a chimeric antibody, a humanized antibody, a human antibody, a diabody, a multispecific antibody, or F(ab')$_2$.

(11) The pharmaceutical composition according to any of (1) to (10), wherein a heavy chain sequence of the anti-ALK2 antibody or the antigen-binding fragment thereof comprises a variable region having CDRH1, CDRH2, and CDRH3, wherein the CDRH1, the CDRH2, and the CDRH3 consist of the amino acid sequences of:

SEQ ID NO: 5, SEQ ID NO: 6, and SEQ ID NO: 7, respectively;

SEQ ID NO: 11, SEQ ID NO: 12, and SEQ ID NO: 13, respectively;

SEQ ID NO: 18, SEQ ID NO: 19, and SEQ ID NO: 20, respectively; or

SEQ ID NO: 24, SEQ ID NO: 25, and SEQ ID NO: 26, respectively, and a light chain sequence thereof comprises a variable region having CDRL1, CDRL2, and CDRL3, wherein the CDRL1, the CDRL2, and the CDRL3 consist of the amino acid sequences of SEQ ID NO: 8, SEQ ID NO: 9, and SEQ ID NO: 10, respectively;

SEQ ID NO: 8, SEQ ID NO: 17, and SEQ ID NO: 10, respectively;

SEQ ID NO: 14, SEQ ID NO: 15, and SEQ ID NO: 16, respectively;

SEQ ID NO: 21, SEQ ID NO: 22, and SEQ ID NO: 23, respectively; or

SEQ ID NO: 27, SEQ ID NO: 28, and SEQ ID NO: 29, respectively.

(12) The pharmaceutical composition according to any of (1) to (11), wherein the heavy chain variable region sequence of the anti-ALK2 antibody or the antigen-binding fragment thereof is:

a1) an amino acid sequence consisting of amino acid residues from position 20 to position 142 of the amino acid sequence of SEQ ID NO: 31;

a2) an amino acid sequence consisting of amino acid residues from position 20 to position 142 of the amino acid sequence of SEQ ID NO: 33;

a3) an amino acid sequence consisting of amino acid residues from position 20 to position 140 of the amino acid sequence of SEQ ID NO: 34;

a4) an amino acid sequence consisting of amino acid residues from position 20 to position 140 of the amino acid sequence of SEQ ID NO: 36;

a5) an amino acid sequence consisting of amino acid residues from position 20 to position 140 of the amino acid sequence of SEQ ID NO: 38;

a6) an amino acid sequence consisting of amino acid residues from position 20 to position 140 of the amino acid sequence of SEQ ID NO: 39;

a7) an amino acid sequence having at least 95% identity to any one amino acid sequence selected from the amino acid sequences a1) to a6);

a8) an amino acid sequence having at least 99% identity to any one amino acid sequence selected from the amino acid sequences a1) to a6); or a9) an amino acid sequence comprising a substitution(s), a deletion(s), or an addition(s) of one or several amino acid residues in any one amino acid sequence selected from the amino acid sequences a1) to a6), and the light chain variable region sequence is:

b1) an amino acid sequence consisting of amino acid residues from position 21 to position 133 of the amino acid sequence of SEQ ID NO: 32;

b2) an amino acid sequence consisting of amino acid residues from position 21 to position 129 of the amino acid sequence of SEQ ID NO: 35;

b3) an amino acid sequence consisting of amino acid residues from position 21 to position 129 of the amino acid sequence of SEQ ID NO: 37;

b4) an amino acid sequence having at least 95% identity to any one amino acid sequence selected from the amino acid sequences b1) to b3);

b5) an amino acid sequence having at least 99% identity to any one amino acid sequence selected from the amino acid sequences b1) to b3); or b6) an amino acid sequence comprising a substitution(s), a deletion(s), or an addition(s) of one or several amino acid residues in any one amino acid sequence selected from the amino acid sequences b1) to b3).

(13) The pharmaceutical composition according to (12), wherein the anti-ALK2 antibody is:

an antibody consisting of a heavy chain comprising a heavy chain variable region consisting of amino acid residues from position 20 to position 142 of the amino acid sequence of SEQ ID NO: 31 and a light chain comprising a light chain variable region consisting of amino acid residues from position 21 to position 133 of the amino acid sequence of SEQ ID NO: 32;

an antibody consisting of a heavy chain comprising a heavy chain variable region consisting of amino acid residues from position 20 to position 142 of the amino acid sequence of SEQ ID NO: 33 and a light chain comprising a light chain variable region consisting of amino acid residues from position 21 to position 133 of the amino acid sequence of SEQ ID NO: 32;

an antibody consisting of a heavy chain comprising a heavy chain variable region consisting of amino acid residues from position 20 to position 140 of the amino acid sequence of SEQ ID NO: 34 and a light chain comprising a light chain variable region consisting of amino acid residues from position 21 to position 129 of the amino acid sequence of SEQ ID NO: 35;

an antibody consisting of a heavy chain comprising a heavy chain variable region consisting of amino acid residues from position 20 to position 140 of the amino acid sequence of SEQ ID NO: 36 and a light chain comprising a light chain variable region consisting of amino acid residues from position 21 to position 129 of the amino acid sequence of SEQ ID NO: 37;

an antibody consisting of a heavy chain comprising a heavy chain variable region consisting of amino acid residues from position 20 to position 140 of the amino acid sequence of SEQ ID NO: 38 and a light chain comprising a light chain variable region consisting of amino acid residues from position 21 to position 129 of the amino acid sequence of SEQ ID NO: 35; or an antibody consisting of a heavy chain comprising a heavy chain variable region consisting of amino acid residues from position 20 to position 140 of the amino acid sequence of SEQ ID NO: 39 and a light chain comprising a light chain variable region consisting of amino acid residues from position 21 to position 129 of the amino acid sequence of SEQ ID NO: 37.

(14) The pharmaceutical composition according to any of (1) to (13), wherein the active mutation in ALK2 is at least one selected from L196P, delP197_F198insL, R202I, R206H, Q207E, R258S, R258G, G325A, G328E, G328R, G328W, G356D, and R375P.

(15) The pharmaceutical composition according to any of (1) to (13), wherein the active mutation in ALK2 is R206H mutation.

(16) The pharmaceutical composition according to any of (1) to (15), wherein the ectopic ossification is fibrodysplasia ossificans progressiva (FOP).

(17) A pharmaceutical composition for use in a method for treating and/or preventing a patient having brain tumor, wherein the patient has an active mutation in Activin like kinase 2 ALK2) protein which is responsible for brain tumor; and an active ingredient of the composition is an anti-ALK2 antibody or an antigen-binding fragment thereof comprising a property of binding to the ALK2, a property of cross-linking the ALK2, and a property of inhibiting BMP signal transduction.

(18) The pharmaceutical composition according to (17), wherein an amino acid residue at position 330 of ALK2 in the patient is proline.

(19) The pharmaceutical composition according to (17) or (18), wherein the active mutation in ALK2 is at least one selected from R206H, R258G, G328E, G328W, and G356D.

(20) The pharmaceutical composition according to any of (17) to (19), wherein the anti-ALK2 antibody or the antigen-binding fragment thereof is an anti-ALK2 antibody or an antigen-binding fragment thereof defined in any of (7) to (13).

(21) The pharmaceutical composition according to any of (17) to (20), wherein the brain tumor is diffuse intrinsic pontine glioma (DIPG).

(22) A method for predicting a risk of developing an adverse reaction ascribable to administration of an anti-ALK2 antibody or an antigen-binding fragment thereof, comprising the following steps of:
(a) detecting the presence or absence of an active mutation in ALK2 and a mutation of an amino acid residue at position 330 of ALK2 of a patient; and
(b) determining that when the patient has the active mutation in ALK2 and has no mutation of an amino acid residue at position 330 of ALK2, the patient has a low risk of developing an adverse reaction ascribable to the administration of an anti-ALK2 antibody or an antigen-binding fragment thereof.

(23) A method for predicting responsiveness to treatment and/or prevention by administration of an anti-ALK2 antibody or an antigen-binding fragment thereof, comprising the following steps of:
(a) detecting the presence or absence of an active mutation in ALK2 and a mutation of an amino acid residue at position 330 of ALK2 of a patient; and
(b) determining that when the patient has the active mutation in ALK2 and has no mutation of an amino acid residue at position 330 of ALK2, the patient has responsiveness to treatment and/or prevention by the administration of an anti-ALK2 antibody or an antigen-binding fragment thereof.

(24) A method for selecting a patient to be treated and/or prevented by administration of an anti-ALK2 antibody or an antigen-binding fragment thereof, comprising the following steps of:
(a) detecting the presence or absence of an active mutation in ALK2 and a mutation of an amino acid residue at position 330 of ALK2 of a patient; and
(b) selecting the patient as a patient to be treated and/or prevented by the administration of an anti-ALK2 antibody or an antigen-binding fragment thereof when the patient has the active mutation in ALK2 and has no mutation of an amino acid residue at position 330 of ALK2.

(25) A method for treating and/or preventing a disease by administration of an anti-ALK2 antibody or an antigen-binding fragment thereof, comprising the following steps of:
(a) detecting the presence or absence of an active mutation in ALK2 and a mutation of an amino acid residue at position 330 of ALK2 of a patient; and
(b) administering to the patient the anti-ALK2 antibody or the antigen-binding fragment thereof when the patient has the active mutation in ALK2 and has no mutation of an amino acid residue at position 330 of ALK2.

(26) The method according to (25), further comprising performing the step (b) of the method according to any of (22) to (24).

(27) The method according to any of (22) to (26), wherein the administration of the anti-ALK2 antibody or the antigen-binding fragment thereof is administration of a pharmaceutical composition according to any of (1) to (21).

(28) The method according to any of (22) to (27), wherein the step (b) further comprises confirming that the active mutation in ALK2 is not G328V mutation.

(29) The method according to any of (22) to (28), wherein the active mutation in ALK2 is at least one selected from L196P, delP197_F198insL, R202I, R206H, Q207E, R258S, R258G, G325A, G328E, G328R, G328W, G356D, and R375P.

(30) The method according to any of (22) to (28), wherein the active mutation in ALK2 is at least one selected from R206H, R258G, G328E, G328W, and G356D.

(31) The method according to any of (25) to (30), wherein the disease affecting the patient is ectopic ossification or brain tumor.

(32) The method according to (31), wherein the disease affecting the patient is ectopic ossification.

(33) The method according to any of (25) to (31), wherein the disease affecting the patient is fibrodysplasia ossificans progressiva (FOP) or diffuse intrinsic pontine glioma (DIP G).

(34) The method according to (33), wherein the disease affecting the patient is fibrodysplasia ossificans progressiva (FOP).

The present specification includes the contents disclosed in Japanese Patent Application No. 2018-039066 from which the present application claims the priority.

The present invention provides an efficient method for treating and/or preventing ectopic ossification and/or brain tumor in a particular patient, and a pharmaceutical composition for use in the method. The present invention also provides a method for predicting a risk of developing an adverse reaction ascribable to administration of an anti-ALK2 antibody, a method for predicting responsiveness to treatment and/or prevention by administration of an anti-ALK2 antibody, and a method for selecting a subject to be treated and/or prevented by administration of an anti-ALK2 antibody. The present invention further provides a method for treating and/or preventing a disease caused by an active mutation in ALK2 e.g., ectopic ossification and/or brain tumor) by administration of an anti-ALK2 antibody or an antigen-binding fragment thereof.

BRIEF DESCRIPTION OF DRAWINGS

FIG. 2A-B This figure provides graphs is a graph showing, using a BMP-specific luciferase reporter, that F(ab')2 (27D-H2L2_F(ab)$_2$') activates the BMP signal transduction only in HEK293 cells expressing mouse R206H ALK2 (FIG. 2A), as in the anti-ALK2 antibody (27D-H2L2_LALA'), whereas Fab (27D-H2L2_Fab') does not activate the BMP signal transduction even in HEK293 cells expressing either mouse or human R206H ALK2 (FIGS. 2A and 2B, respectively). The ordinate depicts relative luciferase activity (Relative luc activity) to an untreated control (i.e., a control free from the F(ab')$_2$). The abscissa depicts an antibody concentration, and a control antibody (Ctrl) is IgG1.

FIG. 4 This figure is a sequence alignment showing that in the sequence comparison among human, monkey, dog, rat and mouse ALK2 proteins, neither the amino acid residue at position 182 i.e., human "D" and mouse "E") nor the amino acid residue at position 330 i.e., human "P" and mouse "S") is conserved between human and mouse.

DETAILED DESCRIPTION OF THE INVENTION

Figure 1:
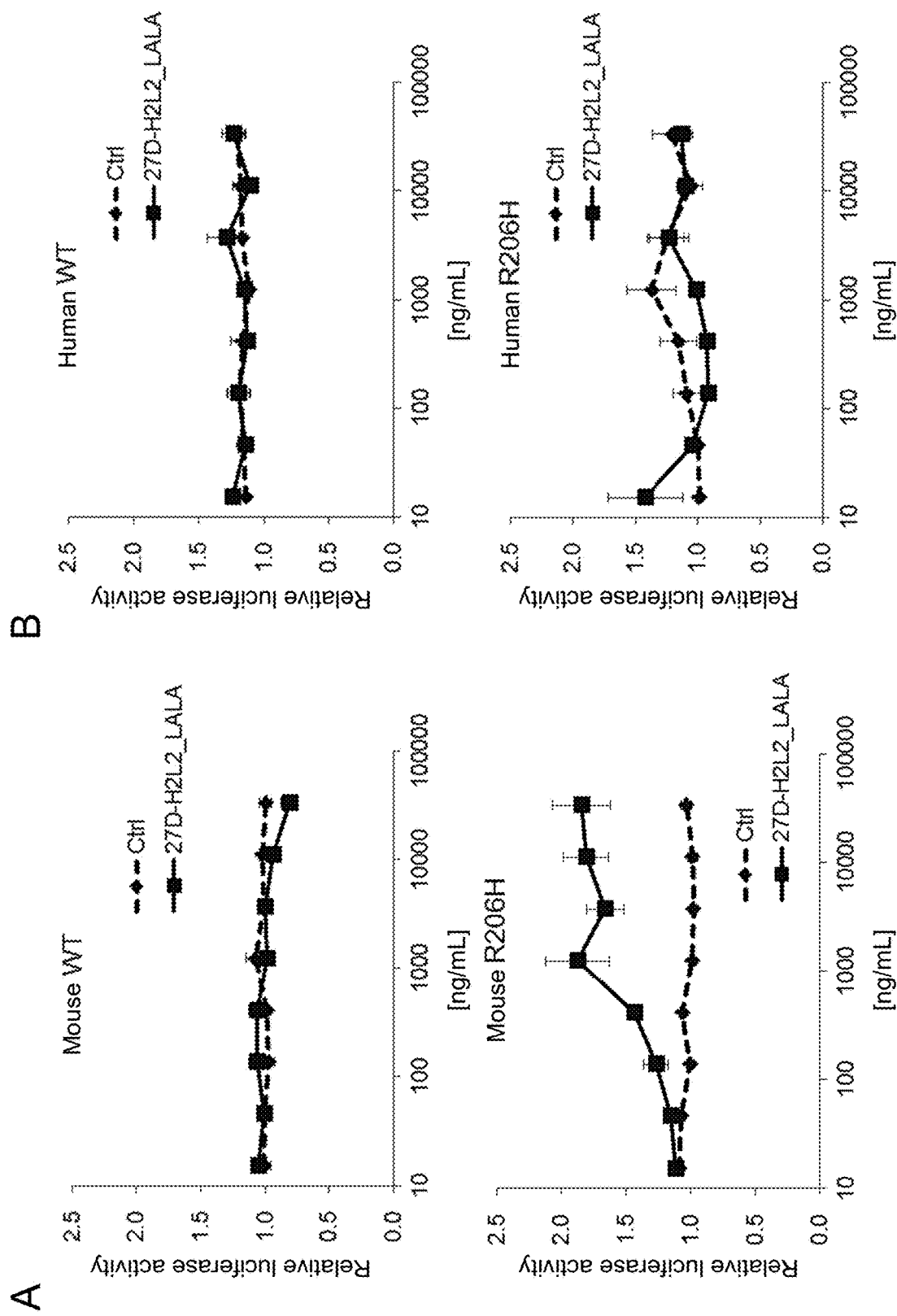
FIG. 1A-B This figure provides graphs is a graph showing, using a BMP-specific luciferase reporter, that an anti-ALK2 antibody (27D-H2L2 LALA) activates the BMP signal transduction in HEK293 cells expressing mouse R206H ALK2 (FIG. 1A), whereas the antibody does not activate the BMP signal transduction in HEK293 cells expressing human R206H ALK2 (FIG. 1B). The ordinate depicts relative luciferase activity (Relative luc activity) to an untreated control (i.e., a control free from the anti-ALK2 antibody). The abscissa depicts an antibody concentration. Control ALK2 proteins are mouse wild-type ALK2 (Mouse WT ALK2') and human wild-type ALK2(Human WT ALK2'), and a control antibody (Ctrl) is IgG1.

The present invention will be described in more detail.

1. Definition

As used herein, the term "gene" includes not only DNA but mRNA, cDNA, and cRNA.

As used herein, the term "polynucleotide" is used with the same meaning as a nucleic acid and also includes, for example, DNA, RNA, probes, oligonucleotides, and primers.

As used herein, the "polypeptide" and the "protein" are used interchangeably with each other.

As used herein, the "RNA fraction" refers to a fraction containing RNA.

As used herein, the "cell" also includes cells within animal individuals and cultured cells.

As used herein, "ALK2" is used with the same meaning as ALK2 protein and includes wild-type ALK2 and mutants thereof (also referred to as "mutant").

As used herein, the "antigen-binding fragment of an (the) antibody", also called "functional fragment of an (the) antibody", means a partial fragment of the antibody having an activity binding to the antigen and includes, for example, F(ab')$_2$, diabodies, linear antibodies, single-chain Fvs, and multispecific antibodies formed from antibody fragments. However, the antigen-binding fragment is not limited to these molecules as long as the antigen-binding fragment has an ability to bind to ALK2 or a property of binding to the ALK2) and has an ability to cross-link ALK2 or a property of cross-linking ALK2), as in the anti-ALK2 antibody. Preferably, the antigen-binding fragment of the antibody further has an ability to inhibit BMP signal transduction (or a property of inhibiting BMP signal transduction), as in the anti-ALK2 antibody. Such an antigen-binding fragment includes not only a fragment obtained by treating a full-length molecule of the antibody protein with an appropriate enzyme but a protein produced in appropriate host cells using a genetically engineered antibody gene.

As used herein, the "epitope", also called "antigenic determinant", generally refers to an antibody-binding antigenic site consisting of at least 7 amino acids, at least 8 amino acids, at least 9 amino acids, or at least 10 amino acids, of an antigen. As used herein, the "epitope" means a partial peptide or a partial conformation of ALK2 to which a particular anti-ALK2 antibody binds. The epitope as a partial peptide of ALK2 may be determined by a method well known to those skilled in the art such as immunoassay and may be determined, for example, by the following method in which various partial structures of ALK2 are prepared. For the preparation of the partial structures, an oligopeptide synthesis technique known in the art may be used. For example, a series of polypeptide fragments having an appropriate length are prepared in order from the C or N terminus of ALK2 using gene recombination techniques well known to those skilled in the art. Then, the reactivity of the antibody with the polypeptide fragments is studied to roughly determine recognition sites. Then, shorter peptides are synthesized, and the reactivity of the antibody with these peptides may be studied to determine the epitope. Alternatively, the epitope as a partial conformation of ALK2 to which a particular ALK2 antibody binds may be determined by identifying amino acid residues of ALK2 adjacent to the antibody by X-ray crystal structure analysis. If a second anti-ALK2 antibody binds to a partial peptide or a partial conformation that is bound by a first anti-ALK2 antibody, then the first antibody and the second antibody may be determined to share an epitope. In addition, even if a specific sequence or structure of an epitope is not determined, the first antibody and the second antibody may be determined to share the epitope by confirming that the second anti-ALK2 antibody (cross-)competes with the first anti-ALK2 antibody for binding to ALK2 i.e., that the second antibody interferes with binding of the first antibody to ALK2). Furthermore, when the first antibody and the second antibody bind to a common epitope and the first antibody has an activity such as inhibitory activity against ALK2-mediated BMP signal transduction, the second antibody can also be expected to have similar activity.

The heavy and light chains of an antibody molecule are known to each have three complementarity determining regions (CDRs). The complementarity determining regions, also called hypervariable domains, are located in the variable regions of the antibody heavy and light chains. These sites have a particularly highly variable primary structure and are separated into three places on the respective primary structures of heavy and light chain polypeptide chains. As used herein, the complementarity determining regions of an antibody are referred to as CDRH1, CDRH2, and CDRH3 from the amino terminus of the heavy chain amino acid sequence for the complementarity determining regions of the heavy chain and as CDRL1, CDRL2, and CDRL3 from the amino terminus of the light chain amino acid sequence for the complementarity determining regions of the light chain. These sites are proximal to each other on the conformation and determine specificity for the antigen to be bound.

In the present invention, the term "hybridizing under stringent conditions" means hybridization under conditions involving hybridization at approximately 50 to 70° C. (e.g., 68° C.) in a commercially available hybridization solution ExpressHyb Hybridization Solution (manufactured by Clontech Laboratories, Inc.), or hybridization at approximately 50 to 70° C. (e.g., 68° C.) in the presence of approximately 0.7 to 1.0 M NaCl using a DNA-immobilized filter, followed by washing at approximately 50 to 70° C. (e.g., 68° C.) using an SSC solution having an approximately 0.1 to 2× concentration (SSC having a 1× concentration consists of 150 mM NaCl and 15 mM sodium citrate; if necessary, the solution may contain approximately 0.1 to 0.5% SDS) which permits identification, or hybridization under conditions equivalent thereto.

As used herein, the term "several" in the phrase "one or several" refers to 2 to 10. The term "several" is preferably 10 or less, more preferably 5 or 6 or less, far more preferably 2 or 3.

In the present invention, the "cross-linking ability" or the "ability to cross-link" refers to the ability of one antibody or an antigen-binding fragment to bind to the respective extracellular regions in two molecules of the ALK2 protein, thereby cross-linking these molecules. Typically, ALK2 forms a complex in the presence of a BMP ligand to activate downstream SMAD1/5/8. The anti-ALK2 antibody induces the cross-link between two molecules of ALK2, probably leading to complex-like formation even in the absence of the ligand. The present inventors have now found that an anti-ALK2 antibody that binds to ALK2 inhibits the BMP signal transduction when the amino acid residue at position 330 in a mutant of human ALK2 protein is proline and, in some cases, when a mutant of human ALK2 protein has no G328V mutation, but that the anti-ALK2 antibody promotes (or activates) the BMP signal transduction when the proline at position 330 is a different amino acid residue such as serine, aspartic acid, glutamic acid, or alanine. On the basis of this finding, when a patient has proline at position 330 in a mutant of human ALK2 protein, and in some cases, has no G328V mutation in the mutant of human ALK2 protein, the patient identified so may be effectively treated with the anti-ALK2 antibody.

As used herein, the promotion of BMP signal transduction refers to activating the downstream intracellular signaling pathway via the ALK2 receptor molecule.

In the present invention, the "patient" is not only a human affected by (or suffered from) a disease, but may also be a human suspected of being affected by a disease.

The "biological sample" as used herein is not particularly limited as long as the presence or absence of a mutation in ALK2 is detectable in a biological sample. The biological sample is, for example, a blood sample or a tumor sample. The biological sample may be protein extracts or nucleic acid extracts (e.g., mRNA extracts, and a cDNA preparation and a cRNA preparation prepared from the mRNA extracts) obtained from these samples.

2. ALK2

The ALK2 gene is a causative gene for FOP encoding a receptor of BMP that induces ectopic bone formation in soft tissues including skeletal muscle tissues. Mutant ALK2 having amino acid substitutions has been found in familial and sporadic FOP cases. For example, L196P (i.e., the mutation that substitutes leucine at position 196 by proline), delP197_F198insL (also referred to as "PF197-8L") (i.e. the mutation that deletes proline at position 197 and phenylalanine at position 198 and, instead, inserts leucine between them), R202I i.e., the mutation that substitutes arginine at position 202 by isoleucine), R206H (i.e., the mutation that substitutes arginine at position 206 by histidine), Q207E (i.e., the mutation that substitutes glutamine at position 207 by glutamic acid), R258S (i.e., the mutation that substitutes arginine at position 258 by serine), R258G (i.e., the mutation that substitutes arginine at position 258 by glycine), G325A (i.e., the mutation that substitutes glycine at position 325 by alanine), G328E (i.e., the mutation that substitutes glycine at position 328 by glutamic acid), G328R (i.e., the mutation that substitutes glycine at position 328 by arginine), G328W (i.e., the mutation that substitutes glycine at position 328 by tryptophan), G356D (i.e., the mutation that substitutes glycine at position 356 by aspartic acid), and R375P (i.e., the mutation that substitutes arginine at position 375 by proline) in the amino acid sequence of SEQ ID NO: 1 are known as active mutations in human ALK2.

Mutant ALK2 having an amino acid substitution(s) has also been found in DIPG cases. R206H, R258G, G328E, G328V (which is the mutation that substitutes glycine at position 328 by valine), G328W, G356D, and the like in the amino acid sequence of SEQ ID NO: 1 are known as active mutations in human ALK2.

ALK2 used herein may be obtained by in vitro synthesis or by production from host cells through gene manipulation. Specifically, ALK2 cDNA is inserted into a vector that permits its expression. Then, the ALK2 protein may be obtained by synthesis in solutions containing enzymes, substrates, and energy substances necessary for transcription and translation, or by expression in other prokaryotic or eukaryotic host cells transformed with the vector.

ALK2 used herein is from a mammal including human or mouse. For example, the amino acid and nucleotide sequences of human ALK2 are available with reference to GenBank Accession No. NM_001105. Herein, similarly the amino acid sequence is disclosed as SEQ ID NO: 1, and the nucleotide sequence is disclosed as SEQ ID NO: 2. The amino acid and nucleotide sequences of mouse ALK2 are available with reference to GenBank Accession No. NP_001103674. Herein, similarly the amino acid sequence is disclosed as SEQ ID NO: 3, and the nucleotide sequence is disclosed as SEQ ID NO: 4. Furthermore, the amino acid sequences of monkey, rat and dog ALK2s are available with reference to GenBank Accession Nos. NM-001260761 (SEQ ID NO: 40), NP_077812 (SEQ ID NO: 42), and XM_549615.5 (SEQ ID NO: 41), respectively. ALK2 is also called ACVR1 Activin A type I receptor 1) or ACTR1 Activin receptor type 1), and all of these terms represent the same molecules.

The ALK2 cDNA may be obtained by a so-called PCR method which involves carrying out polymerase chain reaction (hereinafter, referred to as "PCR") (Saiki, R. K., et al., Science, (1988) 239, 487-49), for example, using a cDNA library expressing the ALK2 cDNA as a template and primers specifically amplifying the ALK2 cDNA.

3. Detection of Mutation in ALK2

Herein, the term "detecting a mutation" means detecting a mutation on genomic DNA as a rule. Alternatively, when the mutation on the genomic DNA is reflected in change of a base(s) in a transcribed product or in change of an amino acid(s) in a translated product, this term also means including detecting this change in the transcribed product or the translated product (i.e., indirect detection).

In a preferred embodiment, the method of the present invention is a method of directly determining a nucleotide sequence of an ALK2 gene region of a patient, thereby detecting a mutation. As used herein, the "ALK2 gene region" means a certain region on genomic DNA containing the ALK2 gene. The region also contains the expression control regions (e.g., a promoter region and an enhancer region) of the ALK2 gene, a 3'-terminal untranslated region of the ALK2 gene, and the like. A mutation in these regions may influence, for example, the transcription activity of the ALK2 gene.

In this method, first, a DNA sample is prepared from a biological sample derived from a patient. Examples of the DNA sample include genomic DNA samples, and cDNA samples prepared from RNA by reverse transcription.

A method for extracting genomic DNA or RNA from the biological sample is not particularly limited, and approaches known in the art may be appropriately selected for use in the extraction. Examples of the method for extracting genomic DNA include a SDS phenol method (i.e., a method which involves: denaturing proteins in tissues preserved in a urea-containing solution or in ethanol, using a proteolytic enzyme (proteinase K), a surfactant (SDS), and phenol; and extracting DNA by precipitation from the tissues using ethanol), and DNA extraction methods using Clean Columns® (manufactured by NextTec Biotechnolgie GmbH), Aqua-Pure®) (manufactured by Bio-Rad Laboratories, Inc.), ZR Plant/Seed DNA Kit (manufactured by Zymo Research Corp.), Aqua Genomic Solution® (manufactured by MoBiTec GmbH), prepGEM® (manufactured by ZyGEM NZ Ltd.) or BuccalQuick® (manufactured by TrimGen Corp.). Examples of the method for extracting RNA include extraction methods using phenol and a chaotropic salt (more specifically, extraction methods using a commercially available kit such as TRIzol (manufactured by Invitrogen Corp.) or ISOGEN (manufactured by Wako Pure Chemical Industries, Ltd.)), and methods using other commercially available kits (RNAPrep Total RNA Extraction Kit (manufactured by Beckman Coulter, Inc.), RNeasy Mini (manufactured by Qiagen N.V.), RNA Extraction Kit (manufactured by Pharmacia Biotech Inc.), etc.). Examples of reverse transcriptase for use in the preparation of cDNA from the extracted RNA include, but are not particularly limited to, reverse transcriptase derived from retrovirus such as RAV (Rous associated virus) or AMV (avian myeloblastosis virus), and reverse transcriptase derived from mouse retrovirus such as MMLV (Moloney murine leukemia virus).

In this aspect, DNA containing a mutation site in the ALK2 gene region is subsequently isolated, and the nucleotide sequence of the isolated DNA is determined. The isolation of the DNA may be performed by, for example, PCR using a pair of oligonucleotide primers designed so as to flank on the both sides of the mutation in the ALK2 gene region, and using the genomic DNA or the RNA as a template. The determination of the nucleotide sequence of the isolated DNA may be performed by, for example, a method known to those skilled in the art, such as Maxam-Gilbert method or Sanger method, or a method using a next-generation sequencer.

The determined nucleotide sequence of the DNA or the cDNA may be compared with a control (e.g., a nucleotide sequence of the corresponding DNA or cDNA derived from biological samples of healthy people), thereby determining the presence or absence of the mutation in the ALK2 gene region of the patient.

The method for detecting a mutation in the ALK2 gene region may be performed by various methods capable of detecting a mutation, in addition to the method of directly determining the nucleotide sequence of DNA or cDNA.

The detection of a mutation according to the present invention may also be performed by, for example, the following method. Specifically, a DNA or cDNA sample is first prepared from a biological sample. Subsequently, a reporter fluorescent dye- and quencher fluorescent dye-labeled oligonucleotide probe having a nucleotide sequence complementary to a nucleotide sequence containing the mutation in the ALK2 gene region is prepared. Then, the oligonucleotide probe is hybridized to the DNA sample under stringent conditions. The nucleotide sequence containing the mutation in the ALK2 gene region is further amplified using the DNA sample hybridized with the oligonucleotide probe as a template. Then, fluorescence (signals) emitted by the reporter fluorescent dye through the decomposition of the oligonucleotide probe associated with the amplification is detected. Subsequently, the detected fluorescence is compared with a control. Examples of such a method include double die probe method and TaqMan® probe method.

In an alternative method, a DNA or cDNA sample is prepared from a biological sample. Subsequently, the nucleotide sequence containing the mutation in the ALK2 gene region is amplified using the DNA sample as a template in a reaction system containing an intercalator that emits fluorescence upon insertion between two strands of DNA. Then, the temperature of the reaction system is changed, and variation in the intensity of the fluorescence emitted by the intercalator is detected. The detected variation in the intensity of the fluorescence caused by the change in the temperature is compared with a control. Examples of such a method include HRM (high resolution melting) method.

In a further alternative method, a DNA or cDNA sample is first prepared from the biological sample. Subsequently, DNA containing a mutation site in the ALK2 gene region is amplified. The amplified DNA is further cleaved with restriction enzymes, and the cleaved DNA fragments are separated according to their sizes. Then, the detected sizes of the DNA fragments are compared with a control. Examples of such a method include a method using restriction fragment length polymorphism (RFLP) and PCR-RFLP.

In a further alternative method, a DNA or cDNA sample is first prepared from a biological sample. Subsequently, DNA containing a mutation site in the ALK2 gene region is amplified. The amplified DNA is further dissociated into single-stranded DNAs, which are then separated on a non-denaturing gel. Subsequently, the mobility of the separated single-stranded DNAs on the gel is compared with a control. Examples of such a method include PCR-SSCP (single-strand conformation polymorphism).

In a further alternative method, a DNA or cDNA sample is first prepared from a biological sample. Subsequently, DNA containing a mutation site in the ALK2 gene region is amplified. Then, the amplified DNA is separated on a gel in which the concentration of a DNA denaturant is gradually elevated. Subsequently, the mobility of the separated DNA on the gel is compared with a control. Examples of such a method include denaturant gradient gel electrophoresis (DGGE).

A further alternative method is a method using DNA containing a mutation site in the ALK2 gene region prepared from the biological sample, and a substrate with immobilized oligonucleotide probes hybridizing to the DNA under stringent conditions. Examples of such a method include a DNA array method.

In a further alternative method, a DNA or cDNA sample is first prepared from the biological sample. Also, an "oligonucleotide primer having a nucleotide sequence complementary to a 3'-side nucleotide downstream by one nucleotide from the base at the mutation site in the ALK2 gene region and to a 3'-side nucleotide sequence downstream of the 3'-side nucleotide" is prepared. Subsequently, ddNTP primer extension reaction is performed using the DNA as a template and the primer. Subsequently, the primer extension reaction product is applied to a mass spectrometer to conduct mass spectrometry. Subsequently, the genotype is determined from the mass spectrometry results. The determined genotype is then compared with a control. Examples of such a method include MALDI-TOF/MS.

In a further alternative method, a DNA or cDNA sample is first prepared from a biological sample. Subsequently, an oligonucleotide probe consisting of 5'—(a nucleotide sequence complementary to the nucleotide at the mutation site in the ALK2 gene region and to a 5'-side nucleotide sequence upstream of the nucleotide)—(a nucleotide sequence that does not hybridize to 3'-side nucleotide downstream by one nucleotide from the mutation site in the ALK2 gene region and to a 3'-side nucleotide sequence downstream of the 3'-side nucleotide)—3' (i.e., flap) is prepared. Also, an "oligonucleotide probe having a nucleotide sequence complementary to the nucleotide at the mutation site in the ALK2 gene region, and to a 3'-side nucleotide sequence downstream of the nucleotide" is prepared. Subsequently, the prepared DNA is hybridized to the two types of oligonucleotide probes, and the hybridized DNA is cleaved with a single-stranded DNA-cleaving enzyme to release the flap. Examples of the single-stranded DNA-cleaving enzyme include, but are not particularly limited to, cleavase. In this method, a fluorescent reporter- and fluorescent quencher-labeled oligonucleotide probe having a sequence complementary to the flap is then hybridized to the flap. Subsequently, the intensity of the generated fluorescence is measured. Subsequently, the measured intensity of the fluorescence is compared with a control. Examples of such a method include the Invader method.

In a further alternative method, a DNA or cDNA sample is first prepared from a biological sample. Subsequently, DNA containing a mutation site in the ALK2 gene region is amplified. Then, the amplified DNA is dissociated into single strands, and only one of the single strands of the dissociated DNA is separated. Extension reaction is then performed one by one from a nucleotide in the vicinity of the nucleotide at the mutation site in the ALK2 gene region. Pyrophosphoric acid generated during this reaction is enzymatically allowed to develop light. The intensity of the light is measured. The measured intensity of the fluorescence is compared with a control. Examples of such a method include the Pyrosequencing method.

In a further alternative method, a DNA or cDNA sample is first prepared from a biological sample. Subsequently, DNA containing a mutation site in the ALK2 gene region is amplified. Then, an "oligonucleotide primer having a nucleotide sequence complementary to a 3'-side nucleotide downstream by one nucleotide from the nucleotide at the mutation site in the ALK2 gene region and to a 3'-side nucleotide sequence downstream of the 3'-side nucleotide" is prepared. Subsequently, single-base extension reaction is performed using the amplified DNA as a template and the prepared primer in the presence of fluorescently labeled nucleotides. Then, the degree of polarization of fluorescence is measured. The measured degree of polarization of fluorescence is compared with a control. Examples of such a method include the AcycloPrime method.

In a further alternative method, a DNA or cDNA sample is first prepared from a biological sample. Subsequently, DNA containing a mutation site in the ALK2 gene region is amplified. Then, an "oligonucleotide primer having a nucleotide sequence complementary to a 3'-side nucleotide downstream by one nucleotide from the nucleotide at the mutation site in the ALK2 gene region and to a 3'-side nucleotide sequence downstream of the 3'-side nucleotide" is prepared. Subsequently, single-nucleotide extension reaction is performed using the amplified DNA as a template and the prepared primer in the presence of fluorescently labeled nucleotides. Subsequently, the nucleotide species used in the single-nucleotide extension reaction are determined. Then, the determined nucleotide species are compared with a control. Examples of such a method include the SNuPE method.

The sample prepared from the above-mentioned biological sample may be a protein. In such a case, a method using a molecule (e.g., an antibody) specifically binding to a site having a change of amino acid caused by the mutation may be used for detecting the mutation.

4. Detection of Ectopic Ossification and/or Brain Tumor

Ectopic ossification and/or brain tumor is induced by ALK2-mediated BMP signal transduction.

The "ectopic ossification" means bone formation at a site where the bone is originally absent. Examples of the "ectopic ossification" may include fibrodysplasia ossificans progressiva (FOP) and progressive osseous heteroplasia (POH), though the ectopic ossification is not limited thereto as long as the ectopic ossification is induced by BMP signal transduction mediated by ALK2 having an active mutation.

The "brain tumor" means a tumor that develops in a tissue in the skull. Examples of the "brain tumor" may include diffuse intrinsic pontine glioma (DIPG), brain stem glioma, glioblastoma, glioblastoma multiforme (GBM), non-glioblastoma brain tumor, meningioma, central nervous system lymphoma, glioma, astroglioma, anaplastic astrocytoma, oligodendroglioma, oligoastrocytoma, medulloblastoma, and ependymoma, though the brain tumor is not limited thereto as long as the brain tumor is induced by BMP signal transduction mediated by ALK2 having an active mutation.

ALK2 is a transmembrane serine/threonine kinase receptor binding to BMP. ALK2 binds to BMP at the N-terminal extracellular region and activates a downstream intracellular signaling pathway through intracellular serine/threonine kinase. Bone morphogenetic protein (BMP) is a multifunctional growth factor belonging to the transforming growth factor 13 TGF-(3) superfamily, and approximately 20 BMP family members have been identified. BMP has been confirmed to induce ectopic bone formation in soft tissues including skeletal muscle tissues and is therefore considered to participate in diseases promoting abnormal bone formation. BMP-2 and BMP-4 are considered to have higher affinity for ALK3 than that for ALK2. Since ALK3 is expressed ubiquitously as compared with ALK2, BMP-2 or BMP-4 seems to be often used in general in experiments of inducing ectopic ossification at various sites. On the other hand, BMP-7 has relatively high affinity for ALK2. BMP-9 is generally considered to have high affinity for ALK1 and has also been found to have relatively high affinity for ALK2. In FOP, ectopic ossification occurs via ALK2. Therefore, the presence or absence of therapeutic and/or prophylactic effects on FOP may probably be confirmed by testing efficacy for ectopic osteoinduction caused by the activation of ALK2-mediated signals by BMP-7 and BMP-9.

The culture of myoblasts (C2C12 cells) in the presence of BMP suppresses their differentiation into mature muscle cells through an intracellular signal transduction mechanism specific for BMP and instead induces the differentiation into osteoblasts. Thus, ALK2-mediated BMP signal transduction may be analyzed with models of induction of differentiation of C2C12 cells into osteoblasts by BMP.

5. Production of Anti-ALK2 Antibody

The antibody used in the present invention against ALK2 may be obtained according to a method known in the art (e.g., Kohler and Milstein, Nature (1975) 256, p. 495-497; and Kennet, R. ed., Monoclonal Antibodies, p. 365-367, Plenum Press, N.Y. (1980)). Specifically, the monoclonal antibody may be obtained by fusing antibody-producing cells that produce the antibody against ALK2 with myeloma cells to establish hybridomas. The obtained antibody may be tested for its binding activity and cross-linking ability to ALK2 to select an antibody applicable to human diseases.

Herein, positions of amino acids assigned to CDR/FR characteristic of an antibody are laid out according to the KABAT numbering (KABAT et al., Sequences of Proteins of Immunological Interest, 5th Ed. Public Health Service National Institutes of Health, Bethesda, MD. (1991)).

The antibody used in the present invention includes monoclonal antibodies against ALK2 described above as well as, for example, polyclonal antibodies similarly having therapeutic and/or prophylactic effects, recombinant antibodies artificially engineered for the purpose of, for example, reducing heterogeneous antigenicity against humans, for example, chimeric antibodies, humanized antibodies, human antibodies, and the like. These antibodies may be produced by use of known methods.

Examples of the chimeric antibody may include chimeric antibodies comprising variable regions and constant regions (Fc) of antibodies derived from different species, for example, the variable regions of a mouse- or rat-derived antibody joined to human-derived constant regions (see Proc. Natl. Acad. Sci. U.S.A., 81, 6851-6855, (1984)).

Examples of the humanized antibody may include an antibody comprising CDRs alone integrated into a human-derived antibody (see Nature (1986) 321, p. 522-525), and an antibody comprising the CDR sequences as well as amino acid residues of a portion of frameworks grafted into a human antibody by a CDR grafting method (International Publication No. WO 90/07861).

Examples of the anti-ALK2 antibody that may be used in the present invention may include, but are not limited to, the following anti-ALK2 antibodies a comprising heavy chain variable region sequence and a light chain variable region sequence.

An anti-ALK2 antibody in which a heavy chain sequence of the anti-ALK2 antibody or the antigen-binding fragment thereof comprises a variable region having CDRH1, CDRH2, and CDRH3, wherein the CDRH1, the CDRH2, and the CDRH3 consist of the amino acid sequences of SEQ ID NO: 5, SEQ ID NO: 6, and SEQ ID NO: 7, respectively;
SEQ ID NO: 11, SEQ ID NO: 12, and SEQ ID NO: 13, respectively;
SEQ ID NO: 18, SEQ ID NO: 19, and SEQ ID NO: 20, respectively; or
SEQ ID NO: 24, SEQ ID NO: 25, and SEQ ID NO: 26, respectively, and a light chain sequence thereof comprises a variable region having CDRL1, CDRL2, and CDRL3, wherein the CDRL1, the CDRL2, and the CDRL3 consist of the amino acid sequences of SEQ ID NO: 8, SEQ ID NO: 9, and SEQ ID NO: 10, respectively;
SEQ ID NO: 8, SEQ ID NO: 17, and SEQ ID NO: 10, respectively;
SEQ ID NO: 14, SEQ ID NO: 15, and SEQ ID NO: 16, respectively;
SEQ ID NO: 21, SEQ ID NO: 22, and SEQ ID NO: 23, respectively; or
SEQ ID NO: 27, SEQ ID NO: 28, and SEQ ID NO: 29, respectively, and an antibody that competes, for binding to the ALK2, with the anti-ALK2 antibody, and has a property of cross-linking the ALK2 and a property of inhibiting BMP signal transduction.

Alternatively, an anti-ALK2 antibody in which the heavy chain variable region sequence of the anti-ALK2 antibody or the antigen-binding fragment thereof is:

a1) an amino acid sequence consisting of amino acid residues from position 20 to position 142 of the amino acid sequence of SEQ ID NO: 31;
a2) an amino acid sequence consisting of amino acid residues from position 20 to position 142 of the amino acid sequence of SEQ ID NO: 33;
a3) an amino acid sequence consisting of amino acid residues from position 20 to position 140 of the amino acid sequence of SEQ ID NO: 34;
a4) an amino acid sequence consisting of amino acid residues from position 20 to position 140 of the amino acid sequence of SEQ ID NO: 36;
a5) an amino acid sequence consisting of amino acid residues from position 20 to position 140 of the amino acid sequence of SEQ ID NO: 38;
a6) an amino acid sequence consisting of amino acid residues from position 20 to position 140 of the amino acid sequence of SEQ ID NO: 39;
a7) an amino acid sequence having at least 95% identity to any one amino acid sequence selected from the amino acid sequences a1) to a6);
a8) an amino acid sequence having at least 99% identity to any one amino acid sequence selected from the amino acid sequences a1) to a6); or
a9) an amino acid sequence comprising a substitution(s), a deletion(s), or an addition(s) of one or several amino acid residues in any one amino acid sequence selected from the amino acid sequences a1) to a6), and the light chain variable region sequence is
b1) an amino acid sequence consisting of amino acid residues from position 21 to position 133 of the amino acid sequence of SEQ ID NO: 32;
b2) an amino acid sequence consisting of amino acid residues from position 21 to position 129 of the amino acid sequence of SEQ ID NO: 35;
b3) an amino acid sequence consisting of amino acid residues from position 21 to position 129 of the amino acid sequence of SEQ ID NO: 37;
b4) an amino acid sequence having at least 95% identity to any one amino acid sequence selected from the amino acid sequences b1) to b3);
b5) an amino acid sequence having at least 99% identity to any one amino acid sequence selected from the amino acid sequences b1) to b3); or
b6) an amino acid sequence comprising a substitution(s), a deletion(s), or an addition(s) of one or several amino acid residues in any one amino acid sequence selected from the amino acid sequences b1) to b3), and an antibody that competes, for binding to the ALK2, with the anti-ALK2 antibody, and has a property of cross-linking the ALK2 and a property of inhibiting BMP signal transduction.

Further specifically, examples of the anti-ALK2 antibody that may be used in the present invention may include anti-ALK2 antibodies disclosed in WO 2016/121908 by the present inventors.

Examples of the rat anti-ALK2 antibody may include A2-11E, A2-15A, A2-25C, and A2-27D described in Example 1 of WO 2016/121908.

Examples of the human chimeric anti-ALK2 antibody may include cA2-15A and cA2-27D described in Example 5 of WO 2016/121908.

The humanized antibody derived from the A2-15A antibody is included in the antibody used in the present invention as long as the humanized antibody contains all of the 6 CDR sequences of A2-15A and has binding activity and cross-linking ability to ALK2. The heavy chain variable region of the A2-15A antibody comprises CDRH1 consisting of the amino acid sequence of SEQ ID NO: 5 (GFTFSHYYMA), CDRH2 consisting of the amino acid sequence of SEQ ID NO: 6 (SITNSGGSINYRDSVKG), and CDRH3 consisting of the amino acid sequence of SEQ ID NO: 7 (EGGENYGGYPPFAY). The light chain variable region of the A2-15A antibody comprises CDRL1 consisting of the amino acid sequence of SEQ ID NO: 8 (RANQGVSLSRYNLMH), CDRL2 consisting of the amino acid sequence of SEQ ID NO: 9 (RSSNLAS), and CDRL3 consisting of the amino acid sequence of SEQ ID NO: 10 (QQSRESPFT). Further, an antibody that competes, for binding to the ALK2, with the A2-15A antibody, and has a property of cross-linking the ALK2 and a property of inhibiting the BMP signal transduction is also included in the present invention.

The humanized antibody derived from the A2-27D antibody is included in the antibody used in the present invention as long as the humanized antibody contains all of the 6 CDR sequences of A2-27D and has binding activity and cross-linking ability to ALK2. The heavy chain variable region of the A2-27D antibody comprises CDRH1 consisting of the amino acid sequence of SEQ ID NO: 11 (GSTFSNYGMK), CDRH2 consisting of the amino acid sequence of SEQ ID NO: 12 (SISRSSTYIYYADTVKG), and CDRH3 consisting of the amino acid sequence of SEQ ID NO: 13 (AISTPFYWYFDF). The light chain variable region of the A2-27D antibody comprises CDRL1 consisting of the amino acid sequence of SEQ ID NO: 14 (LASSSVSYMT), CDRL2 consisting of the amino acid sequence of SEQ ID NO: 15 (GTSNLAS), and CDRL3 consisting of the amino acid sequence of SEQ ID NO: 16

(LHLTSYPPYT). Further, an antibody that competes, for binding to the ALK2, with the A2-27D antibody, and has a property of cross-linking the ALK2 and a property of inhibiting the BMP signal transduction is also included in the present invention.

The humanized antibody derived from the A2-11E antibody is included in the antibody used in the present invention as long as the humanized antibody contains all of the 6 CDR sequences of A2-11E and has binding activity and cross-linking ability to ALK2. The heavy chain variable region of the A2-11E antibody comprises CDRH1 consisting of the amino acid sequence of SEQ ID NO: 18 (GFTFSNYYMY), CDRH2 consisting of the amino acid sequence of SEQ ID NO: 19 (SINTDGGSTYYPDSVKG), and CDRH3 consisting of the amino acid sequence of SEQ ID NO: 20 (STPNIPLAY). The light chain variable region of the A2-11E antibody comprises CDRL1 consisting of the amino acid sequence of SEQ ID NO: 21 (KASQNIYKYLN), CDRL2 consisting of the amino acid sequence of SEQ ID NO: 22 (YSNSLQT), and CDRL3 consisting of the amino acid sequence of SEQ ID NO: 23 (FQYSSGPT). Further, an antibody that competes, for binding to the ALK2, with the A2-11E antibody, and has a property of cross-linking the ALK2 and a property of inhibiting the BMP signal transduction is also included therein.

The humanized antibody derived from the A2-25C antibody is included in the antibody used in the present invention as long as the humanized antibody contains all of the 6 CDR sequences of A2-25C and has binding activity and cross-linking ability to ALK2. The heavy chain variable region of the A2-25C antibody comprises CDRH1 consisting of the amino acid sequence of SEQ ID NO: 24 (GFTFSYYAMS), CDRH2 consisting of the amino acid sequence of SEQ ID NO: 25 (SISRGGDNTYYRDTVKG), and CDRH3 consisting of the amino acid sequence of SEQ ID NO: 26 (LNYNNYFDY). The light chain variable region of the A2-25C antibody comprises CDRL1 consisting of the amino acid sequence of SEQ ID NO: 27 (QASQDIGNWLS), CDRL2 consisting of the amino acid sequence of SEQ ID NO: 28 (GATSLAD), and CDRL3 consisting of the amino acid sequence of SEQ ID NO: 29 (LQAYSAPFT). Further, an antibody that competes, for binding to the ALK2, with the A2-25C antibody, and has a property of cross-linking the ALK2 and a property of inhibiting the BMP signal transduction is also included in the present invention.

A CDR-modified humanized antibody prepared by substitution of 1 to 3 amino acid residues in each CDR by other amino acid residues is also included in the antibody used in the present invention as long as the humanized antibody has binding activity and cross-linking ability to ALK2. Examples of the amino acid substitution in CDRL2 may include the substitution of one amino acid of CDRL2 in the amino acid sequence of SEQ ID NO: 30 (humanized hA2-15A-L4). CDRL2 consisting of the amino acid sequence of SEQ ID NO: 17 (RSSNLAQ) is preferred.

Actual examples of the humanized antibody derived from the A2-15A antibody may include:

an antibody consisting of a heavy chain comprising a heavy chain variable region sequence consisting of amino acid residues from position 20 to position 142 of the amino acid sequence of SEQ ID NO: 31 (humanized hA2-15A-H4) and a light chain comprising a light chain variable region sequence consisting of amino acid residues from position 21 to position 133 of the amino acid sequence of SEQ ID NO: 32 (humanized hA2-15A-L6), and an antibody consisting of a heavy chain comprising a heavy chain variable region sequence consisting of amino acid residues from position 20 to position 142 of the amino acid sequence of SEQ ID NO: 33 (humanized hA2-15A-H4 IgG2) and a light chain comprising a light chain variable region sequence consisting of amino acid residues from position 21 to position 133 of the amino acid sequence of SEQ ID NO: 32, and an antibody that competes, for binding to the ALK2, with any of the A2-15A antibodies, and has a property of cross-linking the ALK2 and a property of inhibiting the BMP signal transduction is also included in the present invention.

Preferred examples of the combination may include:

an antibody consisting of a heavy chain comprising an amino acid sequence consisting of amino acid residues from position 20 to 472 of the amino acid sequence of SEQ ID NO: 31 and a light chain comprising an amino acid sequence consisting of amino acid residues from position 21 to position 238 of the amino acid sequence of SEQ ID NO: 32, and an antibody consisting of a heavy chain comprising an amino acid sequence consisting of amino acid residues from position 20 to position 468 of the amino acid sequence of SEQ ID NO: 33 and a light chain comprising an amino acid sequence consisting of amino acid residues from position 21 to position 238 of the amino acid sequence of SEQ ID NO: 32, and an antibody that competes, for binding to the ALK2, with any of the antibodies, and has a property of cross-linking the ALK2 and a property of inhibiting the BMP signal transduction is also included therein.

Actual examples of the humanized antibody derived from the A2-27D antibody may include:

an antibody consisting of a heavy chain comprising a heavy chain variable region sequence consisting of amino acid residues from position 20 to position 140 of the amino acid sequence of SEQ ID NO: 34 (humanized hA2-27D-H2) and a light chain comprising a light chain variable region sequence consisting of amino acid residues from position 21 to position 129 of the amino acid sequence of SEQ ID NO: 35 (humanized hA2-27D-L2);

an antibody consisting of a heavy chain comprising a heavy chain variable region sequence consisting of amino acid residues from position 20 to position 140 of the amino acid sequence of SEQ ID NO: 36 (humanized hA2-27D-H3) and a light chain comprising a light chain variable region sequence consisting of amino acid residues from position 21 to position 129 of the amino acid sequence of SEQ ID NO: 37 (humanized hA2-27D-L4);

an antibody consisting of a heavy chain comprising a heavy chain variable region sequence consisting of amino acid residues from position 20 to position 140 of the amino acid sequence of SEQ ID NO: 38 (humanized hA2-27D-H2-LALA) and a light chain comprising a light chain variable region sequence consisting of amino acid residues from position 21 to position 129 of the amino acid sequence of SEQ ID NO: 35; and an antibody consisting of a heavy chain comprising a heavy chain variable region sequence consisting of amino acid residues from position 20 to position 140 of the amino acid sequence of SEQ ID NO: 39 (humanized hA2-27D-H3-LALA) and a light chain comprising a light chain variable region sequence consisting of amino acid residues from position 21 to position 129 of the amino acid sequence of SEQ ID NO: 37; and an antibody that competes, for binding to the ALK2, with any of the antibodies, and has a property of cross-linking the ALK2 and a property of inhibiting the BMP signal transduction is also included in the present invention.

Preferred examples of the combination may include:

an antibody consisting of a heavy chain comprising an amino acid sequence consisting of amino acid residues from position 20 to position 470 of the amino acid sequence of SEQ ID NO: 34 and a light chain comprising an amino acid sequence consisting of amino acid residues from position 21 to position 234 of the amino acid sequence of SEQ ID NO: 35;

an antibody consisting of a heavy chain comprising an amino acid sequence consisting of amino acid residues from position 20 to position 470 of the amino acid sequence of SEQ ID NO: 36 and a light chain comprising an amino acid sequence consisting of amino acid residues from position 21 to position 234 of the amino acid sequence of SEQ ID NO: 37;

an antibody consisting of a heavy chain comprising an amino acid sequence consisting of amino acid residues from position 20 to position 470 of the amino acid sequence of SEQ ID NO: 38 and a light chain comprising an amino acid sequence consisting of amino acid residues from position 21 to position 234 of the amino acid sequence of SEQ ID NO: 35; and an antibody consisting of a heavy chain comprising an amino acid sequence consisting of amino acid residues from position 20 to position 470 of the amino acid sequence of SEQ ID NO: 39 and a light chain comprising an amino acid sequence consisting of amino acid residues from position 21 to position 234 of the amino acid sequence of SEQ ID NO: 37;and an antibody that competes, for binding to the ALK2, with any of the antibodies, and has a property of cross-linking the ALK2 and a property of inhibiting the BMP signal transduction is also included in the present invention.

Further examples of the antibody used in the present invention may include a human antibody. The anti-ALK2 human antibody means a human antibody produced from only human chromosome-derived antibody gene sequences. The anti-ALK2 human antibody may be obtained by a method using human antibody-producing mice carrying human chromosome fragments that comprise human antibody heavy and light chain genes (see e.g., Tomizuka, K. et al., Nature Genetics (1997), 16, p. 133-143; Kuroiwa, Y. et al., Nuc. Acids Res. (1998), 26, p. 3447-3448; Yoshida, H. et al., Animal Cell Technology: Basic and Applied Aspects vol. 10, p. 69-73 Kitagawa, Y., Matsuda, T. and Iijima, S. eds.), Kluwer Academic Publishers, 1999; and Tomizuka, K. et al., Proc. Natl. Acad. Sci. USA (2000), 97, p. 722-727).

Specifically, such a human antibody-producing mouse may be created as a recombinant animal in which the endogenous immunoglobulin heavy and light chain gene loci have been disrupted and instead human immunoglobulin heavy and light chain gene loci are integrated via a vector, for example, a human artificial chromosome (HAC) vector or a mouse artificial chromosome (MAC) vector, by preparing a knockout animal or a transgenic animal or by crossing these animals.

Alternatively, eukaryotic cells may be transformed with cDNAs encoding the heavy and light chains, respectively, of such a human antibody, preferably with vectors comprising the cDNAs, by gene recombination techniques. The transformed cells producing a recombinant human monoclonal antibody may be cultured to obtain this antibody from the culture supernatant. In this context, for example, eukaryotic cells, preferably mammalian cells such as CHO cells, lymphocytes, or myeloma cells, may be used as hosts.

Also, a method for obtaining a phage display-derived human antibody selected from a human antibody library (see e.g., Wormstone, I. M. et al., Investigative Ophthalmology & Visual Science (2002), 43 (7), p. 2301-2308; Carmen, S. et al., Briefings in Functional Genomics and Proteomics (2002), 1 (2), p. 189-203; and Siriwardena, D. et al., Ophthalmology (2002), 109 (3), p. 427-431) is known.

For example, a phage display method (Nature Biotechnology (2005), 23, (9), p. 1105-1116) may be used, which involves allowing the variable regions of a human antibody to be expressed as single-chain Fv (scFv) on phage surface and selecting a phage binding to the antigen. The phage selected on the basis of its ability to bind to the antigen may be subjected to gene analysis to determine DNA sequences encoding the variable regions of the human antibody binding to the antigen. If the DNA sequence of scFv binding to the antigen is determined, an expression vector having this sequence may be prepared and transferred to appropriate hosts, followed by expression to obtain the human antibody (WO 92/01047, WO 92/20791, WO 93/06213, WO 93/11236, WO 93/19172, WO 95/01438, WO 95/15388, Annu. Rev. Immunol (1994), 12, p. 433-455; and Nature Biotechnology (2005), 23 (9), p. 1105-1116).

Antibodies binding to the same epitope as that for an anti-ALK2 antibody disclosed in WO 2016/121908 are also included in the anti-ALK2 antibody that may be used in the present invention. Examples thereof include antibodies binding to the same epitope as that for the A2-11E antibody, the A2-15A antibody, the A2-25C antibody, and/or the A2-27D antibody.

When an antibody binds to or recognizes a partial conformation of an antigen, the epitope for this antibody may be determined by identifying amino acid residues on the antigen adjacent to the antibody by use of X-ray structure analysis. For example, the antibody or a fragment thereof and the antigen or a fragment thereof may be bound to each other, crystallized, and structurally analyzed to identify amino acid residues on the antigen having an interaction distance between the amino acid residue and the antibody. The interaction distance is 8 angstroms or smaller, preferably 6 angstroms or smaller, more preferably 4 angstroms or smaller. One or more amino acid residues having such an interaction distance with the antibody may constitute an epitope (or an antigenic determinant) for the antibody. When the number of such amino acid residues is two or more, these amino acids may not be adjacent to each other on the primary sequence.

Examples of the antibody or an antigen-binding fragment thereof binding to the epitope of the ALK2 protein are as described below.

The anti-ALK2 antibody or the antigen-binding fragment thereof may specifically bind to a polypeptide consisting of amino acid residues from position 21 to position 123 in the amino acid sequence (SEQ ID NO: 1) of human ALK2.

The A2-27D antibody recognizes a partial conformation on human ALK2. In the amino acid sequence (SEQ ID NO: 1) of human ALK2, the amino acid residues having an interaction distance with the A2-27D antibody, i.e., the epitope, is constituted by each of the residues of glutamic acid (Glu) at position 38, glycine (Gly) at position 39, isoleucine (Ile) at position 59, asparagine (Asn) at position 60, aspartic acid (Asp) at position 61, glycine (Gly) at position 62, phenylalanine (Phe) at position 63, histidine (His) at position 64, valine (Val) at position 65, tyrosine (Tyr) at position 66, asparagine (Asn) at position 102, threonine (Thr) at position 104, glutamine (Gln) at position 106, and leucine (Leu) at position 107. The antibody, an antigen-binding fragment thereof, or a modified form of the antibody or the fragment which binds to this epitope or has an interaction distance between the antibody or the fragment and each of the amino acid residues are also encompassed in the antibody used in the present invention.

The A2-25C antibody recognizes a partial conformation on human ALK2. In the amino acid sequence (SEQ ID NO: 1) of human ALK2, the amino acid residues having an interaction distance with the A2-25C antibody, i.e., the epitope, is constituted by each of the residues of glutamic acid (Glu) at position 38, glycine (Gly) at position 39, leucine (Leu) at position 40, isoleucine (Ile) at position 59, asparagine (Asn) at position 60, aspartic acid (Asp) at position 61, glycine (Gly) at position 62, phenylalanine (Phe) at position 63, histidine (His) at position 64, valine (Val) at position 65, tyrosine (Tyr) at position 66, and threonine (Thr) at position 104. The antibody, an antigen-binding fragment thereof, or a modified form of the antibody or the fragment which binds to this epitope or has an interaction distance with these amino acid residues are also encompassed in the antibody used in the present invention.

Alternatively, the anti-ALK2 antibody or the antigen-binding fragment thereof may be an antibody or an antigen-binding fragment thereof that competes, for binding to ALK2, with the anti-ALK2 antibody or the antigen-binding fragment thereof described above (e.g., the A2-27D antibody and the A2-25C antibody).

The antibody described above may be evaluated for its binding activity to the antigen by, for example, a method described in Example 2, 6, 9, or 10 of WO 2016/121908 to select suitable antibodies. The dissociation constant ($K_D$) of the antibody is, for example, $1 \times 10^{-6}$ to $1 \times 10^{-12}$ M or less, but is not limited to this range as long as the therapeutic or prophylactic effects of interest are obtained. The dissociation constant of the antibody for the antigen (ALK2) may be measured using Biacore T200 GE Healthcare Bio-Sciences Corp.) based on surface plasmon resonance (SPR) as detection principles. For example, the antibody set to an appropriate concentration is reacted as an analyte with the antigen immobilized as a ligand on a solid phase. The association and dissociation between the antibody and the antigen may be measured to obtain an association rate constant ka1, a dissociation rate constant kd1, and a dissociation constant ($K_D$; $K_D$=kd1/ka1). The evaluation of binding activity to ALK2 is not limited to use of Biacore T200 and may be conducted using, for example, an instrument based on surface plasmon resonance (SPR) as detection principles, KinExA (Sapidyne Instruments Inc.) based on kinetic exclusion assay as detection principles, BLItz system (Pall Corp.) based on bio-layer interferometry as detection principles, or ELISA (enzyme-linked immunosorbent assay).

The antibody described above may be evaluated for its cross-linking ability to the antigen by, for example, a method described in Example 4 mentioned later to select suitable antibodies. Specifically, a fusion body of ALK2 and LgBiT or SmBiT is expressed in in vitro cells using NanoLuc® Binary Technology: NanoBiT® (Promega Corp.), and the interaction of the ALK2 protein with the antibody may be detected from luminescence brought about by structural complementarity of LgBiT and SmBiT.

One example of another indicator for comparing the properties of antibodies may include the stability of the antibodies. Differential scanning calorimetry (DSC) is a method that may rapidly and accurately measure a transition midpoint (Tm), which serves as a good indicator for the relative structural stability of proteins. Tm values may be measured using DSC and compared to determine difference in thermal stability. The preservation stability of an antibody is known to correlate with the thermal stability of the antibody to some extent (Lori Burton, et al., Pharmaceutical Development and Technology (2007) 12, p. 265-273). A suitable antibody may be selected using its thermal stability as an indicator. Examples of other indicators for selecting the antibody may include high yields in appropriate host cells and low aggregation in an aqueous solution. For example, an antibody having the highest yield does not always exhibit the highest thermal stability. Therefore, it is necessary to select an antibody most suitable for administration to humans by comprehensive judgment based on the indicators mentioned above.

A method for obtaining a single-chain immunoglobulin by linking the full-length sequences of antibody heavy and light chains via an appropriate linker is also known (Lee, H-S, et al., Molecular Immunology (1999) 36, p. 61-71; and Shirrmann, T. et al., mAbs (2010), 2, (1) p. 1-4). Such single-chain immunoglobulins may be dimerized to retain a structure and activity similar to those of antibodies which are originally tetramers. Alternatively, the antibody used in the present invention may be an antibody that has a single heavy chain variable region and lacks a light chain sequence. Such an antibody, which is called a single-domain antibody (sdAb), a nanobody, or an antibody of Camelidae family (heavy chain antibody), has actually been observed in camels or llamas and reported to have an ability to bind to an antigen (Muyldemans S. et al., Protein Eng. (1994) 7 (9), 1129-35; and Hamers-Casterman C. et al., Nature (1993) 363 (6428) 446-8). These antibodies may also be interpreted as an antigen-binding fragment of the antibody according to the present invention.

The antibody-dependent cellular cytotoxic activity of the antibody used in the present invention may be enhanced by controlling the modification of the sugar chain bound with the antibody. For example, methods described in WO 99/54342, WO 2000/61739, and WO 2002/31140 are known as such a technique of controlling the sugar chain modification of the antibody, though this technique is not limited thereto.

In the case of preparing an antibody by isolating the antibody genes and then transferring the genes to an appropriate host, the appropriate host may be used in combination with an expression vector.

Specific examples of the antibody genes may include a gene (or a polynucleotide) encoding a heavy chain sequence and a gene (or a polynucleotide) encoding a light chain sequence of the antibody as described in WO 2016/121908, and a combination of these genes (or polynucleotides).

For the transformation of host cells, a heavy chain sequence gene (or polynucleotide) and a light chain sequence gene (or polynucleotide) may be inserted in a same expression vector or may be inserted in distinct expression vectors. When eukaryotic cells are used as hosts, animal cells, plant cells, or eukaryotic microorganisms may be used. Examples of the animal cells may include mammalian cells, for example, simian COS cells (Gluzman, Y., Cell (1981) 23, p. 175-182, ATCC CRL-1650), mouse fibroblast NIH3T3 (ATCC No. CRL-1658), and dihydrofolate reductase-deficient cell lines (Urlaub, G. and Chasin, L. A., Proc. Natl. Acad. Sci. U.S.A. (1980) 77, p. 4126-4220) of Chinese hamster ovary cells (CHO cells, ATCC CCL-61). In the case of using prokaryotic cells, examples thereof may include *E. coli* and *Bacillus subtilis*. The antibody gene of interest is transferred to these cells by transformation, and the transformed cells are cultured in vitro to obtain antibodies. Such culture methods may differ in yield depending on the sequences of the antibodies. An antibody that is easy to produce as a drug may be selected using its yield as an indicator from among antibodies having equivalent binding activity.

The isotype of the antibody used in the present invention may be any isotype having an ability to cross-link ALK2. Examples thereof may include, but are not limited to, IgGs (IgG1, IgG2, IgG3, and IgG4), IgM, IgAs (IgA1 and IgA2), IgD, and IgE. Preferred examples of the isotypes may include IgG and IgM, more preferably IgG1, IgG2, and IgG4.

When IgG1 is used as an isotype of the antibody used in the present invention, the effector functions may be controlled by substituting a part of amino acid residues in constant regions (see WO 88/07089, WO 94/28027, and WO9 4/29351). Examples of such variants of IgG1 include IgG1 LALA (IgG1-L234A, L235A) and IgG1 LAGA (IgG1-L235A, G237A). IgG1 LALA is preferred.

When IgG4 is used as an isotype of the antibody used in the present invention, splitting unique to IgG4 can be suppressed to extend the half-life by substituting a part of amino acid residues in constant regions (see Molecular Immunology, 30, 1 105-108 (1993)). An example of such mutant of IgG4 includes IgG4 pro (IgG4-S241P).

The antibody used in the present invention may be an antigen-binding fragment of the antibody having antigen-binding sites, or a modified form of the antibody. The fragment of the antibody may be obtained by treating the antibody with a proteolytic enzyme such as papain or pepsin or by expressing a genetically engineered antibody gene in appropriate cultured cells. Among such antibody fragments, a fragment that maintains the whole or a portion of the functions possessed by the full-length molecule of the antibody can be referred to as an antigen-binding fragment of the antibody. Examples of the functions of the antibody may generally include an antigen binding activity, an activity of inhibiting the activity of the antigen, an activity of enhancing the activity of the antigen, an antibody-dependent cellular cytotoxic activity, a complement-dependent cytotoxic activity, and a complement-dependent cellular cytotoxic activity. The function possessed by the antigen-binding fragment of the antibody according to the present invention is an activity to bind ALK2 and an ability to cross-link ALK2. The binding activity to ALK2 is antibody's or antigen-binding fragment's property of (preferably, specifically) binding to the ALK2 molecule, and is preferably an activity of inhibiting the activity of ALK2, more preferably an activity of inhibiting ALK2-mediated BMP signal transduction, most preferably an activity of suppressing, mitigating or causing the regression of ectopic ossification and/or brain tumor.

Examples of the fragment of the antibody may include F(ab')$_2$ and the like.

The antibody used in the present invention may have enhanced affinity for an antigen by multimerization. A single antibody may be multimerized, or a plurality of antibodies recognizing a plurality of epitopes, respectively, of the same antigen may be multimerized. Examples of a method for multimerizing these antibodies may include the binding of two scFvs to an IgG CH3 domain, the binding to streptavidin, and the introduction of a helix-turn-helix motif.

The antibody used in the present invention may be a polyclonal antibody which is a mixture of plural types of anti-ALK2 antibodies, whose amino acid sequences are different from one another. An example of the polyclonal antibody may include a mixture of plural types of antibodies that are different in CDRs. An antibody obtained by culturing a mixture of cells that produce different antibodies, followed by purification from the cultures, may be used as such a polyclonal antibody (see WO 2004/061104).

The antibody used in the present invention may be an antibody having 80% to 99% identity when compared with the heavy and/or light chains of the antibody. In this context, the term "identity" has general definition used in the art. The % identity refers to the percentage of the number of identical amino acids relative to the total number of amino acids (including gaps) when two amino acid sequences are aligned so as to give the largest consistency of amino acids. Antibodies that have an ability to bind to the antigen, an inhibitory effect on BMP signal transduction, and cross-linking ability at analogous levels to the antibodies described above may be selected by combining sequences that exhibit high identity to the amino acid sequences of the heavy and light chains. Such identity is generally 80% or 85% or higher identity, preferably 90% or higher, 91% or higher, 92% or higher, 93% or higher or 94% or higher identity, more preferably 95% or higher, 96% or higher, 97% or higher or 98% or higher identity, most preferably 99% or higher identity. Alternatively, antibodies that have various effects equivalent to the antibodies described above may be selected by combining amino acid sequences that comprise a substitution(s), a deletion(s), and/or an addition(s) of one or several amino acid residues in the amino acid sequences of the heavy and/or light chains. The number of amino acid residues to be substituted, deleted, and/or added is generally 10 or less amino acid residues, preferably 5 or 6 or less amino acid residues, more preferably two or three or less amino acid residues, most preferably one amino acid residue.

The heavy chain of an antibody produced by cultured mammalian cells is known to lack a carboxyl-terminal lysine residue (Journal of Chromatography A, 705: 129-134 (1995)). Also, the heavy chain of such an antibody is known to lack two carboxyl-terminal amino acid residues (glycine and lysine) and instead have an amidated proline residue at the carboxy terminus (Analytical Biochemistry, 360: 75-83 (2007)).

An N-terminal glutamine or glutamic acid residue in the heavy or light chain of an antibody is known to be modified by pyroglutamylation during preparation of the antibody, and the antibody used in the present invention may have such a modification (WO 2013/147153).

Such deletion in the heavy chain sequence or modification in the heavy or light chain sequence does not influence the ability of the antibody to bind to the antigen and its effector functions (complement activation, antibody-dependent cytotoxic effects, etc.).

Thus, the antibody used in the present invention also encompasses an antibody that has received the deletion or the modification. Examples thereof may include a deletion variant derived from a heavy chain by the deletion of one or two amino acids at its carboxyl terminus, an amidated form of the deletion variant (e.g., a heavy chain having an amidated proline residue at the carboxyl-terminal site), and an antibody having a pyroglutamylated N-terminal amino acid residue in a heavy or light chain thereof. However, the deletion variant at the carboxyl terminus of the antibody heavy chain used in the present invention is not limited to the types described above as long as the deletion variant maintains the ability to bind to the antigen and the effector functions. Two heavy chains constituting the antibody used in the present invention may be heavy chains of any one type selected from the group consisting of the full-length heavy chain and the deletion variants described above, or may be a combination of heavy chains of any two types selected therefrom. The quantitative ratio of each deletion variant may be influenced by the type of cultured mammalian cells producing the antibody according to the present invention, and culture conditions. Examples of such a case may include the deletion of one carboxyl-terminal amino acid residue each in both the two heavy chains as main components of the antibody.

The identity between two types of amino acid sequences may be determined using the default parameters of Blast algorithm version 2.2.2 Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm is also available by access to www.ncbi.nlm.nih.gov/blast on the Internet. Two types of percentage values, Identity (or Identities) and Positivity (or Positivities), are calculated according to the Blast algorithm. The former is a value that indicates identical amino acid residues between two types of amino acid sequences that the identity should be determined. The latter is a numerical value determined by also taking into consideration similar amino acid residues in terms of their chemical structures. Herein, the value of identity is defined as the value of "Identity" when amino acid residues are identical between the amino acid sequences.

An antibody conjugated with any of various molecules such as polyethylene glycol (PEG) may also be used as a modified form of the antibody.

The antibody used in the present invention may further be any of conjugates formed by these antibodies with other drugs (immunoconjugates). Examples of such an antibody may include the antibody conjugated with a radioactive material or a compound having a pharmacological effect (Nature Biotechnology (2005) 23, p. 1137-1146).

The obtained antibodies may be purified until becoming homogeneous. Protein separation and purification methods conventionally used may be used for the separation and purification of the antibodies. The antibodies may be separated and purified by appropriately selected or combined approaches, for example, column chromatography, filtration through a filter, ultrafiltration, salting-out, dialysis, preparative polyacrylamide gel electrophoresis, and/or isoelectric focusing (Strategies for Protein Purification and Characterization: A Laboratory Course Manual, Daniel R. Marshak et al. eds., Cold Spring Harbor Laboratory Press (1996); and Antibodies: A Laboratory Manual. Ed Harlow and David Lane, Cold Spring Harbor Laboratory (1988)), though the separation and purification method is not limited thereto.

Examples of the chromatography may include affinity chromatography, ion-exchange chromatography, hydrophobic chromatography, gel filtration chromatography, reverse-phase chromatography, and adsorption chromatography.

These chromatography approaches may be carried out using liquid chromatography such as HPLC or FPLC.

Examples of the column for use in the affinity chromatography may include protein A columns and protein G columns.

Examples of the protein A columns may include Hyper D, POROS, and Sepharose F. F. (GE Healthcare Bio-Sciences Corp.).

Also, the antibody may be purified by exploiting its binding activity to the antigen using an antigen-immobilized carrier.

The $K_D$ value that indicates the binding affinity of the anti-ALK2 antibody according to the present invention for ALK2 is preferably $10^{-6}$ M or less, for example, $10^{-7}$ M or less, $10^{-8}$ M or less, $10^{-9}$ M or less, $10^{-10}$ M or less, $10^{-11}$ M or less, or $10^{-12}$ M or less.

6. Method for Treating Ectopic Ossification and/or Brain Tumor and Pharmaceutical Composition for Use in the Method The present invention provides a method for treating and/or preventing a disease caused by an active mutation in ALK2, comprising using a biological sample from a patient, detecting the presence or absence of the active mutation in ALK2 in the biological sample, and administering an anti-ALK2 antibody to a patient having the active mutation in ALK2 and having no mutation of an amino acid residue at position 330 proline residue in the human ALK2 sequence). Examples of the disease caused by an active mutation in ALK2 may include fibrodysplasia ossificans progressiva (FOP), progressive osseous heteroplasia (POH), traumatic ectopic ossification, ectopic ossification after implant arthroplasty, diffuse intrinsic pontine glioma (DIPG), spondyloarthritis (SpA), ankylosing spondylitis (AS), anemia, and thinning hair. The disease is preferably fibrodysplasia ossificans progressiva (FOP), progressive osseous heteroplasia (POH), traumatic ectopic ossification, or ectopic ossification after implant arthroplasty, more preferably fibrodysplasia ossificans progressiva (FOP), though the disease is not limited thereto as long as the disease is caused by an active mutation in ALK2. In FOP patients, finger or toe fusion or deformity, cervical fusion or deformity, or the like is also found, and hearing loss is also manifested. These conditions are also included in the disease caused by an active mutation in ALK2.

The present invention also provides a pharmaceutical composition for use in a method for treating and/or preventing a patient having ectopic ossification, wherein the patient has an active mutation in ALK2 protein which is responsible for ectopic ossification; an amino acid residue at position 330 of the ALK2 is proline; and an active ingredient of the composition is an anti-ALK2 antibody or an antigen-binding fragment thereof comprising a property of binding to the ALK2, a property of cross-linking the ALK2, and a property of inhibiting BMP signal transduction.

In an embodiment, the method comprises the steps of: (a) detecting the presence or absence of an active mutation in ALK2 in patients; (b) selecting a patient having the active mutation in ALK2; c) confirming that the patient has no mutation of an amino acid residue at position 330 of ALK2; and (d) administering the anti-ALK2 antibody or the antigen-binding fragment thereof to the selected patient.

In another embodiment, the step (c) further comprises the step of confirming that the ALK2 of the patient has no G328V mutation.

In a further alternative embodiment, the selection of the patient to which the anti-ALK2 antibody or the antigen-binding fragment thereof is to be administered comprises the steps of: (a) detecting the presence or absence of an active mutation in ALK2 in ectopic ossification patients; (b) selecting a patient having the active mutation in ALK2; and (c) excluding a patient having a mutation of an amino acid residue at position 330 of ALK2.

In another embodiment, the step (c) further comprises the step of excluding a patient having G328V mutation in ALK2.

Examples of the "ectopic ossification" according to the present invention may include fibrodysplasia ossificans progressiva (FOP). Fibrodysplasia ossificans progressiva (FOP) is preferred.

Active mutations in ALK2 have been confirmed in all FOP patients, and 10 or more types of mutations have been reported so far. All of these mutations have been found to be amino acid mutations (missense mutations) present in the intracellular region of the ALK2 protein and do not cause any change in the amino acid sequence of the extracellular region. Thus, use of the anti-ALK2 antibody binding to the extracellular region of ALK2 produces therapeutic and/or prophylactic effects on FOP, irrespective of the types of mutations.

The treatment of FOP means cure of FOP symptoms, amelioration of the symptoms, mitigation of the symptoms, or suppression of progression of the symptoms.

The prevention of FOP means circumvention or suppression of onset of flare-up or ectopic ossification.

Alternatively, the present invention provides a method for treating and/or preventing brain tumor, comprising using a biological sample derived from a patient, detecting the presence or absence of an active mutation in ALK2 in the biological sample, and administering an anti-ALK2 antibody to a patient having the active mutation other than G328V mutation in ALK2.

The present invention further provides a pharmaceutical composition for use in a method for treating and/or preventing a patient having brain tumor, wherein the patient has an active mutation in ALK2 protein which is responsible for brain tumor; and an active ingredient of the composition is an anti-ALK2 antibody or an antigen-binding fragment thereof comprising a property of binding to the ALK2, a property of cross-linking the ALK2, and a property of inhibiting BMP signal transduction.

Examples of the "brain tumor" according to the present invention may include diffuse intrinsic pontine glioma (DIPG), brain stem glioma, glioblastoma, glioblastoma multiforme (GBM), non-glioblastoma brain tumor, meningioma, central nervous system lymphoma, glioma, astroglioma, anaplastic astrocytoma, oligodendroglioma, oligoastrocytoma, medulloblastoma, and ependymoma. Diffuse intrinsic pontine glioma (DIPG) is preferred.

Active mutations in ALK2 have also been confirmed in DIPG patients. R206H, R258G, G328E, G328V, G328W, and G356D mutants are known as mutants of human ALK2. These mutations, except for the G328V mutation, are also common in FOP patients. The anti-ALK2 antibody exhibits ALK2 inhibitory activity except that the G328V mutation is present. Therefore, the anti-ALK2 antibody used in the present invention has therapeutic and/or prophylactic effects on DIPG in a patient having an active mutation other than G328V mutation in ALK2.

The inhibition of the biological activity of ALK2 (BMP signal inhibitory activity) with the anti-ALK2 antibody may be confirmed in vitro, for example, by luciferase assay using reporter plasmids having an insert of a BMP-responsive sequence, SMAD1/5/8 phosphorylation, expression analysis of BMP target genes, or measurement of alkaline phosphatase activity in mouse myoblasts C2C12 induced to differentiate into osteoblasts by stimulation with a BMP ligand.

The therapeutic or prophylactic effects of the anti-ALK2 antibody on ectopic ossification may be confirmed in vivo using laboratory animals, for example, by subcutaneously or intravenously administering the anti-ALK2 antibody to ectopic ossification-induced models with BMP ligand-containing pellets transplanted to mouse muscle, or FOP mouse models harboring mutated ALK2, and analyzing ectopic bone formation. Alternatively, the therapeutic or prophylactic effects on brain tumor may be confirmed, for example, by subcutaneously or intravenously administering the anti-ALK2 antibody to models prepared by the administration of patient-derived tumor cells to the brain or under the skin of immunodeficient mice, and analyzing tumor growth or the number of days of survival of the mice.

In the method of the present invention, the patient to be treated or prevented is a patient having an active mutation in ALK2, the patient having no mutation of an amino acid residue at position 330 of ALK2 the patient having proline at position 330) or the patient having no G328V mutation (the patient having no substitution of an amino acid residue at position 328 by valine), preferably a patient having no mutation of an amino acid residue at position 330 of ALK2 and having an active mutation other than G328V mutation in ALK2. Examples of the active mutation in ALK2 include L196P, delP197_F198insL (also referred to as "PF-197-8L"), R202I, R206H, Q207E, R258S, R258G, G325A, G328E, G328R, G328W, G356D, and R375P, though the mutation is not limited thereto as long as the mutation activates ALK2.

The anti-ALK2 antibody used in the present invention may be administered alone or in combination with at least one additional therapeutic drug for ectopic ossification in the treatment or prevention of ectopic ossification, and can be administered alone or in combination with at least one additional therapeutic drug for brain tumor, radiotherapy, immunotherapy or chemotherapy, etc. in the treatment or prevention of brain tumor.

Examples of the additional therapeutic drug for ectopic ossification that may be administered in combination with the anti-ALK2 antibody may include, but are not limited to, anti-inflammatory drugs, steroids, bisphosphonates, muscle relaxants, and retinoic acid receptor (RAR) γ agonists.

Examples of the anti-inflammatory drug may include aspirin, diclofenac, indomethacin, ibuprofen, ketoprofen, naproxen, piroxicam, rofecoxib, celecoxib, azathioprine, penicillamine, methotrexate, sulfasalazine, leflunomide, infliximab, and etanercept. Indomethacin, ibuprofen, piroxicam, or celecoxib is preferred.

Examples of the steroid may include prednisolone, beclomethasone, betamethasone, fluticasone, dexamethasone, and hydrocortisone. Prednisolone is preferred.

Examples of the bisphosphonate may include alendronate, cimadronate, clodronate, etidronate, ibandronate, incadronate, minodronate, neridronate, olpadronate, pamidronate, piridronate, risedronate, tiludronate, and zoledronate. Pamidronate or zoledronate is preferred.

Examples of the muscle relaxant may include cyclobenzaprine, metaxalone, and baclofen. Baclofen is preferred.

Examples of the retinoic acid receptor γ agonist may include palovarotene.

Examples of the additional therapeutic drug for brain tumor that may be administered in combination with the anti-ALK2 antibody may include temozolomide, bevacizumab, carmustine, lomustine, procarbazine hydrochloride, and vincristine.

Depending on the condition of ectopic ossification or brain tumor or the intended degree of treatment and/or prevention, two or three or more additional therapeutic drugs may be administered, and these additional therapeutic drugs may be included in the same preparation and thereby administered at the same time. The additional therapeutic drug and the anti-ALK2 antibody may also be included in the same preparation and thereby administered at the same time. Also, the anti-ALK2 antibody and the additional therapeutic drug may be included in distinct preparations and administered at the same time. Alternatively, the additional agent and the anti-ALK2 antibody may be separately administered one after another. Specifically, a therapeutic drug comprising the anti-ALK2 antibody or the antigen-binding fragment thereof as an active ingredient may be administered after administration of the additional therapeutic drug, or the additional therapeutic drug may be administered after administration of the therapeutic drug containing the anti-ALK2 antibody or the antigen-binding fragment thereof as an active ingredient. For administration in gene therapy, a gene for a protein serving as a therapeutic drug for ectopic ossification or brain tumor and the gene for the anti-ALK2 antibody may be inserted at a site downstream of distinct promoter regions or the same promoter region and may be introduced into distinct vectors or the same vector.

The anti-ALK2 antibody or the fragment thereof may be conjugated with a therapeutic drug for ectopic ossification or brain tumor to produce a targeted drug conjugate described in M.C. Garnet "Targeted drug conjugates: principles and progress", Advanced Drug Delivery Reviews, (2001) 53, 171-216. For this purpose, an antibody molecule as well as any antibody fragment is applicable unless their ability to bind to ALK 2 ALK2-recognizing properties) and ability to cross-link ALK2 are completely deleted. Examples of the antibody fragment may include fragments such as $F(ab')_2$. The conjugation manner of the anti-ALK2 antibody or the fragment of the antibody with the therapeutic drug for FOP may take various forms described in, for example, M.C. Garnet "Targeted drug conjugates: principles and progress", Advanced Drug Delivery Reviews, (2001) 53, 171-216, G. T. Hermanson "Bioconjugate Techniques" Academic Press, California (1996), Putnam and J. Kopecek "Polymer Conjugates with Anticancer Activity" Advances in Polymer Science (1995) 122, 55-123. Specific examples thereof may include a manner in which the anti-ALK2 antibody is chemically conjugated with the therapeutic drug for ectopic ossification or brain tumor either directly or via a spacer such as an oligopeptide, and a manner in which the anti-ALK2 antibody is conjugated with the therapeutic drug for ectopic ossification or brain tumor via an appropriate drug carrier. Examples of the drug carrier may include drug delivery systems (e.g., X. Yu et al., J Nanomater. 2016; 2016:doi:10.1155/2016/1087250; and J. Wang et al., Drug Delivery, 25: 1, 1319-1327, DOI:10.1080/10717544.2018.1477857) such as liposomes, nanoparticles, nanomicelles, and water-soluble polymers. Examples of such a manner via the drug carrier may more specifically include a manner in which the therapeutic drug for ectopic ossification or brain tumor is encapsulated in a liposome and the liposome is conjugated with the antibody, and a manner in which the therapeutic drug for ectopic ossification or brain tumor is chemically conjugated with a water-soluble polymer (compound having a molecular weight on the order of 1000 to 100,000) either directly or via a spacer such as an oligopeptide and the water-soluble polymer is conjugated with the antibody. The conjugation of the antibody (or the fragment) with the therapeutic drug for ectopic ossification or brain tumor or the drug carrier (e.g., a liposome or a water-soluble polymer) may be carried out by a method well known to those skilled in the art, such as a method described in G. T. Hermanson "Bioconjugate Techniques" Academic Press, California (1996), and Putnam and J. Kopecek "Polymer Conjugates with Anticancer Activity" Advances in Polymer Science (1995) 122, 55-123. The encapsulation of the therapeutic drug for ectopic ossification or brain tumor in the liposome may be carried out by a method well known to those skilled in the art, such as a method described in, for example, D. D. Lasic "Liposomes: From Physics to Applications", Elsevier Science Publishers B. V., Amsterdam (1993). The conjugation of the therapeutic drug for ectopic ossification or brain tumor with the water-soluble polymer may be carried out by a method well known to those skilled in the art, such as a method described in D. Putnam and J Kopecek "Polymer Conjugates with Anticancer Activity" Advances in Polymer Science (1995) 122, 55-123. The conjugate of the antibody (or the fragment) with the protein as a therapeutic drug for ectopic ossification or brain tumor (e.g., an antibody or a fragment thereof) may be prepared by any of the methods described above or a genetic engineering method well known to those skilled in the art.

For the administration of the human type anti-ALK2 antibody to a patient, the dose of the anti-ALK2 antibody used in the present invention is, for example, approximately 0.1 to 100 mg/kg body weight, which may be administered once or twice or more per 1 to 180 days. However, the dose and the number of doses should generally be determined in consideration of the sex, body weight, and age of a patient, symptoms, severity, adverse reactions, etc., and therefore, are not limited to the dose or usage described above.

Non-limiting examples of formulations comprising the anti-ALK2 antibody used in the present invention may include injections including intravenous drips, suppositories, transnasal formulations, sublingual formulations, and transdermal absorption formulations. The administration route is an oral administration route or a parenteral administration route. Non-limiting examples of the parenteral administration route include intravenous, intraarterial, intramuscular, intrarectal, transmucosal, intradermal, intraperitoneal, and intraventricular routes.

7. Determination of Eligibility of Patient for Treatment and/or Prevention

In the present invention, the following methods may be carried out in order to effectively treat and/or prevent a patient having a mutation in ALK2 protein (e.g., an active mutation in ALK2) by the administration of the anti-ALK2 antibody or the pharmaceutical composition comprising the antibody.

A first method is a method for predicting a risk of developing an adverse reaction ascribable to the administration of an anti-ALK2 antibody or an antigen-binding fragment thereof, comprising the steps of:
  (a) detecting the presence or absence of an active mutation in ALK2 and a mutation of an amino acid residue at position 330 of ALK2 of a patient; and
  (b) determining that when the patient has the active mutation in ALK2 and has no mutation of an amino acid residue at position 330 of ALK2, the patient has a low risk of developing an adverse reaction ascribable to the administration of an anti-ALK2 antibody or an antigen-binding fragment thereof.

A second method is a method for predicting responsiveness to treatment and/or prevention by the administration of an anti-ALK2 antibody or an antigen-binding fragment thereof, comprising the steps of:
  (a) detecting the presence or absence of an active mutation in ALK2 and a mutation of an amino acid residue at position 330 of ALK2 of a patient; and
  (b) determining that when the patient has the active mutation in ALK2 and has no mutation of an amino acid residue at position 330 of ALK2, the patient has responsiveness to treatment and/or prevention by the administration of an anti-ALK2 antibody or an antigen-binding fragment thereof.

A third method is a method for selecting a patient to be treated and/or prevented by the administration of an anti-ALK2 antibody or an antigen-binding fragment thereof, comprising the steps of:
(a) detecting the presence or absence of an active mutation in ALK2 and a mutation of an amino acid residue at position 330 of ALK2 of a patient; and
(b) selecting the patient as a patient to be treated and/or prevented by the administration of an anti-ALK2 antibody or an antigen-binding fragment thereof when the patient has the active mutation in ALK2 and having no mutation of an amino acid residue at position 330 of ALK2.

A fourth method is a method for treating and/or preventing a disease by the administration of an anti-ALK2 antibody or an antigen-binding fragment thereof, comprising the steps of:
(a) detecting the presence or absence of an active mutation in ALK2 and a mutation of an amino acid residue at position 330 of ALK2 of a patient; and
(b) administering to the patient the anti-ALK2 antibody or the antigen-binding fragment thereof when the patient has the active mutation in ALK2 and has no mutation of an amino acid residue at position 330 of ALK2.

The fourth method may further comprise performing any of the steps (b) of the first to third methods, i.e.,
(Step (b) of the First Method)
the step of determining that when a patient has the active mutation in ALK2 and has no mutation of an amino acid residue at position 330 of ALK2, the patient has a low risk of developing an adverse reaction ascribable to the administration of an anti-ALK2 antibody or an antigen-binding fragment thereof,
(Step (b) of the Second Method)
the step of determining that when a patient has the active mutation in ALK2 and has no mutation of an amino acid residue at position 330 of ALK2, the patient has responsiveness to treatment and/or prevention by the administration of an anti-ALK2 antibody or an antigen-binding fragment thereof, and
(Step (b) of the Third Method)
the step of selecting the patient as a patient to be treated and/or prevented by the administration of an anti-ALK2 antibody or an antigen-binding fragment thereof when the patient has the active mutation in ALK2 and has no mutation of an amino acid residue at position 330 of ALK2.

Through such further step, whether a patient is eligible for treatment and/or prevention by the administration of the anti-ALK2 antibody or the antigen-binding fragment thereof, whether a patient has an adverse reaction, or the like is determined, and, as a result, the anti-ALK2 antibody or the antigen-binding fragment thereof can then be administered to a patient confirmed to be eligible, thereby to elicit therapeutic effects in the patient, thus a so-called personalized medicine can be performed for the patient.

As used herein, the term "determination" includes decision, evaluation, or assistance for determination.

In the first to fourth methods, the administration of the anti-ALK2 antibody or the antigen-binding fragment thereof is preferably the administration of a pharmaceutical composition described in the section 6.

In the first to fourth methods, the step (b) may further comprise a step of confirming that the active mutation in ALK2 is not G328V mutation.

In the first to fourth methods, the active mutation in ALK2 is preferably at least one selected from L196P, delP197_F198insL, R2021, R206H, Q207E, R258S, R258G, G325A, G328E, G328R, G328W, G356D, and R375P, or at least one selected from R206H, R258G, G328E, G328W, and G356D.

Moreover, in the first to fourth methods, the above-mentioned patient is a subject having an unidentified disease, or a subject suspected of having a disease caused by an active mutation in ALK2. The disease to be treated is, for example, a disease caused by an active mutation in ALK2, preferably ectopic ossification or brain tumor, more preferably ectopic ossification. Specific examples of these diseases are described in the section 6. The disease is further preferably fibrodysplasia ossificans progressiva (FOP) or diffuse intrinsic pontine glioma (DIPG), still further preferably fibrodysplasia ossificans progressiva (FOP), although the disease is not intended to be limited thereto.

EXAMPLES

The present invention will be specifically described hereinafter with reference to Examples; however, the invention is not limited thereto. In the following Examples, unless otherwise specified, any procedures concerning genetic manipulation were performed in accordance with methods described in "Molecular Cloning" (Sambrook, J., Fritsch, E. F., and Maniatis, T., Cold Spring Harbor Laboratory Press, 1989), or where commercially available reagents or kits were used, they were used in accordance with the manuals for such commercial products.

Example 1

Evaluation of BMP signal transduction-activating effect of Anti-ALK2 antibody (27D-H2L2_LALA) by luciferase reporter assay The anti-ALK2 antibody (27D-H2L2_LALA) used in the experiment was prepared by the method described in Example 12 of WO 2016/121908.

The BMP intracellular signal transduction-activating effect mediated by the anti-ALK2 antibody prepared was analyzed using a BMP-specific luciferase reporter. HEK293A cells were seeded into a 96-well white plate for luciferase assay (manufactured by Corning, Inc.) at $1 \times 10^4$ cells/well, and cultured overnight in 10% FBS-containing DMEM medium under the conditions of 5% $CO_2$ at 37° C. On the next day, each of human or mouse wild-type ALK2-expressing or R206H mutant-expressing plasmids was introduced together with pGL4.26/Id1WT4F-luc (Genes Cells, 7, 949 (2002)), into the cells using Lipofectamine 2000 manufactured by Invitrogen Corp.). After 3 hours, the medium was exchanged with fresh OPTI-MEM I (manufactured by Life Technologies Corp.). Then, the serially diluted antibody was added, and the cells were further cultured overnight. On the next day, the luciferase activity was measured using the plate reader SpectraMaxM4 manufactured by Molecular Devices, LLC) and using One-Glo Luciferase Assay System (manufactured by Promega Corp.).

The results are shown in FIG. 1. 27D-H2L2_LALA was confirmed to elevate BMP-specific luciferase activity in a concentration-dependent manner only in HEK293 cells that express the R206H mutant of mouse ALK2 lower panel of FIG. 1A). On the other hand, this antibody was not confirmed to elevate BMP reporter activity in cells that express the R206H mutant of human ALK2 lower panel of FIG. 1B) or human or mouse wild-type ALK2 upper panels of FIGS. 1A and 1B).

Example 2

Preparation of Fab (27D-H2L2_FAB) and F(ab')$_2$ (27D-H2L2_F(ab)$_2$) of anti-ALK2 antibody (27D-H2L2_LALA)
2)-1
Preparation of Fab from 27D-H2L2_LALA
27D-H2L2_LALA was restrictively cleaved with Papain from Papaya latex (Sigma-Aldrich Co. LLC), to remove Fc fragments and the like using HiLoad 26/600 Superdex 200 pg (GE Healthcare Japan Corp.). Then, unreacted 27D-H2L2_LALA was separated using HiTrap Mab Select SuRe, 1 mL (GE Healthcare Japan Corp.) to collect Fab.
2)-2
Preparation of F(ab')$_2$ from 27D-H2L2_LALA
27D-H2L2_LALA was restrictively cleaved with Endoproteinase Glu-C (Sigma-Aldrich Co. LLC), and unreacted 27D-H2L2_LALA was separated using HiTrap Mab Select SuRe, 10 mL (GE Healthcare Japan Corp.). Then, F(ab')$_2$ was collected using Bio-Scale CHT Type I, 5 mL (Bio-Rad Laboratories, Inc.).

Example 3

Evaluation of BMP signal transduction-activating effects of Fab (27D-H2L2_Fab) and F(ab')$_2$ (27D-H2L2_F(ab)$_2$) of anti-ALK2 antibody by luciferase reporter assay
The BMP intracellular signal transduction-activating effects mediated by 27D-H2L2_Fab and 27D-H2L2_F(ab)$_2$ prepared in Example 2 were analyzed using a BMP-specific luciferase reporter. The comparative control used was the full-length anti-ALK2 antibody 27D-H2L2_LALA. The luciferase reporter assay was conducted by the same way as in Example 1.
The results are shown in FIG. 2. 27D-H2L2_F(ab)$_2$ was confirmed to elevate BMP-specific luciferase activity in a concentration-dependent manner only in HEK293 cells that express the R206H mutant of mouse ALK2, as with 27D-H2L2_LALA. On the other hand, 27D-H2L2_Fab was not confirmed to elevate BMP reporter activity under any of the conditions.
The results are shown in FIG. 2. 27D-H2L2_F(ab)$_2$ was confirmed to elevate BMP-specific luciferase activity in a concentration-dependent manner only in HEK293 cells that express the R206H mutant of mouse ALK2, as in 27D-H2L2_LALA. On the other hand, 27D-H2L2_Fab was not confirmed to elevate BMP reporter activity under any of the conditions.

Example 4

Figure 3:
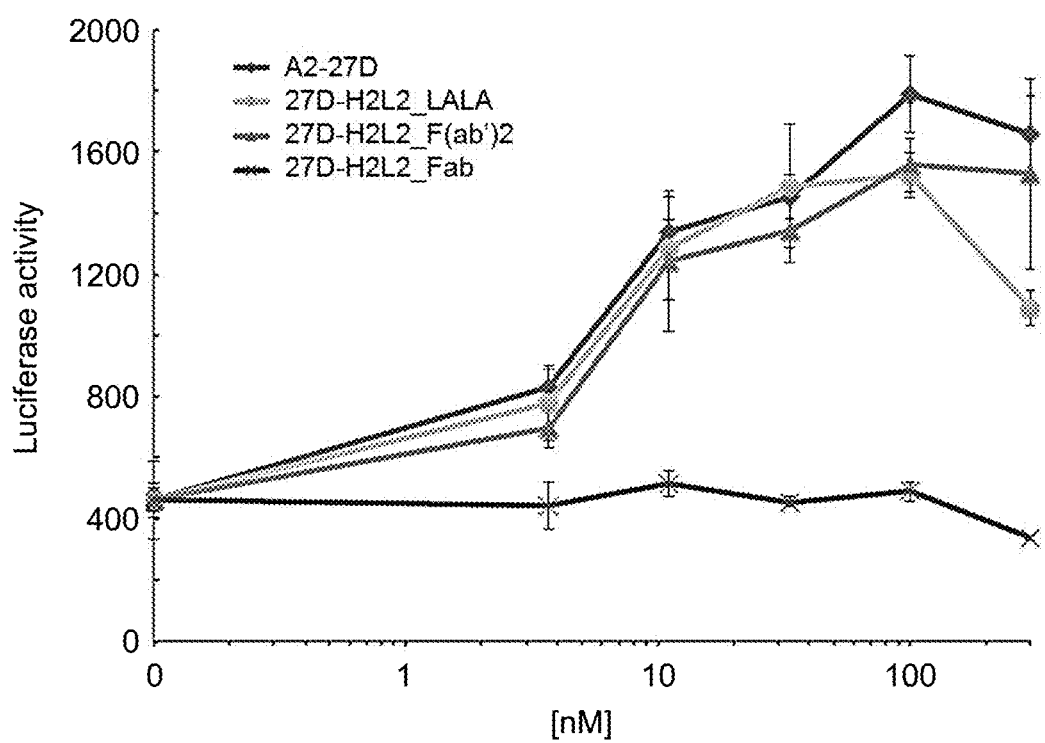
FIG. 3 This figure is a graph showing, using Nanoluc Binary Technology, that A2-27D, 27D-H2L2_LALA and 27D-H2L2_F(ab')$_2$ induce the cross-link formation (i.e., complex formation) of ALK2. By contrast, 27D-H2L2_Fab did not induce the cross-link formation (i.e., complex formation) of ALK2. The ordinate depicts luciferase activity (luc activity) determined using Nanoluc Binary Technology". The abscissa depicts an antibody concentration.

Evaluating in vitro activity of cross-linking ALK2 molecules by anti-ALK2 antibody
NanoBiT assay (manufactured by Promega Corp.) was conducted in order to verify the possibility that the effect of activating the BMP-specific luciferase reporter by 27D-H2L2_LALA and 27D-H2L2_F(ab)$_2$, confirmed in Examples 1 and 3, was mediated by the cross-link between two ALK2 molecules. A nucleotide sequence encoding the full-length human ALK2 was inserted into pBit1.1-C [TK/LgBiT] and pBit2.1-C [TK/SmBiT] Vectors (manufactured by Promega Corp.) to construct expression vectors. C2C12 cells were seeded into a 96-well white plate for luciferase assay (manufactured by Greiner Group AG) at 5×10$^3$ cells/well, and cultured overnight in 15% FBS-containing DMEM medium under the conditions of 5% CO$_2$ at 37° C. On the next day, two types of ALK2 expression plasmids were introduced into the cells using Lipofectamine 2000 manufactured by Invitrogen Corp.). After 2.5 hours, the medium was replaced with fresh OPTI-MEM I (manufactured by Life Technologies Corp.), and the cells were further cultured overnight. On the next day, the serially diluted antibody was added together with a substrate of Nano-Glo Live Cell Assay System (manufactured by Promega Corp.), and the cells were cultured for 15 minutes. Then, the luciferase activity was measured using a plate reader GENios (manufactured by Tecan Trading AG).
The results are shown in FIG. 3. It was confirmed that A2-27D, 27D-H2L2_LALA and 27D-H2L2_F(ab)$_2$ promoted the cross-link formation of ALK2 or the formation of ALK2 complex) in an antibody concentration-dependent manner, whereas 27D-H2L2_Fab did not induce the cross-link formation of ALK2 or the complex formation of ALK2).

Example 5

Figure 5:
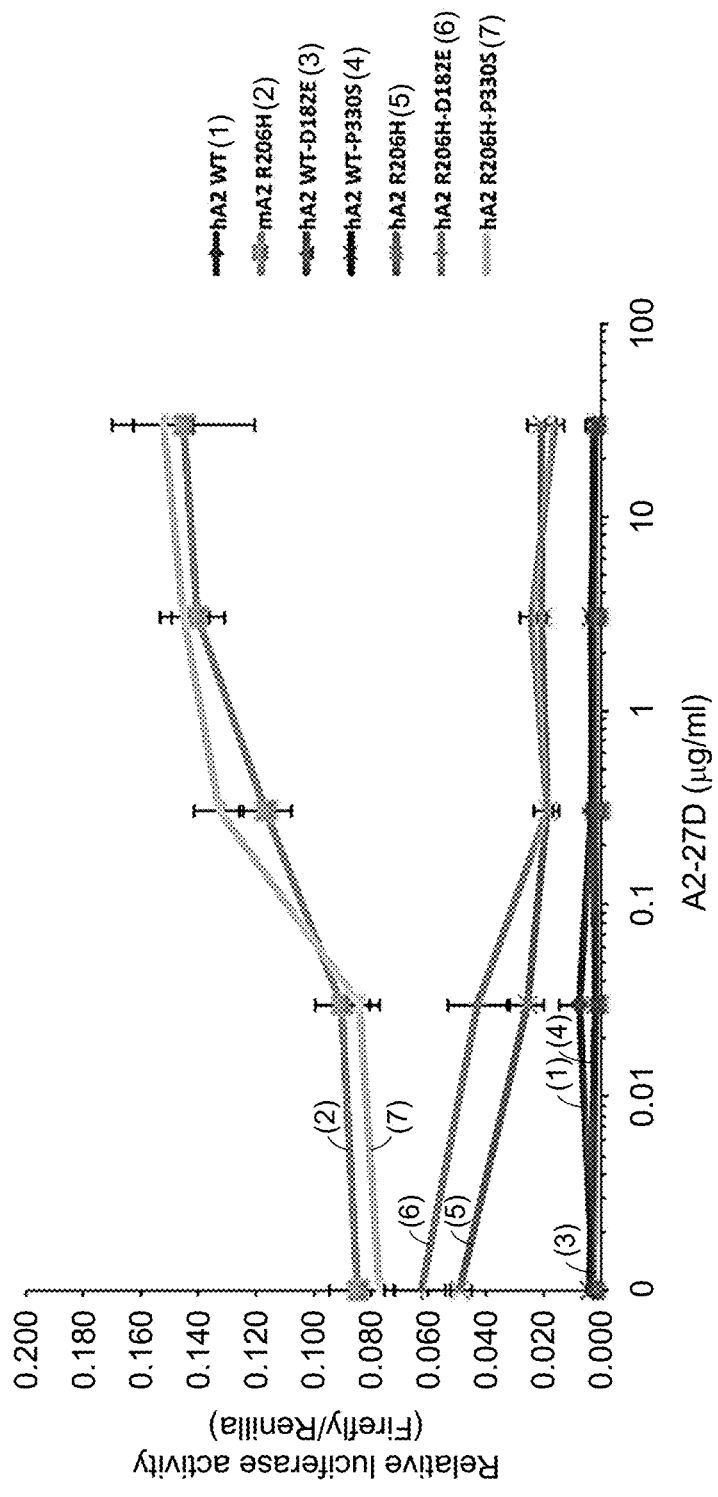
FIG. 5 This figure is a graph showing, using a BMP-specific luciferase reporter, that the anti-ALK2 antibody (A2-27D) activates the BMP signal transduction in HEK293 cells expressing human R206H ALK2 with proline at position 330 substituted by serine. Inhibiting the activation of the BMP signal transduction was found in HEK293 cells expressing mouse R206H ALK2 with serine at position 330 substituted by proline (data not shown). This figure also shows, using the BMP-specific luciferase reporter, that the anti-ALK2 antibody activates the BMP signal transduction in HEK293 cells expressing mouse R206H ALK2 but does not activate or suppresses or inhibits the BMP signal transduction in HEK293 cells that express human WT ALK2 and the indicated other human ALK2 mutants such as human ALK2 with aspartic acid at position 182 substituted by glutamic acid.

Verifying influence of amino acid substitutions at positions 182 and 330 on the effect of activating the BMP-specific luciferase reporter by anti-ALK2 antibody
5)-1
Alignment of amino acid sequences of full-length ALK2 among human, cynomolgus monkey, dog, rat, and mouse
Results of the sequence alignment are shown in FIG. 4. When the amino acids of the human, cynomolgus monkey, dog, rat and mouse ALK2 intracellular regions were compared with one another, they were different in amino acid residues at positions 182 and 330.
5)-2
Verifying influence of amino acid substitutions at positions 182 and 330 on the effect of activating the BMP-specific luciferase reporter by anti-ALK2 antibody
In order to analyze the roles of D182E and P330S differing between the human and mouse ALK2 intracellular regions, expression vectors were constructed using pcDEF3 such that D182E or P330S mutation was introduced into each of wild-type human ALK2 and R206H mutants of human ALK2. HEK293A cells were seeded into a 96-well white plate for luciferase reporter assay (manufactured by Greiner Group AG) at 1×10$^4$ cells/well, and cultured overnight in 10% FBS-containing DMEM medium under the conditions of 5% CO$_2$ at 37° C. On the next day, each of ALK2 expression vector, pGL4.26/Id1WT4F-luc (Genes Cells, 7, 949 (2002)), and phRL SV40 manufactured by Promega Corp.) was introduced into the cells using Lipofectamine 2000 manufactured by Invitrogen Corp.). After 2.5 hours, the medium was exchanged with fresh OPTI-MEM I (manufactured by Life Technologies Corp.) containing the serially diluted antibody A2-27D, and the cells were further cultured overnight. On the next day, the firefly and *Renilla* luciferase activities were measured using a plate reader GENios (manufactured by Tecan Trading AG), and using Dual-Glo Luciferase Assay System (manufactured by Promega Corp.).
The results are shown in FIG. 5. A2-27D was confirmed to elevate activity in a concentration-dependent manner only for the R206H mutants of human ALK2 harboring P330S mutation, as in the R206H mutant of mouse ALK2.

Example 6

Verifying influence of amino acid substitutions at position 330 on the effect of activating the BMP-specific luciferase reporter by anti-ALK2 antibody In order to analyze the role of P330 of human ALK2, expression vectors were constructed using pcDEF3 such that P330D, P330E, P330A, or P330V mutation was introduced into each of wild-type human ALK2 and R206H mutants of human ALK2. In order to analyze the role of S330 of mouse ALK2, expression vectors were constructed such that S330P mutation was introduced into each of wild-type mouse ALK2 and R206H mutants of mouse ALK2. HEK293A cells were transfected with these expression vectors by the same way as in Example 5 and cultured overnight in a medium containing A2-27D, followed by luciferase activity measurement.

Figure 6:
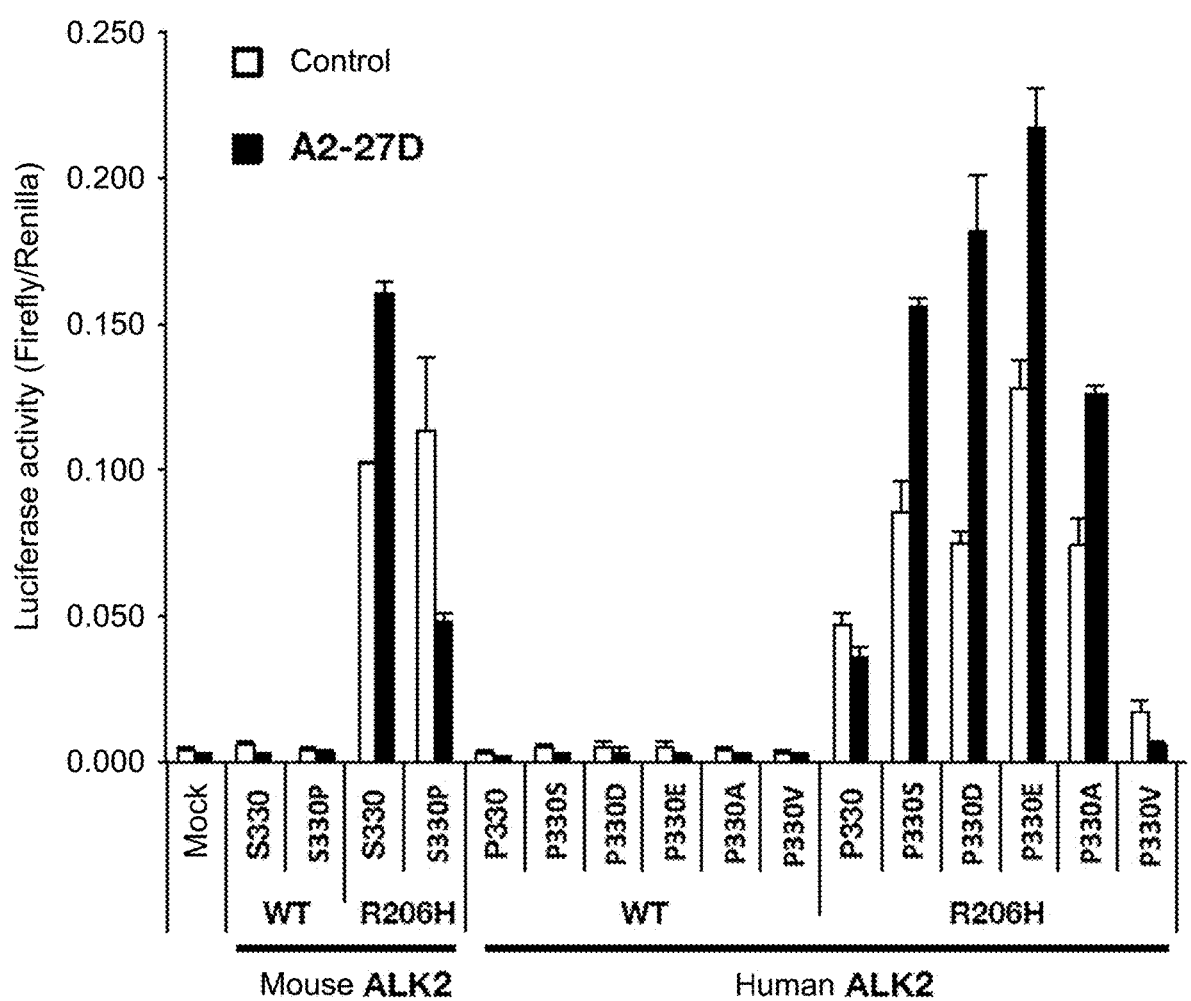
FIG. 6 This figure is a graph showing, using a BMP-specific luciferase reporter, that the anti-ALK2 antibody (A2-27D) activates the BMP signal transduction in HEK293 cells expressing human R206H ALK2 with proline (P) at position 330 substituted by serine (S), aspartic acid (D), glutamic acid (E), or alanine (A), but does not activate the BMP signal transduction for human R206H ALK2 with proline (P) at position 330 substituted by valine (V). This figure also shows that the anti-ALK2 antibody does not activate the BMP signal transduction for human WT ALK2 having the substitution described above but containing no R206H mutation. The presence or absence of the activation of BMP signal transduction is also indicated for mouse ALK2 having the mutation shown in this figure. A control ('Control') is rat IgG2.

The results are shown in FIG. 6. A2-27D inhibited the activity for the mouse R206H mutant harboring the introduced S330P mutation (i.e., antagonistic activity), whereas A2-27D promoted the activity when the amino acid at this position was S330 where the amino acid residue at position 330 is serine.) (i.e., agonistic activity). On the other hand, it was revealed that A2-27D promoted the activity for the human R206H mutants harboring the introduced P33 0 S, P330D, P330E, or P330A mutation (i.e., agonistic activity), whereas the antibody inhibited the activity when the mutation was P330V.

Example 7

Evaluation of BMP signal transduction-activating effects of four types of anti-ALK2 antibodies (27D-H2L2_LALA, 15A-H4L6_IgG2, A2-11E, and A2-25C) by luciferase reporter assay The anti-ALK2 antibodies (27D-H2L2_LALA, 15A-H4L6_IgG2, A2-11E, and A2-25C) used in the experiment were prepared by the methods described in Examples 12, 11 and 1 of WO 2016/121908.

The BMP intracellular signal transduction-activating effects mediated by the anti-ALK2 antibodies prepared were analyzed by the same way as in Example 1 using a BMP-specific luciferase reporter.

Figure 7:
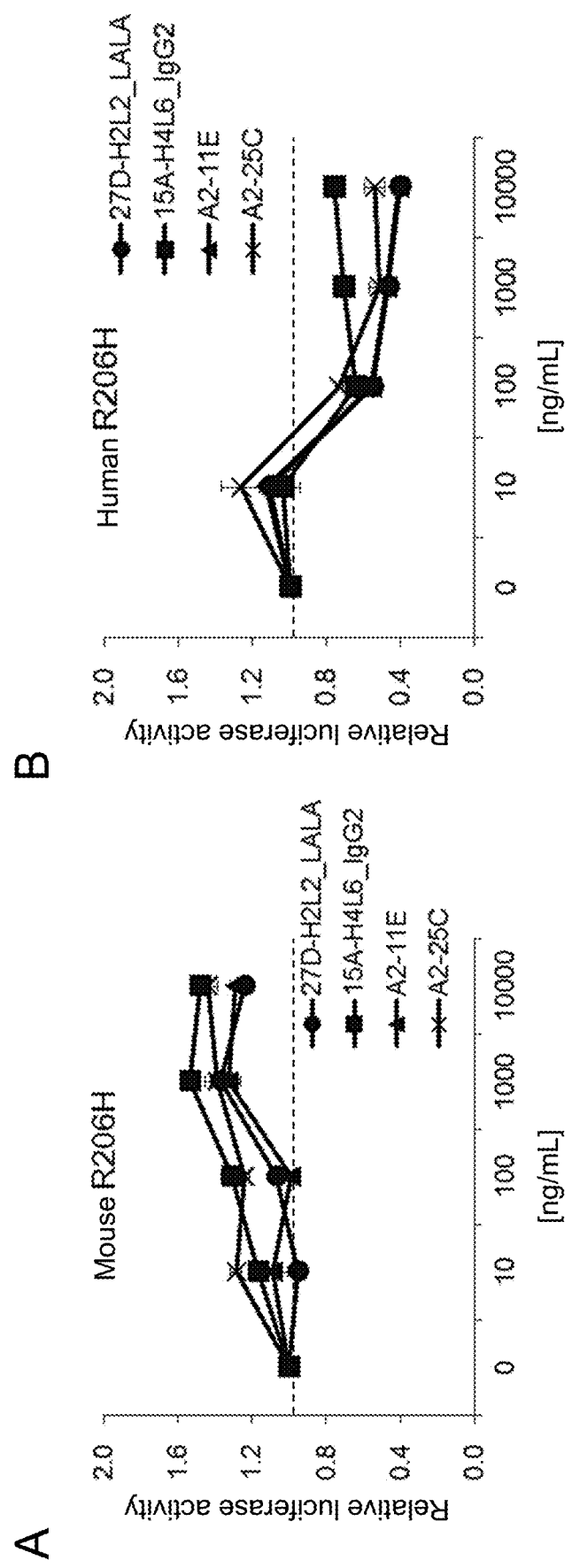
FIG. 7A-B This figure provides graphs showing, using a BMP-specific luciferase reporter, that four types of anti-ALK2 antibodies (27D-H2L2_LALA, 15A-H4L6_IgG2, A2-11E, and A2-25C) activate the BMP signal transduction in HEK293 cells expressing mouse R206H ALK2 (FIG. 7A), whereas none of these antibodies activate the BMP signal transduction in HEK293 cells expressing a human R206H ALK2 mutant (FIG. 7B). The ordinate depicts relative luciferase activity (Relative luc activity) to an untreated control (i.e., a control free from the anti-ALK2 antibodies). The abscissa depicts an antibody concentration.

The results are shown in FIG. 7. 15A-H4L6_IgG2, A2-11E, and A2-25C were confirmed to elevate BMP-specific luciferase activity in a concentration-dependent manner only in HEK293 cells that express the R206H mutant of mouse ALK2, as in 27D-H2L2_LALA. On the other hand, none of these antibodies were confirmed to elevate BMP reporter activity in cells expressing the R206H mutant of human ALK2.

Example 8

Verifying effect of activating the BMP-specific luciferase reporter by anti-ALK2 antibody on various ALK2 mutants other than R206H mutant Expression vectors were constructed using pcDEF3 such that each of fourteen types of human ALK2 mutants (L196P, P197F198del_insL (also referred to as PF197-8L), R202I, R206H, Q207E, R258G, R258S, G325A, G328E, G328R, G328V, G328W, G356D, and R375P mutants) found in FOP and DIPG, and a constitutively active Q207D mutant, were introduced into each vector. HEK293 cells were caused to overexpress these mutants by the same way as in Examples 5 and 6, and cultured overnight in a medium containing serially diluted A2-27D, followed by luciferase activity measurement. In this experiment, the G328V mutant and the Q207D mutant were used in the assay such that their amounts were 1/3 of the amount of the other mutants (e.g., 12.5 ng/well relative to 37.5 ng each of the other mutants/well) and 1/20 e.g., 1.875 ng/well relative to 37.5 ng each of the other mutants/well).

Figure 8:
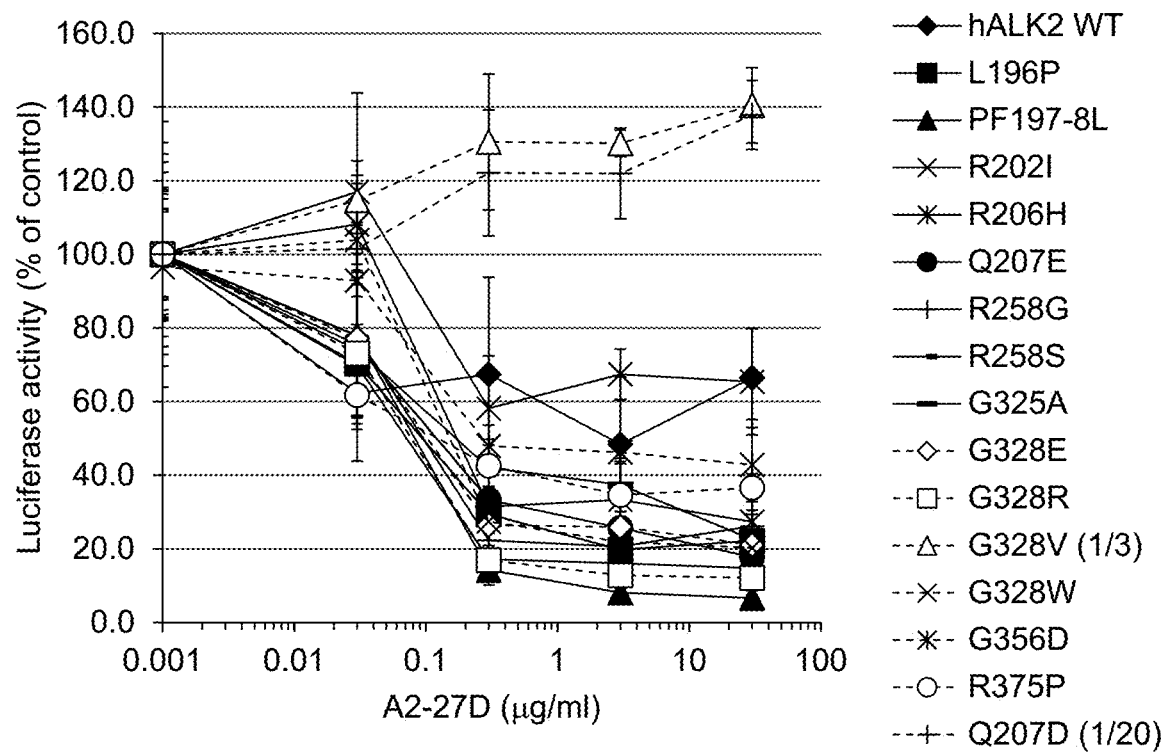
FIG. 8 This figure is a graph showing, using a BMP-specific luciferase reporter, that the anti-ALK2 antibody (A2-27D) activates the BMP signal transduction in HEK293 cells expressing human G328V or Q207D ALK2, but does not activate the BMP signal transduction in HEK293 cells expressing other human ALK2 mutants (R206H, L196P, PF197-8L (also referred to as "delP197_F198insL"), R2021, Q207E, R258G, R258S, G325A, G328E, G328R, G328W, G356D, and R375P). Activity was measured in the same way as in Example 5. In the figure, the ordinate depicts luciferase activity against an untreated control. The abscissa depicts an A2-27D concentration. As for G328V (1/3) and Q207D (1/20), the G328V mutant and the Q207D mutant were used in the assay such that their amounts were 1/3 of the amount of the other mutants (e.g., 12.5 ng/well when each of the other mutants was 37.5 ng/well) and 1/20 e.g., 1.875 ng/well when each of the other mutants was 37.5 ng/well).

The results are shown in FIG. 8. It was confirmed that A2-27D promoted the activity in a concentration-dependent manner for the G328V mutant found only in DIPG and the constitutively active Q207D mutant among the human ALK2 mutants, but that A2-27D inhibited the activity in a concentration-dependent manner for the other human ALK2 mutants.

INDUSTRIAL APPLICABILITY

The present invention has revealed that ectopic ossification and/or brain tumor may be effectively treated and/or prevented by administering an anti-ALK2 antibody having an ability to bind to ALK2 and an ability to cross-link ALK2 to a patient having an active mutation in ALK2 and having no mutation of an amino acid residue at position 330 of ALK2, preferably the patient having no G328V mutation. The present invention has also revealed: that a risk of developing an adverse reaction ascribable to the administration of an anti-ALK2 antibody may be predicted; that responsiveness to treatment and/or prevention by the administration of an anti-ALK2 antibody may be predicted; and that a subject to be treated and/or prevented by the administration of an anti-ALK2 antibody may be selected.

Free Text of Sequence Listing
SEQ ID NO: 17: Gln is a substituted amino acid residue.
SEQ ID NO: 30: Amino acid sequence of humanized hA2-15A-L4
SEQ ID NO: 31: Amino acid sequence of humanized hA2-15A-H4
SEQ ID NO: 32: Amino acid sequence of humanized hA2-15A-L6
SEQ ID NO: 33: Amino acid sequence of humanized hA2-15A-H4 IgG2 type
SEQ ID NO: 34: Amino acid sequence of humanized hA2-27D-H2
SEQ ID NO: 35: Amino acid sequence of humanized hA2-27D-L2
SEQ ID NO: 36: Amino acid sequence of humanized hA2-27D-H3
SEQ ID NO: 37: Amino acid sequence of humanized hA2-27D-L4
SEQ ID NO: 38: Amino acid sequence of humanized hA2-27D-H2_LALA
SEQ ID NO: 39: Amino acid sequence of humanized hA2-27D-H3 LALA All publications, patents, and patent applications cited herein are incorporated herein by reference in their entirety.

The invention claimed is:

1. A method for binding a mutated ALK2 in a subject, comprising:
administering to a subject that has an active mutation in ALK2 an anti-ALK2 antibody or an antigen-binding fragment thereof or a pharmaceutical composition comprising an anti-ALK2 antibody or an antigen-binding fragment thereof;
wherein the active mutation in ALK2 comprises at least one mutation selected from L196P, delP197_F198insL, R202I, R206H, Q207E, R258S, R258G, G325A, G328E, G328R, G328W, G356D, and R375P, relative to SEQ ID NO: 1, but does not have a mutation of an amino acid residue at position 330 of SEQ ID NO: 1, wherein the subject has ectopic ossification or diffuse intrinsic pontine glioma (DIPG).

2. The method according to claim 1, wherein the antibody or the antigen-binding fragment thereof comprises a heavy chain variable region comprising a CDRH1, a CDRH2, and a CDRH3, which comprise the amino acid sequences of:
SEQ ID NO: 5, SEQ ID NO: 6, and SEQ ID NO: 7, respectively,
SEQ ID NO: 11, SEQ ID NO: 12, and SEQ ID NO: 13, respectively,
SEQ ID NO: 18, SEQ ID NO: 19, and SEQ ID NO: 20, respectively, or
SEQ ID NO: 24, SEQ ID NO: 25, and SEQ ID NO: 26, respectively; and
a light chain variable region comprising a CDRL1, a CDRL2, and a CDRL3, which comprise the amino acid sequences of:
SEQ ID NO: 8, SEQ ID NO: 9, and SEQ ID NO: 10, respectively,
SEQ ID NO: 8, SEQ ID NO: 17, and SEQ ID NO: 10, respectively,
SEQ ID NO: 14, SEQ ID NO: 15, and SEQ ID NO: 16, respectively,
SEQ ID NO: 21, SEQ ID NO: 22, and SEQ ID NO: 23, respectively, or
SEQ ID NO: 27, SEQ ID NO: 28, and SEQ ID NO: 29, respectively.

3. The method according to claim 1, wherein the anti-ALK2 antibody or the antigen-binding fragment thereof specifically binds to a polypeptide consisting of amino acid residues from position 21 to position 123 in the amino acid sequence of SEQ ID NO: 1.

4. The method according to claim 1, wherein the active mutation in ALK2 is not a G328V mutation.

5. The method according to claim 1, wherein the active mutation in ALK2 comprises at least one mutation selected from R206H, R258G, G328E, G328W, and G356D.

6. The method according to claim 1, wherein the subject has ectopic ossification.

7. The method according to claim 1, wherein the subject has fibrodysplasia ossificans progressiva (FOP) or diffuse intrinsic pontine glioma (DIPG).

8. The method according to claim 7, wherein the subject has fibrodysplasia ossificans progressiva (FOP).

9. The method of claim 1, wherein the subject has diffuse intrinsic pontine glioma (DIPG).

10. The method of claim 1, wherein the anti-ALK2 antibody or the antigen-binding fragment thereof binds to:
(i) an epitope comprising each residue of glutamic acid at position 38, glycine at position 39, isoleucine at position 59, asparagine at position 60, aspartic acid at position 61, glycine at position 62, phenylalanine at position 63, histidine at position 64, valine at position 65, tyrosine at position 66, asparagine at position 102, threonine at position 104, glutamine at position 106, and leucine at position 107 in the amino acid sequence of SEQ ID NO: 1; or
(ii) an epitope comprising each residue of glutamic acid at position 38, glycine at position 39, leucine at position 40, isoleucine at position 59, asparagine at position 60, aspartic acid at position 61, glycine at position 62, phenylalanine at position 63, histidine at position 64, valine at position 65, tyrosine at position 66, and threonine at position 104 in the amino acid sequence of SEQ ID NO: 1.

11. The method of claim 1, wherein the anti-ALK2 antibody or the antigen-binding fragment thereof is a monoclonal antibody, a polyclonal antibody, a chimeric antibody, a humanized antibody, a human antibody, a diabody, a multispecific antibody, or F(ab')2.

12. The method of claim 2, wherein the anti-ALK2 antibody or the antigen-binding fragment thereof comprises a heavy chain variable region comprising:

a1) an amino acid sequence consisting of amino acid residues from position 20 to position 142 of the amino acid sequence of SEQ ID NO: 31,
a2) an amino acid sequence consisting of amino acid residues from position 20 to position 142 of the amino acid sequence of SEQ ID NO: 33,
a3) an amino acid sequence consisting of amino acid residues from position 20 to position 140 of the amino acid sequence of SEQ ID NO: 34,
a4) an amino acid sequence consisting of amino acid residues from position 20 to position 140 of the amino acid sequence of SEQ ID NO: 36,
a5) an amino acid sequence consisting of amino acid residues from position 20 to position 140 of the amino acid sequence of SEQ ID NO: 38,
a6) an amino acid sequence consisting of amino acid residues from position 20 to position 140 of the amino acid sequence of SEQ ID NO: 39,
a7) an amino acid sequence having at least 95% identity to any one amino acid sequence selected from the amino acid sequences a1) to a6),
a8) an amino acid sequence having at least 99% identity to any one amino acid sequence selected from the amino acid sequences a1) to a6), or
a9) an amino acid sequence comprising a substitution(s), a deletion(s), or an addition(s) of one or several amino acid residues in any one amino acid sequence selected from the amino acid sequences a1) to a6); and
the anti-ALK2 antibody or the antigen-binding fragment thereof comprises a light chain variable region comprising:
b1) an amino acid sequence consisting of amino acid residues from position 21 to position 133 of the amino acid sequence of SEQ ID NO: 32,
b2) an amino acid sequence consisting of amino acid residues from position 21 to position 129 of the amino acid sequence of SEQ ID NO: 35,
b3) an amino acid sequence consisting of amino acid residues from position 21 to position 129 of the amino acid sequence of SEQ ID NO: 37,
b4) an amino acid sequence having at least 95% identity to any one amino acid sequence selected from the amino acid sequences b1) to b3),
b5) an amino acid sequence having at least 99% identity to any one amino acid sequence selected from the amino acid sequences b1) to b3), or
b6) an amino acid sequence comprising a substitution(s), a deletion(s), or an addition(s) of one or several amino acid residues in any one amino acid sequence selected from the amino acid sequences b1) to b3).

13. The method of claim 1, wherein the anti-ALK2 antibody is:
an antibody consisting of a heavy chain comprising a heavy chain variable region consisting of amino acid residues from position 20 to position 142 of the amino acid sequence of SEQ ID NO: 31 and a light chain comprising a light chain variable region consisting of amino acid residues from position 21 to position 133 of the amino acid sequence of SEQ ID NO: 32;
an antibody consisting of a heavy chain comprising a heavy chain variable region consisting of amino acid residues from position 20 to position 142 of the amino acid sequence of SEQ ID NO: 33 and a light chain comprising a light chain variable region consisting of amino acid residues from position 21 to position 133 of the amino acid sequence of SEQ ID NO: 32;
an antibody consisting of a heavy chain comprising a heavy chain variable region consisting of amino acid residues from position 20 to position 140 of the amino acid sequence of SEQ ID NO: 34 and a light chain comprising a light chain variable region consisting of amino acid residues from position 21 to position 129 of the amino acid sequence of SEQ ID NO: 35;
an antibody consisting of a heavy chain comprising a heavy chain variable region consisting of amino acid residues from position 20 to position 140 of the amino acid sequence of SEQ ID NO: 36 and a light chain comprising a light chain variable region consisting of amino acid residues from position 21 to position 129 of the amino acid sequence of SEQ ID NO: 37;
an antibody consisting of a heavy chain comprising a heavy chain variable region consisting of amino acid residues from position 20 to position 140 of the amino acid sequence of SEQ ID NO: 38 and a light chain comprising a light chain variable region consisting of amino acid residues from position 21 to position 129 of the amino acid sequence of SEQ ID NO: 35; or
an antibody consisting of a heavy chain comprising a heavy chain variable region consisting of amino acid residues from position 20 to position 140 of the amino acid sequence of SEQ ID NO: 39 and a light chain comprising a light chain variable region consisting of amino acid residues from position 21 to position 129 of the amino acid sequence of SEQ ID NO: 37.

14. The method of claim 1, wherein the active mutation in ALK2 is a R206H mutation.

15. The method of claim 1, wherein the disease is selected from ectopic ossification, fibrodysplasia ossificans progressiva (FOP), and diffuse intrinsic pontine glioma (DIPG); the active mutation in ALK2 comprises at least one mutation selected from L196P, delP197_F198insL, R202I, R206H, Q207E, R258S, R258G, G325A, G328E, G328R, G328W, G356D, and R375P; and wherein the antibody or the antigen-binding fragment thereof comprises a heavy chain variable region comprising a CDRH1, a CDRH2, and a CDRH3, which comprise the amino acid sequences of:
SEQ ID NO: 5, SEQ ID NO: 6, and SEQ ID NO: 7, respectively,
SEQ ID NO: 11, SEQ ID NO: 12, and SEQ ID NO: 13, respectively,
SEQ ID NO: 18, SEQ ID NO: 19, and SEQ ID NO: 20, respectively, or
SEQ ID NO: 24, SEQ ID NO: 25, and SEQ ID NO: 26, respectively; and
a light chain variable region comprising a CDRL1, a CDRL2, and a CDRL3, which comprise the amino acid sequences of:
SEQ ID NO: 8, SEQ ID NO: 9, and SEQ ID NO: 10, respectively,
SEQ ID NO: 8, SEQ ID NO: 17, and SEQ ID NO: 10, respectively,
SEQ ID NO: 14, SEQ ID NO: 15, and SEQ ID NO: 16, respectively,
SEQ ID NO: 21, SEQ ID NO: 22, and SEQ ID NO: 23, respectively, or
SEQ ID NO: 27, SEQ ID NO: 28, and SEQ ID NO: 29, respectively.

16. The method of claim 1, wherein the amino acid residue at position 330 of the mutated ALK2 is proline.

17. A method of treating ectopic ossification or diffuse intrinsic pontine glioma (DIPG) in a subject in need thereof, comprising:

selecting the subject for treatment because the subject is determined to have a mutated ALK2 comprising at least one active mutation and no mutation at amino acid residue at position 330 of ALK2, and administering to the subject an anti-ALK2 antibody or an antigen-binding fragment thereof or a pharmaceutical composition comprising an anti-ALK2 antibody or an antigen-binding fragment thereof.

18. The method of claim 17, wherein the anti-ALK2 antibody or antigen-binding fragment thereof possesses a property of binding to the ALK2, a property of cross-linking the ALK2, and a property of inhibiting bone morphogenetic protein (BMP) signal transduction.

19. The method of claim 17, wherein the at least one active mutation comprises at least one mutation selected from L196P, delP197_F198insL, R202I, R206H, Q207E, R258S, R258G, G325A, G328E, G328R, G328W, G356D, and R375P.

* * * * *

SEQUENCE LISTING

<160> NUMBER OF SEQ ID NOS: 42

<210> SEQ ID NO 1
<211> LENGTH: 509
<212> TYPE: PRT

<213> ORGANISM: Homo sapiens

<400> SEQUENCE: 1

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
                20                  25                  30

Tyr Met Cys Val Cys Glu Gly Leu Ser Cys Gly Asn Glu Asp His Cys
            35                  40                  45

Glu Gly Gln Gln Cys Phe Ser Ser Leu Ser Ile Asn Asp Gly Phe His
        50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

```
Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
                435                 440                 445

Cys Val Asp Gln Gln Arg Pro Asn Ile Pro Asn Arg Trp Phe Ser Asp
        450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
                500                 505
```

```
<210> SEQ ID NO 2
<211> LENGTH: 3062
<212> TYPE: DNA
<213> ORGANISM: Homo sapiens

<400> SEQUENCE: 2
gaagagatgt gggcctctgg ggccgctgga ttcagtaact tccgtcgggt tctagactgg      60
ctcggctctg tccagtttgt gccagatagt ctcccacccc ctcccacccc ctcctttccc     120
ctggagattt gaacgctgct tgcatgggag aaaagctact tagagaagaa aacgttccac     180
ttagtaacag aagaaaagtc ttggttaaaa agttgtcatg aatttggctt ttggagagag     240
gcagcaagcc tggagcattg gtaagcgtca cactgccaaa gtgagagctg ctggagaact     300
cataatccca ggaacgcctc ttctactctc cgagtacccc agtgaccaga gtgagagaag     360
ctctgaacga gggcacgcgg cttgaaggac tgtgggcaga tgtgaccaag agcctgcatt     420
aagttgtaca atggtagatg gagtgatgat tcttcctgtg cttatcatga ttgctctccc     480
ctcccctagt atggaagatg agaagcccaa ggtcaacccc aaactctaca tgtgtgtgtg     540
tgaaggtctc tcctgcggta atgaggacca ctgtgaaggc cagcagtgct tttcctcact     600
gagcatcaac gatggcttcc acgtctacca gaaaggctgc ttccaggttt atgagcaggg     660
aaagatgacc tgtaagaccc cgccgtcccc tggccaagcc gtggagtgct gccaagggga     720
ctggtgtaac aggaacatca cggcccagct gcccactaaa ggaaaatcct tccctggaac     780
acagaatttc cacttggagg ttggcctcat tattctctct gtagtgttcg cagtatgtct     840
tttagcctgc ctgctgggag ttgctctccg aaaatttaaa aggcgcaacc aagaacgcct     900
caatccccga gacgtggagt atggcactat cgaagggctc atcaccacca atgttggaga     960
cagcacttta gcagatttat tggatcattc gtgtacatca ggaagtggct ctggtcttcc    1020
ttttctggta caaagaacag tggctcgcca gattacactg ttggagtgtg tcgggaaagg    1080
caggtatggt gaggtgtgga ggggcagctg gcaaggggag aatgttgccg tgaagatctt    1140
ctcctcccgt gatgagaagt catggttcag ggaaacggaa ttgtacaaca ctgtgatgct    1200
gaggcatgaa aatatcttag gtttcattgc ttcagacatg acatcaagac actccagtac    1260
ccagctgtgg ttaattacac attatcatga atgggatcgt tgtacgact  atcttcagct    1320 tactactctg gatacagtta gctgccttcg aatagtgctg tccatagcta gtggtcttgc    1380
acatttgcac atagagatat ttgggaccca agggaaacca gccattgccc atcgagattt    1440
aaagagcaaa aatattctgg ttaagaagaa tggacagtgt gcatagcag atttgggcct    1500
```

```
                                                             -continued ggcagtcatg cattcccaga gcaccaatca gcttgatgtg gggaacaatc cccgtgtggg    1560
caccaagcgc tacatggccc ccgaagttct agatgaaacc atccaggtgg attgtttcga    1620
ttcttataaa agggtcgata tttgggcctt tggacttgtt ttgtgggaag tggccaggcg    1680
gatggtgagc aatggtatag tggaggatta caagccaccg ttctacgatg tggttcccaa    1740
tgacccaagt tttgaagata tgaggaaggt agtctgtgtg atcaacaaa ggccaaacat     1800 acccaacaga tggttctcag acccgacatt aacctctctg ccaagctaa tgaaagaatg     1860 ctggtatcaa atccatccg caagactcac agcactgcgt atcaaaaga ctttgaccaa      1920 aattgataat tccctcgaca aattgaaaac tgactgttga catttcata gtgtcaagaa     1980 ggaagatttg acgttgttgt cattgtccag ctgggaccta atgctggcct gactggttgt    2040
cagaatggaa tccatctgtc tccctcccca aatggctgct ttgacaaggc agacgtcgta    2100
cccagccatg tgttggggag acatcaaaac caccctaacc tcgctcgatg actgtgaact    2160
gggcatttca cgaactgttc acactgcaga gactaatgtt ggacagacac tgttgcaaag    2220
gtagggactg gaggaacaca gagaaatcct aaaagagatc tgggcattaa gtcagtggct    2280
ttgcatagct ttcacaagtc tcctagacac tccccacggg aaactcaagg aggtggtgaa    2340
tttttaatca gcaatattgc ctgtgcttct cttctttatt gcactaggaa ttcttttgcat   2400 tccttacttg cactgttact cttaatttta aagacccaac ttgccaaaat gttggctgcg    2460
tactccactg gtctgtcttt ggataatagg aattcaattt ggcaaaacaa atgtaatgt     2520 cagactttgc tgcatttac acatgtgctg atgtttacaa tgatgccgaa cattaggaat    2580
tgtttataca caactttgca aattatttat tacttgtgca cttagtagtt tttacaaaac    2640
tgctttgtgc atatgttaaa gcttatttt atgtggtctt atgatttat tacagaaatg      2700 ttttaacac tatactctaa aatggacatt tcttttatt atcagttaaa atcacatttt      2760
aagtgcttca catttgtatg tgtgtagact gtaactttt ttcagttcat atgcagaacg     2820
tatttagcca ttacccacgt gacaccaccg aatatattac tgatttagaa gcaaagattt    2880
cagtagaatt ttagtcctga acgctacggg gaaaatgcat tttcttcaga attatccatt    2940
acgtgcattt aaactctgcc agaaaaaaat aactattttg ttttaatcta ctttttgtat    3000
ttagtagtta tttgtataaa ttaaataaac tgttttcaag tcaaaaaaaa aaaaaaaaaa    3060
aa                                                                  3062
```

<210> SEQ ID NO 3
<211> LENGTH: 509
<212> TYPE: PRT
<213> ORGANISM: Mus musculus

<400> SEQUENCE: 3

```
Met Val Asp Gly Val Met Ile Leu Pro Val Leu Met Met Met Ala Phe
 1               5                  10                  15

Pro Ser Pro Ser Val Glu Asp Glu Lys Pro Lys Val Asn Gln Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95
```

```
Asp Trp Cys Asn Arg Asn Ile Thr Ala Gln Leu Pro Thr Lys Gly Lys
                100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Ile Leu Gly Val
130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Glu Leu Leu Asp His Ser Cys Thr Ser Gly Ser
        180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
        210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
        260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
        290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Ser Ala Ile Ala His Arg Asp
                325                 330                 335

Leu Lys Ser Lys Asn Ile Leu Val Lys Lys Asn Gly Gln Cys Cys Ile
        340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
        420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
        450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
        500                 505
```

<210> SEQ ID NO 4
<211> LENGTH: 3312
<212> TYPE: DNA
<213> ORGANISM: Mus musculus

<400> SEQUENCE: 4

| | | | | | |
|---|---|---|---|---|---|
| ccgcctcccc | gggttcagca | cccgaccgcc | gctggaccag | aggaacaaag | gagctgcccc | 60 |
| cgtgtcaccc | agcccttcag | tggaagtctg | gaaaaggaac | agaggtgata | ttgcagtgga | 120 |
| tgagcagaga | gaagccggcc | tctggtgctc | ttgagctggt | ctgcccatag | ggagcctgct | 180 |
| gggagaaggt | acagcttccg | gaagactcct | cccggagcgc | ctctcccatc | ctcctctccc | 240 |
| ttggagcagt | cagtacctct | ctgctggagg | atctgggctg | gtgtgccgg | gagctggctt | 300 |
| taactgtagc | cctgtcaggc | tttccccgga | cctcgcggaa | gagcgtcacc | agccccacg | 360 |
| gcttt ccaac | acatcacctc | ttttcatgcc | gtttggcaca | gatcgaatct | acagggatga | 420 |
| atggatccag | ggtctggttt | taagttctat | ggtagtcgtc | caaggagcca | ttggtattca | 480 |
| tctaacgcaa | acgatcaagt | tacattctga | aagtaacatc | ccaccagaaa | ccctccagca | 540 |
| gcagtcacgt | ctgtgtaaag | ccaagccctg | gcatgcgcac | tgccaggtca | gagtgtggtg | 600 |
| gtacacgtgt | ttaacaggtc | atttgtcaac | tgaaggaaag | accccggctt | gacttacctg | 660 |
| ttatacaatg | gtcgatggag | taatgatcct | tcctgtgcta | atgatgatgg | ctttcccttc | 720 |
| cccgagtgtg | gaagatgaga | agcccaaggt | caaccagaaa | ctttacatgt | gtgtgtgtga | 780 |
| gggcctctcc | tgcgggaacg | aggaccactg | tgaaggccag | cagtgttttt | cttctctgag | 840 |
| catcaacgat | ggcttccacg | tctaccagaa | gggctgcttt | caggtttatg | agcaggggaa | 900 |
| gatgacgtgt | aagacccgc | cgtcacctgg | ccaggctgtg | gagtgctgcc | aagggggactg | 960 |
| gtgtaacagg | aacatcacgg | cccagctgcc | cactaaaggg | aagtccttcc | ccggaacaca | 1020 |
| gaatttccac | ctggaagttg | gccttatcat | cctctcggtg | gtgtttgcag | tatgtctttt | 1080 |
| agcttgcatc | cttggagttg | ctctcaggaa | gtttaagaga | cgcaatcaag | agcgcctgaa | 1140 |
| ccccagagac | gtggagtatg | gtaccattga | agggctcatc | accaccaatg | tgggagacag | 1200 |
| cactctagcg | gaactactag | atcactcgtg | tacatcagga | agtggctccg | gtcttccttt | 1260 |
| cctggtacag | agaacggtgg | ctcgccagat | aaccctgttg | gagtgtgtcg | ggaagggccg | 1320 |
| gtatggagaa | gtatggaggg | gcagctggca | aggcgaaaat | gtcgctgtga | agatcttctc | 1380 |
| ctcccgagac | gagaagtcat | ggttcaggga | gacggaattg | tacaacactg | tgatgttgag | 1440 |
| gcatgaaaat | atcttaggtt | tcatcgcttc | agacatgacc | tccagacact | ccagtaccca | 1500 |
| gctgtggctc | atcacacatt | accatgaaat | gggatcgttg | tatgactacc | ttcagctcac | 1560 |
| tactctggat | acggttagct | gccttcggat | tgtactgtcc | atagccagcg | gccttgccca | 1620 |
| tttgcacata | gagatatttg | ggacccaagg | gaagtccgcc | attgcccatc | gagatctgaa | 1680 |
| gagcaaaaac | atcctggtga | agaagaatgg | acagtgctgc | atagcagatt | tgggcctggc | 1740 |
| agtcatgcat | tcccagagca | caaaccagct | tgatgtggga | aacaaccccc | gtgtggggac | 1800 |
| caagcgctac | atggctccgg | aagtgctcga | tgaaaccatc | caagtggatt | gctttgattc | 1860 |
| ttataagagg | gtcgatattt | gggccttttg | ccttgttctg | tgggaagtgg | ccaggcgaat | 1920 |
| ggtgagcaat | ggtatagtgg | aagattacaa | gccaccattc | tatgatgtgg | ttcccaatga | 1980 |
| cccaagtttt | gaagatatga | ggaaagttgt | ctgtgtggat | caacagaggc | caaacatacc | 2040 |
| taacagatgg | ttctcagacc | cgacattaac | ttctctggcg | aagctgatga | agagtgctg | 2100 |
| gtatcagaac | ccatccgcaa | gactcacagc | tctacgtatc | aaaaagactt | tgaccaaaat | 2160 |

-continued

```
cgataattcc ctagacaaat taaaaactga ctgttgacct tgtcaccggt gtcaagaagg    2220
agagtcaatg ctgtccttgt ccagctggga cctaatgctg gcctgactgg ttgtcagaac    2280
agaatccatc tgaccccctt cccgaagtgg ctgctttgac ggaagcagat gtctcttccc    2340
agccatgttc caggggggaga caccaaaacc accctaacct cgctcaaaaa ctgtgactcg    2400
agccctcgat gaactgttca caccacaaag acttaacggt gggcaggtct ggtggcaagg    2460
gggagggaag tggaggaacc cggaaagatc ctgcaggcga tctgggcatt aagacagtgg    2520
ctctctgcgt atctttcgcg ggtctcctag acactcccca cgggaagctc aaggaggcgg    2580
tgaattcgta atcagcaata tcggctgcat ctactcttcg ttgcactagg aattctgtgc    2640
attccttact tgcactgtgg cccttaatct taaagaccca acttgccaaa acattggctg    2700
cgtactccac tggcctgtct ctggataata ggaattcaat ctggcaacac aaaaatgtac    2760
cgttggactc tgctgcattt tacacacgtg ctgatgttta caaggatgcg aacattagga    2820
attgtttaga cacaactttg caaattattt attactggtg cacttagcgg tttgtttgaa    2880
accgcctcgt gcatatgtta aagcttattt ttatgtggtc ttatgatttt attaccgaaa    2940 tgttttttaac acccaactct gaaacggaca ttttcttta ttatcagtta aattcacatt    3000
taagtgcttc acattttttt ttttaaatgt gtgtagactg taactttctt ttcagttcgt    3060
atgcagaaca tatttagcca ttacccatgc aacaccaccc gatatattac tgatttagaa    3120
gcaaagattt cagtagaatt ttagtcccaa acgctgtggg gggaaatgca tcttcttcgg    3180
aattatccat tacgtgcatt taaactctgc cagaaaaaaa aataactatt ttgttttaat    3240 ctacttttg tatttagtag ttatttgtat aaattaaata aactgttttc aagtcaaaaa    3300
aaaaaaaaaa aa                                                        3312
```

<210> SEQ ID NO 5
<211> LENGTH: 10
<212> TYPE: PRT
<213> ORGANISM: Rattus norvegicus

<400> SEQUENCE: 5

Gly Phe Thr Phe Ser His Tyr Tyr Met Ala
1               5                   10

<210> SEQ ID NO 6
<211> LENGTH: 17
<212> TYPE: PRT
<213> ORGANISM: Rattus norvegicus

<400> SEQUENCE: 6

Ser Ile Thr Asn Ser Gly Gly Ser Ile Asn Tyr Arg Asp Ser Val Lys
1               5                   10                  15

Gly

<210> SEQ ID NO 7
<211> LENGTH: 14
<212> TYPE: PRT
<213> ORGANISM: Rattus norvegicus

<400> SEQUENCE: 7

Glu Gly Gly Glu Asn Tyr Gly Gly Tyr Pro Pro Phe Ala Tyr
1               5                   10

<210> SEQ ID NO 8
<211> LENGTH: 15

-continued

```
<212> TYPE: PRT
<213> ORGANISM: Rattus norvegicus

<400> SEQUENCE: 8

Arg Ala Asn Gln Gly Val Ser Leu Ser Arg Tyr Asn Leu Met His
1               5                   10                  15

<210> SEQ ID NO 9
<211> LENGTH: 7
<212> TYPE: PRT
<213> ORGANISM: Rattus norvegicus

<400> SEQUENCE: 9

Arg Ser Ser Asn Leu Ala Ser
1               5

<210> SEQ ID NO 10
<211> LENGTH: 9
<212> TYPE: PRT
<213> ORGANISM: Rattus norvegicus

<400> SEQUENCE: 10

Gln Gln Ser Arg Glu Ser Pro Phe Thr
1               5

<210> SEQ ID NO 11
<211> LENGTH: 10
<212> TYPE: PRT
<213> ORGANISM: Rattus norvegicus

<400> SEQUENCE: 11

Gly Ser Thr Phe Ser Asn Tyr Gly Met Lys
1               5                   10

<210> SEQ ID NO 12
<211> LENGTH: 17
<212> TYPE: PRT
<213> ORGANISM: Rattus norvegicus

<400> SEQUENCE: 12

Ser Ile Ser Arg Ser Ser Thr Tyr Ile Tyr Tyr Ala Asp Thr Val Lys
1               5                   10                  15
Gly

<210> SEQ ID NO 13
<211> LENGTH: 12
<212> TYPE: PRT
<213> ORGANISM: Rattus norvegicus

<400> SEQUENCE: 13

Ala Ile Ser Thr Pro Phe Tyr Trp Tyr Phe Asp Phe
1               5                   10

<210> SEQ ID NO 14
<211> LENGTH: 10
<212> TYPE: PRT
<213> ORGANISM: Rattus norvegicus

<400> SEQUENCE: 14

Leu Ala Ser Ser Ser Val Ser Tyr Met Thr
1               5                   10

<210> SEQ ID NO 15
<211> LENGTH: 7
```

```
<212> TYPE: PRT
<213> ORGANISM: Rattus norvegicus

<400> SEQUENCE: 15

Gly Thr Ser Asn Leu Ala Ser
1               5

<210> SEQ ID NO 16
<211> LENGTH: 10
<212> TYPE: PRT
<213> ORGANISM: Rattus norvegicus

<400> SEQUENCE: 16

Leu His Leu Thr Ser Tyr Pro Pro Tyr Thr
1               5                   10

<210> SEQ ID NO 17
<211> LENGTH: 7
<212> TYPE: PRT
<213> ORGANISM: Artificial
<220> FEATURE:
<223> OTHER INFORMATION: Gln is a substituted amino acid residue.

<400> SEQUENCE: 17

Arg Ser Ser Asn Leu Ala Gln
1               5

<210> SEQ ID NO 18
<211> LENGTH: 10
<212> TYPE: PRT
<213> ORGANISM: Rattus norvegicus

<400> SEQUENCE: 18

Gly Phe Thr Phe Ser Asn Tyr Tyr Met Tyr
1               5                   10

<210> SEQ ID NO 19
<211> LENGTH: 17
<212> TYPE: PRT
<213> ORGANISM: Rattus norvegicus

<400> SEQUENCE: 19

Ser Ile Asn Thr Asp Gly Gly Ser Thr Tyr Tyr Pro Asp Ser Val Lys
1               5                   10                  15

Gly

<210> SEQ ID NO 20
<211> LENGTH: 9
<212> TYPE: PRT
<213> ORGANISM: Rattus norvegicus

<400> SEQUENCE: 20

Ser Thr Pro Asn Ile Pro Leu Ala Tyr
1               5

<210> SEQ ID NO 21
<211> LENGTH: 11
<212> TYPE: PRT
<213> ORGANISM: Rattus norvegicus

<400> SEQUENCE: 21

Lys Ala Ser Gln Asn Ile Tyr Lys Tyr Leu Asn
1               5                   10
```

```
<210> SEQ ID NO 22
<211> LENGTH: 7
<212> TYPE: PRT
<213> ORGANISM: Rattus norvegicus

<400> SEQUENCE: 22

Tyr Ser Asn Ser Leu Gln Thr
1               5

<210> SEQ ID NO 23
<211> LENGTH: 8
<212> TYPE: PRT
<213> ORGANISM: Rattus norvegicus

<400> SEQUENCE: 23

Phe Gln Tyr Ser Ser Gly Pro Thr
1               5

<210> SEQ ID NO 24
<211> LENGTH: 10
<212> TYPE: PRT
<213> ORGANISM: Rattus norvegicus

<400> SEQUENCE: 24

Gly Phe Thr Phe Ser Tyr Tyr Ala Met Ser
1               5                   10

<210> SEQ ID NO 25
<211> LENGTH: 17
<212> TYPE: PRT
<213> ORGANISM: Rattus norvegicus

<400> SEQUENCE: 25

Ser Ile Ser Arg Gly Gly Asp Asn Thr Tyr Tyr Arg Asp Thr Val Lys
1               5                   10                  15

Gly

<210> SEQ ID NO 26
<211> LENGTH: 9
<212> TYPE: PRT
<213> ORGANISM: Rattus norvegicus

<400> SEQUENCE: 26

Leu Asn Tyr Asn Asn Tyr Phe Asp Tyr
1               5

<210> SEQ ID NO 27
<211> LENGTH: 11
<212> TYPE: PRT
<213> ORGANISM: Rattus norvegicus

<400> SEQUENCE: 27

Gln Ala Ser Gln Asp Ile Gly Asn Trp Leu Ser
1               5                   10

<210> SEQ ID NO 28
<211> LENGTH: 7
<212> TYPE: PRT
<213> ORGANISM: Rattus norvegicus

<400> SEQUENCE: 28

Gly Ala Thr Ser Leu Ala Asp
1               5
```

<210> SEQ ID NO 29
<211> LENGTH: 9
<212> TYPE: PRT
<213> ORGANISM: Rattus norvegicus

<400> SEQUENCE: 29

Leu Gln Ala Tyr Ser Ala Pro Phe Thr
1               5

<210> SEQ ID NO 30
<211> LENGTH: 238
<212> TYPE: PRT
<213> ORGANISM: Artificial
<220> FEATURE:
<223> OTHER INFORMATION: Amino acid sequence of humanized hA2-15A-L4
<220> FEATURE:
<221> NAME/KEY: SIGNAL
<222> LOCATION: (1)..(20)
<220> FEATURE:
<221> NAME/KEY: V_region
<222> LOCATION: (21)..(133)
<220> FEATURE:
<221> NAME/KEY: C_region
<222> LOCATION: (134)..(238)

<400> SEQUENCE: 30

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Asp Ser Leu Ala
            20                  25                  30

Val Ser Leu Gly Glu Arg Ala Thr Ile Asn Cys Arg Ala Asn Gln Gly
        35                  40                  45

Val Ser Leu Ser Arg Tyr Asn Leu Met His Trp Tyr Gln Gln Lys Pro
    50                  55                  60

Gly Gln Lys Pro Lys Leu Leu Ile Tyr Arg Ser Ser Asn Leu Ala Ser
65                  70                  75                  80

Gly Ile Pro Ala Arg Phe Ser Gly Ser Gly Ser Gly Thr Asp Phe Thr
                85                  90                  95

Leu Thr Ile Ser Ser Val Gln Ala Asp Asp Ile Ala Val Tyr Tyr Cys
            100                 105                 110

Gln Gln Ser Arg Glu Ser Pro Phe Thr Phe Gly Gln Gly Thr Lys Leu
        115                 120                 125

Glu Leu Lys Arg Ala Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 31
<211> LENGTH: 472
<212> TYPE: PRT
<213> ORGANISM: Artificial

```
<220> FEATURE:
<223> OTHER INFORMATION: Amino acid sequence of humanized hA2-15A-H4
<220> FEATURE:
<221> NAME/KEY: SIGNAL
<222> LOCATION: (1)..(19)
<220> FEATURE:
<221> NAME/KEY: V_region
<222> LOCATION: (20)..(142)
<220> FEATURE:
<221> NAME/KEY: C_region
<222> LOCATION: (143)..(472)

<400> SEQUENCE: 31
```

Met Lys His Leu Trp Phe Phe Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser His Tyr Tyr Met Ala Trp Val Arg Gln Ala Pro Gly Lys Gly Leu
    50                  55                  60

Glu Trp Val Ala Ser Ile Thr Asn Ser Gly Gly Ser Ile Asn Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asn Ser Leu Arg Ala Glu Asp Thr Ala Thr
            100                 105                 110

Tyr Tyr Cys Thr Arg Glu Gly Gly Glu Asn Tyr Gly Gly Tyr Pro Pro
        115                 120                 125

Phe Ala Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

```
Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
            450                 455                 460

Ser Leu Ser Leu Ser Pro Gly Lys
465                 470

<210> SEQ ID NO 32
<211> LENGTH: 238
<212> TYPE: PRT
<213> ORGANISM: Artificial
<220> FEATURE:
<223> OTHER INFORMATION: Amino acid sequence of humanized hA2-15A-L6
<220> FEATURE:
<221> NAME/KEY: SIGNAL
<222> LOCATION: (1)..(20)
<220> FEATURE:
<221> NAME/KEY: V_region
<222> LOCATION: (21)..(133)
<220> FEATURE:
<221> NAME/KEY: C_region
<222> LOCATION: (134)..(238)

<400> SEQUENCE: 32

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Asp Ser Leu Ala
                20                  25                  30

Val Ser Leu Gly Glu Arg Ala Thr Ile Asn Cys Arg Ala Asn Gln Gly
            35                  40                  45

Val Ser Leu Ser Arg Tyr Asn Leu Met His Trp Tyr Gln Gln Lys Pro
        50                  55                  60

Gly Gln Lys Pro Lys Leu Leu Ile Tyr Arg Ser Ser Asn Leu Ala Gln
65                  70                  75                  80

Gly Ile Pro Ala Arg Phe Ser Gly Ser Gly Ser Gly Thr Asp Phe Thr
                85                  90                  95

Leu Thr Ile Ser Ser Val Gln Ala Asp Asp Ile Ala Val Tyr Tyr Cys
            100                 105                 110

Gln Gln Ser Arg Glu Ser Pro Phe Thr Phe Gly Gln Gly Thr Lys Leu
        115                 120                 125

Glu Leu Lys Arg Ala Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190
```

```
Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 33
<211> LENGTH: 468
<212> TYPE: PRT
<213> ORGANISM: Artificial
<220> FEATURE:
<223> OTHER INFORMATION: amino acid sequence of humanized
      hA2-15A-H4_IgG2 type

<400> SEQUENCE: 33

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser His Tyr Tyr Met Ala Trp Val Arg Gln Ala Pro Gly Lys Gly Leu
    50                  55                  60

Glu Trp Val Ala Ser Ile Thr Asn Ser Gly Gly Ser Ile Asn Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asn Ser Leu Arg Ala Glu Asp Thr Ala Thr
            100                 105                 110

Tyr Tyr Cys Thr Arg Glu Gly Gly Glu Asn Tyr Gly Gly Tyr Pro Pro
        115                 120                 125

Phe Ala Tyr Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
```

```
305                 310                 315                 320
Phe Arg Val Val Ser Val Leu Thr Val Val His Gln Asp Trp Leu Asn
                325                 330                 335
Gly Lys Glu Tyr Lys Cys Lys Val Ser Asn Lys Gly Leu Pro Ala Pro
            340                 345                 350
Ile Glu Lys Thr Ile Ser Lys Thr Lys Gly Gln Pro Arg Glu Pro Gln
            355                 360                 365
Val Tyr Thr Leu Pro Pro Ser Arg Glu Glu Met Thr Lys Asn Gln Val
        370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Met Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
            435                 440                 445
Met His Glu Ala Leu His Asn His Tyr Thr Gln Lys Ser Leu Ser Leu
        450                 455                 460
Ser Pro Gly Lys
465

<210> SEQ ID NO 34
<211> LENGTH: 470
<212> TYPE: PRT
<213> ORGANISM: Artificial
<220> FEATURE:
<223> OTHER INFORMATION: Amino acid sequence of humanized hA2-27D-H2
<220> FEATURE:
<221> NAME/KEY: SIGNAL
<222> LOCATION: (1)..(19)
<220> FEATURE:
<221> NAME/KEY: V_region
<222> LOCATION: (20)..(140)
<220> FEATURE:
<221> NAME/KEY: C_region
<222> LOCATION: (141)..(470)

<400> SEQUENCE: 34

Met Lys His Leu Trp Phe Phe Leu Leu Leu Val Ala Ala Pro Arg Trp
1               5                   10                  15
Val Leu Ser Glu Val Gln Leu Val Glu Ser Gly Gly Gly Leu Val Gln
            20                  25                  30
Pro Gly Gly Ser Leu Arg Leu Ser Cys Ala Ala Ser Gly Ser Thr Phe
        35                  40                  45
Ser Asn Tyr Gly Met Lys Trp Ile Arg Gln Ala Pro Gly Lys Gly Leu
    50                  55                  60
Glu Trp Val Ser Ser Ile Ser Arg Ser Ser Thr Tyr Ile Tyr Tyr Ala
65                  70                  75                  80
Asp Thr Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
            100                 105                 110
Tyr Tyr Cys Ala Ala Ile Ser Thr Pro Phe Tyr Trp Tyr Phe Asp
        115                 120                 125
Phe Trp Gly Gln Gly Thr Leu Val Thr Val Ser Ser Ala Ser Thr Lys
    130                 135                 140
Gly Pro Ser Val Phe Pro Leu Ala Pro Ser Ser Lys Ser Thr Ser Gly
```

145                 150                 155                 160
        Gly Thr Ala Ala Leu Gly Cys Leu Val Lys Asp Tyr Phe Pro Glu Pro
                        165                 170                 175

Val Thr Val Ser Trp Asn Ser Gly Ala Leu Thr Ser Gly Val His Thr
                    180                 185                 190

Phe Pro Ala Val Leu Gln Ser Ser Gly Leu Tyr Ser Leu Ser Ser Val
                195                 200                 205

Val Thr Val Pro Ser Ser Leu Gly Thr Gln Thr Tyr Ile Cys Asn
        210                 215                 220

Val Asn His Lys Pro Ser Asn Thr Lys Val Asp Lys Arg Val Glu Pro
        225                 230                 235                 240

Lys Ser Cys Asp Lys Thr His Thr Cys Pro Pro Cys Pro Ala Pro Glu
                        245                 250                 255

Leu Leu Gly Gly Pro Ser Val Phe Leu Phe Pro Pro Lys Pro Lys Asp
                    260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
        305                 310                 315                 320

Ser Thr Tyr Arg Val Val Ser Val Leu Thr Val Leu His Gln Asp Trp
                        325                 330                 335

Leu Asn Gly Lys Glu Tyr Lys Cys Lys Val Ser Asn Lys Ala Leu Pro
                    340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Glu Glu Met Thr Lys Asn
            370                 375                 380

Gln Val Ser Leu Thr Cys Leu Val Lys Gly Phe Tyr Pro Ser Asp Ile
        385                 390                 395                 400

Ala Val Glu Trp Glu Ser Asn Gly Gln Pro Glu Asn Asn Tyr Lys Thr
                        405                 410                 415

Thr Pro Pro Val Leu Asp Ser Asp Gly Ser Phe Phe Leu Tyr Ser Lys
                    420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
            450                 455                 460

Ser Leu Ser Pro Gly Lys
        465                 470

<210> SEQ ID NO 35
<211> LENGTH: 234
<212> TYPE: PRT
<213> ORGANISM: Artificial
<220> FEATURE:
<223> OTHER INFORMATION: Amino acid sequence of humanized hA2-27D-L2
<220> FEATURE:
<221> NAME/KEY: SIGNAL
<222> LOCATION: (1)..(20)
<220> FEATURE:
<221> NAME/KEY: V_region
<222> LOCATION: (21)..(129)
<220> FEATURE:
<221> NAME/KEY: C_region
<222> LOCATION: (130)..(234)

<400> SEQUENCE: 35

Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Gly Thr Leu Ser
            20                  25                  30

Leu Ser Pro Gly Glu Arg Ala Thr Leu Ser Cys Leu Ala Ser Ser Ser
        35                  40                  45

Val Ser Tyr Met Thr Trp Tyr Gln Gln Lys Pro Gly Gln Ser Pro Arg
50                  55                  60

Leu Trp Ile Tyr Gly Thr Ser Asn Leu Ala Ser Gly Val Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys Leu His Leu Thr Ser
            100                 105                 110

Tyr Pro Pro Tyr Thr Phe Gly Gln Gly Thr Lys Val Glu Ile Lys Arg
        115                 120                 125

Ala Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 36
<211> LENGTH: 470
<212> TYPE: PRT
<213> ORGANISM: Artificial
<220> FEATURE:
<223> OTHER INFORMATION: Amino acid sequence of humanized hA2-27D-H3
<220> FEATURE:
<221> NAME/KEY: SIGNAL
<222> LOCATION: (1)..(19)
<220> FEATURE:
<221> NAME/KEY: V_region
<222> LOCATION: (20)..(140)
<220> FEATURE:
<221> NAME/KEY: C_region
<222> LOCATION: (141)..(470)

<400> SEQUENCE: 36

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Ser Thr Phe
        35                  40                  45

Ser Asn Tyr Gly Met Lys Trp Ile Arg Gln Ala Pro Gly Lys Gly Leu
50                  55                  60

Glu Trp Val Ala Ser Ile Ser Arg Ser Ser Thr Tyr Ile Tyr Tyr Ala

-continued

```
            65                  70                  75                  80
        Asp Thr Val Lys Gly Arg Phe Thr Ile Ser Arg Asp Asn Ser Lys Asn
                        85                  90                  95
        Thr Leu Tyr Leu Gln Met Asn Ser Leu Arg Ala Glu Asp Thr Ala Val
                       100                 105                 110
        Tyr Tyr Cys Ala Ala Ile Ser Thr Pro Phe Tyr Trp Tyr Phe Asp
                       115                 120                 125
        Phe Trp Gly Gln Gly Thr Leu Val Thr Val Ser Ser Ala Ser Thr Lys
                       130                 135                 140
        Gly Pro Ser Val Phe Pro Leu Ala Pro Ser Ser Lys Ser Thr Ser Gly
        145                 150                 155                 160
        Gly Thr Ala Ala Leu Gly Cys Leu Val Lys Asp Tyr Phe Pro Glu Pro
                       165                 170                 175
        Val Thr Val Ser Trp Asn Ser Gly Ala Leu Thr Ser Gly Val His Thr
                       180                 185                 190
        Phe Pro Ala Val Leu Gln Ser Ser Gly Leu Tyr Ser Leu Ser Ser Val
                       195                 200                 205
        Val Thr Val Pro Ser Ser Leu Gly Thr Gln Thr Tyr Ile Cys Asn
                       210                 215                 220
        Val Asn His Lys Pro Ser Asn Thr Lys Val Asp Lys Arg Val Glu Pro
        225                 230                 235                 240
        Lys Ser Cys Asp Lys Thr His Thr Cys Pro Pro Cys Pro Ala Pro Glu
                       245                 250                 255
        Leu Leu Gly Gly Pro Ser Val Phe Leu Phe Pro Pro Lys Pro Lys Asp
                       260                 265                 270
        Thr Leu Met Ile Ser Arg Thr Pro Glu Val Thr Cys Val Val Val Asp
                       275                 280                 285
        Val Ser His Glu Asp Pro Glu Val Lys Phe Asn Trp Tyr Val Asp Gly
                       290                 295                 300
        Val Glu Val His Asn Ala Lys Thr Lys Pro Arg Glu Glu Gln Tyr Asn
        305                 310                 315                 320
        Ser Thr Tyr Arg Val Val Ser Val Leu Thr Val Leu His Gln Asp Trp
                       325                 330                 335
        Leu Asn Gly Lys Glu Tyr Lys Cys Lys Val Ser Asn Lys Ala Leu Pro
                       340                 345                 350
        Ala Pro Ile Glu Lys Thr Ile Ser Lys Ala Lys Gly Gln Pro Arg Glu
                       355                 360                 365
        Pro Gln Val Tyr Thr Leu Pro Pro Ser Arg Glu Glu Met Thr Lys Asn
                       370                 375                 380
        Gln Val Ser Leu Thr Cys Leu Val Lys Gly Phe Tyr Pro Ser Asp Ile
        385                 390                 395                 400
        Ala Val Glu Trp Glu Ser Asn Gly Gln Pro Glu Asn Asn Tyr Lys Thr
                       405                 410                 415
        Thr Pro Pro Val Leu Asp Ser Asp Gly Ser Phe Phe Leu Tyr Ser Lys
                       420                 425                 430
        Leu Thr Val Asp Lys Ser Arg Trp Gln Gln Gly Asn Val Phe Ser Cys
                       435                 440                 445
        Ser Val Met His Glu Ala Leu His Asn His Tyr Thr Gln Lys Ser Leu
        450                 455                 460
        Ser Leu Ser Pro Gly Lys
                       470

<210> SEQ ID NO 37
```

```
<211> LENGTH: 234
<212> TYPE: PRT
<213> ORGANISM: Artificial
<220> FEATURE:
<223> OTHER INFORMATION: Amino acid sequence of humanized hA2-27D-L4
<220> FEATURE:
<221> NAME/KEY: SIGNAL
<222> LOCATION: (1)..(20)
<220> FEATURE:
<221> NAME/KEY: V_region
<222> LOCATION: (21)..(129)
<220> FEATURE:
<221> NAME/KEY: C_region
<222> LOCATION: (130)..(234)

<400> SEQUENCE: 37
```

Met Val Leu Gln Thr Gln Val Phe Ile Ser Leu Leu Trp Ile Ser
1               5                   10                  15

Gly Ala Tyr Gly Glu Ile Val Leu Thr Gln Ser Pro Gly Thr Met Ser
            20                  25                  30

Ala Ser Pro Gly Glu Arg Val Thr Leu Ser Cys Leu Ala Ser Ser Ser
        35                  40                  45

Val Ser Tyr Met Thr Trp Tyr Gln Gln Lys Pro Gly Ala Ser Pro Arg
    50                  55                  60

Leu Trp Ile Tyr Gly Thr Ser Asn Leu Ala Ser Gly Val Pro Asp Arg
65                  70                  75                  80

Phe Ser Gly Ser Gly Ser Gly Thr Asp Tyr Thr Leu Thr Ile Ser Arg
                85                  90                  95

Met Glu Pro Glu Asp Phe Ala Thr Tyr Tyr Cys Leu His Leu Thr Ser
            100                 105                 110

Tyr Pro Pro Tyr Thr Phe Gly Ala Gly Thr Lys Leu Glu Leu Lys Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

```
<210> SEQ ID NO 38
<211> LENGTH: 470
<212> TYPE: PRT
<213> ORGANISM: Artificial
<220> FEATURE:
<223> OTHER INFORMATION: amino acid sequence of humanized
      hA2-27D-H2_LALA

<400> SEQUENCE: 38
```

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

```
Pro Gly Gly Ser Leu Arg Leu Ser Cys Ala Ala Ser Gly Ser Thr Phe
            35                  40                  45
Ser Asn Tyr Gly Met Lys Trp Ile Arg Gln Ala Pro Gly Lys Gly Leu
    50                  55                  60
Glu Trp Val Ser Ser Ile Ser Arg Ser Ser Thr Tyr Ile Tyr Tyr Ala
65                  70                  75                  80
Asp Thr Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
                100                 105                 110
Tyr Tyr Cys Ala Ala Ala Ile Ser Thr Pro Phe Tyr Trp Tyr Phe Asp
            115                 120                 125
Phe Trp Gly Gln Gly Thr Leu Val Thr Val Ser Ser Ala Ser Thr Lys
    130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
                180                 185                 190
Phe Pro Ala Val Leu Gln Ser Ser Gly Leu Tyr Ser Leu Ser Ser Val
            195                 200                 205
Val Thr Val Pro Ser Ser Ser Leu Gly Thr Gln Thr Tyr Ile Cys Asn
    210                 215                 220
Val Asn His Lys Pro Ser Asn Thr Lys Val Asp Lys Arg Val Glu Pro
225                 230                 235                 240
Lys Ser Cys Asp Lys Thr His Thr Cys Pro Pro Cys Pro Ala Pro Glu
                245                 250                 255
Ala Ala Gly Gly Pro Ser Val Phe Leu Phe Pro Pro Lys Pro Lys Asp
                260                 265                 270
Thr Leu Met Ile Ser Arg Thr Pro Glu Val Thr Cys Val Val Val Asp
            275                 280                 285
Val Ser His Glu Asp Pro Glu Val Lys Phe Asn Trp Tyr Val Asp Gly
    290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
                340                 345                 350
Ala Pro Ile Glu Lys Thr Ile Ser Lys Ala Lys Gly Gln Pro Arg Glu
            355                 360                 365
Pro Gln Val Tyr Thr Leu Pro Pro Ser Arg Glu Glu Met Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
                420                 425                 430
Leu Thr Val Asp Lys Ser Arg Trp Gln Gln Gly Asn Val Phe Ser Cys
            435                 440                 445
Ser Val Met His Glu Ala Leu His Asn His Tyr Thr Gln Lys Ser Leu
```

Ser Leu Ser Pro Gly Lys
465                 470

<210> SEQ ID NO 39
<211> LENGTH: 470
<212> TYPE: PRT
<213> ORGANISM: Artificial
<220> FEATURE:
<223> OTHER INFORMATION: amino acid sequence of humanized
      hA2-27D-H3_LALA

<400> SEQUENCE: 39

Met Lys His Leu Trp Phe Phe Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Ser Thr Phe
            35                  40                  45

Ser Asn Tyr Gly Met Lys Trp Ile Arg Gln Ala Pro Gly Lys Gly Leu
        50                  55                  60

Glu Trp Val Ala Ser Ile Ser Arg Ser Ser Thr Tyr Ile Tyr Tyr Ala
65                  70                  75                  80

Asp Thr Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Ala Ala Ile Ser Thr Pro Phe Tyr Trp Tyr Phe Asp
            115                 120                 125

Phe Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
        210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Ala Ala Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

```
Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 40
<211> LENGTH: 509
<212> TYPE: PRT
<213> ORGANISM: Macca mulatta

<400> SEQUENCE: 40

Met Val Asp Gly Val Met Ile Leu Pro Val Leu Ile Ile Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240
```

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 41
<211> LENGTH: 509
<212> TYPE: PRT
<213> ORGANISM: Canis lupus

<400> SEQUENCE: 41

Met Val Asp Gly Val Met Met Leu Pro Val Leu Met Met Ile Ala Phe
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys

```
              100                 105                 110
Ser Phe Pro Glu Thr Gln Asn Phe His Leu Glu Val Gly Leu Ile Ile
            115                 120                 125

Leu Ser Val Val Phe Ala Val Cys Leu Leu Ala Cys Leu Leu Gly Val
        130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 42
```

<211> LENGTH: 509
<212> TYPE: PRT
<213> ORGANISM: Rattus norvegicus

<400> SEQUENCE: 42

```
Met Val Asp Gly Ala Met Ile Leu Ser Val Leu Met Met Ala Leu
1               5                   10                  15

Pro Ser Pro Ser Met Glu Asp Glu Pro Lys Val Asn Pro Lys Leu
                20                  25                  30

Tyr Met Cys Val Cys Glu Gly Leu Ser Cys Gly Asn Glu Asp His Cys
            35                  40                  45

Glu Gly Gln Gln Cys Phe Ser Ser Leu Ser Val Asn Asp Gly Phe Arg
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Val Thr Ala Arg Leu Pro Thr Lys Gly Lys
                100                 105                 110

Ser Phe Pro Gly Ser Gln Asn Phe His Leu Glu Val Gly Leu Ile Ile
            115                 120                 125

Leu Ser Val Val Phe Ala Val Cys Leu Phe Ala Cys Ile Leu Gly Val
130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Glu Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Ser Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
```

```
385                 390                 395                 400
Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
                420                 425                 430

Asp Val Val Pro Asn Asp Pro Ser Phe Glu Asp Met Arg Lys Val Val
            435                 440                 445

Cys Val Asp Gln Gln Arg Pro Asn Ile Pro Asn Arg Trp Phe Ser Asp
        450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
                500                 505
```